US008670816B2

(12) United States Patent
Green et al.

(10) Patent No.: US 8,670,816 B2
(45) Date of Patent: Mar. 11, 2014

(54) MULTIPLE MEDICAL DEVICE GUIDANCE

(71) Applicant: Inneroptic Technology, Inc., Hillsborough, NC (US)

(72) Inventors: Caroline Green, Carrborro, NC (US); Brian Heaney, Durham, NC (US); Sharif Razzaque, Chapel Hill, NC (US); Andrei State, Chapel Hill, NC (US)

(73) Assignee: InnerOptic Technology, Inc., Hillsborough, NC (US)

( * ) Notice: Subject to any disclaimer, the term of this patent is extended or adjusted under 35 U.S.C. 154(b) by 0 days.

(21) Appl. No.: 13/753,274

(22) Filed: Jan. 29, 2013

(65) Prior Publication Data

US 2013/0197357 A1    Aug. 1, 2013

Related U.S. Application Data

(60) Provisional application No. 61/592,531, filed on Jan. 30, 2012, provisional application No. 61/736,789, filed on Dec. 13, 2012.

(51) Int. Cl.
*A61B 8/00* (2006.01)

(52) U.S. Cl.
USPC ........... 600/424; 600/407; 600/427; 600/437; 600/439

(58) Field of Classification Search
USPC .......................... 600/407, 424, 427, 437, 439
See application file for complete search history.

(56) References Cited

U.S. PATENT DOCUMENTS

| | | |
|---|---|---|
| 3,556,079 A | 1/1971 | Omizo |
| 4,058,114 A | 11/1977 | Soldner |
| RE30,397 E | 9/1980 | King |
| 4,249,539 A | 2/1981 | Vilkomerson et al. |
| 4,294,544 A | 10/1981 | Altschuler et al. |
| 4,390,025 A | 6/1983 | Takemura et al. |
| 4,407,294 A | 10/1983 | Vilkomerson |
| 4,431,006 A | 2/1984 | Trimmer et al. |
| 4,567,896 A | 2/1986 | Barnea et al. |
| 4,583,538 A | 4/1986 | Onik et al. |
| 4,620,546 A | 11/1986 | Aida et al. |
| 4,671,292 A | 6/1987 | Matzuk |
| 4,839,836 A | 6/1989 | Fonsalas |
| 4,862,873 A | 9/1989 | Yajima et al. |
| 4,884,219 A | 11/1989 | Waldren |

(Continued)

FOREIGN PATENT DOCUMENTS

| | | |
|---|---|---|
| AU | 7656896 A | 5/1997 |
| AU | 9453898 A | 4/1999 |

(Continued)

OTHER PUBLICATIONS

U.S. Appl. No. 11/828,826, filed Jul. 26, 2007, Keller et al.

(Continued)

*Primary Examiner* — Peter Luong
(74) *Attorney, Agent, or Firm* — Knobbe Martens Olson & Bear, LLP

(57) ABSTRACT

A system and method for providing image guidance for placement of one or more medical devices at a target location. The system receives emplacement information of medical devices within a predetermined area. The system calculates a viewing angle in a virtual 3D space of a plurality of virtual medical devices corresponding to the plurality of medical devices. The system also causes a display device to display the plurality of virtual medical devices based at least on the calculated viewing angle.

24 Claims, 21 Drawing Sheets

(56) References Cited

U.S. PATENT DOCUMENTS

| | | |
|---|---|---|
| 4,899,756 A | 2/1990 | Sonek |
| 4,911,173 A | 3/1990 | Terwillige |
| 4,945,305 A | 7/1990 | Blood |
| 5,076,279 A | 12/1991 | Arenson et al. |
| 5,078,140 A | 1/1992 | Kwoh |
| 5,078,142 A | 1/1992 | Siczek et al. |
| 5,095,910 A | 3/1992 | Powers |
| 5,109,276 A | 4/1992 | Nudelman et al. |
| 5,158,088 A | 10/1992 | Nelson et al. |
| 5,161,536 A | 11/1992 | Vilkomerson et al. |
| 5,193,120 A | 3/1993 | Gamache et al. |
| 5,209,235 A | 5/1993 | Brisken et al. |
| 5,249,581 A | 10/1993 | Horbal et al. |
| 5,251,127 A | 10/1993 | Raab |
| 5,261,404 A | 11/1993 | Mick et al. |
| 5,265,610 A | 11/1993 | Darrow et al. |
| 5,271,400 A | 12/1993 | Dumoulin et al. |
| 5,307,153 A | 4/1994 | Maruyama et al. |
| 5,309,913 A | 5/1994 | Kormos et al. |
| 5,323,002 A | 6/1994 | Sampsell et al. |
| 5,371,543 A | 12/1994 | Anderson |
| 5,383,454 A | 1/1995 | Bucholz |
| 5,394,875 A | 3/1995 | Lewis et al. |
| 5,411,026 A | 5/1995 | Carol |
| 5,433,198 A | 7/1995 | Desai |
| 5,433,739 A | 7/1995 | Sluijter et al. |
| 5,443,489 A | 8/1995 | Ben-Haim |
| 5,446,798 A | 8/1995 | Morita et al. |
| 5,447,154 A | 9/1995 | Cinquin et al. |
| 5,452,024 A | 9/1995 | Sampsell |
| 5,457,493 A | 10/1995 | Leddy et al. |
| 5,474,073 A | 12/1995 | Schwartz et al. |
| 5,476,096 A | 12/1995 | Olstad et al. |
| 5,483,961 A | 1/1996 | Kelly et al. |
| 5,488,431 A | 1/1996 | Gove et al. |
| 5,489,952 A | 2/1996 | Gove et al. |
| 5,491,510 A | 2/1996 | Gove |
| 5,494,039 A | 2/1996 | Onik et al. |
| 5,503,152 A | 4/1996 | Oakley et al. |
| 5,505,204 A | 4/1996 | Picot et al. |
| 5,515,856 A | 5/1996 | Olstad et al. |
| 5,517,990 A | 5/1996 | Kalfas et al. |
| 5,526,051 A | 6/1996 | Gove et al. |
| 5,526,812 A | 6/1996 | Dumoulin et al. |
| 5,529,070 A | 6/1996 | Augustine et al. |
| 5,531,227 A | 7/1996 | Schneider |
| 5,532,997 A | 7/1996 | Pauli |
| 5,541,723 A | 7/1996 | Tanaka |
| 5,558,091 A | 9/1996 | Acker et al. |
| 5,568,811 A | 10/1996 | Olstad |
| 5,570,135 A | 10/1996 | Gove et al. |
| 5,579,026 A | 11/1996 | Tabata |
| 5,588,948 A | 12/1996 | Takahashi et al. |
| 5,608,468 A | 3/1997 | Gove et al. |
| 5,608,849 A | 3/1997 | King, Jr. |
| 5,611,345 A | 3/1997 | Hibbeln |
| 5,611,353 A | 3/1997 | Dance et al. |
| 5,612,753 A | 3/1997 | Poradish et al. |
| 5,625,408 A | 4/1997 | Matsugu et al. |
| 5,628,327 A | 5/1997 | Unger et al. |
| 5,629,794 A | 5/1997 | Magel et al. |
| 5,630,027 A | 5/1997 | Venkateswar et al. |
| 5,647,361 A | 7/1997 | Damadian |
| 5,647,373 A | 7/1997 | Paltieli |
| 5,660,185 A | 8/1997 | Shmulewitz et al. |
| 5,662,111 A | 9/1997 | Cosman |
| 5,699,444 A | 12/1997 | Palm |
| 5,701,898 A | 12/1997 | Adam et al. |
| 5,701,900 A | 12/1997 | Shehada et al. |
| 5,726,670 A | 3/1998 | Tabata et al. |
| 5,728,044 A | 3/1998 | Shan |
| 5,758,650 A | 6/1998 | Miller et al. |
| 5,766,135 A | 6/1998 | Terwilliger |
| 5,784,098 A | 7/1998 | Shoji et al. |
| 5,792,147 A | 8/1998 | Evans et al. |
| 5,793,701 A | 8/1998 | Wright et al. |
| 5,797,849 A | 8/1998 | Vesely et al. |
| 5,807,395 A | 9/1998 | Mulier et al. |
| 5,810,008 A | 9/1998 | Dekel et al. |
| 5,817,022 A | 10/1998 | Vesely |
| 5,820,554 A | 10/1998 | Davis et al. |
| 5,820,561 A | 10/1998 | Olstad et al. |
| 5,829,439 A | 11/1998 | Yokosawa et al. |
| 5,829,444 A | 11/1998 | Ferre et al. |
| 5,851,183 A | 12/1998 | Bucholz |
| 5,870,136 A | 2/1999 | Fuchs et al. |
| 5,891,034 A | 4/1999 | Bucholz |
| 5,920,395 A | 7/1999 | Schulz |
| 5,961,527 A | 10/1999 | Whitmore, III et al. |
| 5,967,980 A | 10/1999 | Ferre et al. |
| 6,016,439 A | 1/2000 | Acker |
| 6,019,724 A | 2/2000 | Gronningsaeter et al. |
| 6,048,312 A | 4/2000 | Ishrak et al. |
| 6,064,749 A | 5/2000 | Hirota et al. |
| 6,095,982 A | 8/2000 | Richards-Kortum et al. |
| 6,099,471 A | 8/2000 | Torp et al. |
| 6,108,130 A | 8/2000 | Raj |
| 6,122,538 A | 9/2000 | Sliwa, Jr. et al. |
| 6,122,541 A | 9/2000 | Cosman et al. |
| 6,167,296 A | 12/2000 | Shahidi |
| RE37,088 E | 3/2001 | Olstad et al. |
| 6,216,029 B1 | 4/2001 | Paltieli |
| 6,241,725 B1 | 6/2001 | Cosman |
| 6,245,017 B1 | 6/2001 | Hashimoto et al. |
| 6,246,898 B1 | 6/2001 | Vesely et al. |
| 6,248,101 B1 | 6/2001 | Whitmore, III et al. |
| 6,261,234 B1 | 7/2001 | Lin |
| 6,341,016 B1 | 1/2002 | Malione |
| 6,348,058 B1 | 2/2002 | Melken et al. |
| 6,350,238 B1 | 2/2002 | Olstad et al. |
| 6,352,507 B1 | 3/2002 | Torp et al. |
| 6,379,302 B1 | 4/2002 | Kessman et al. |
| 6,385,475 B1 | 5/2002 | Cinquin et al. |
| 6,442,417 B1 | 8/2002 | Shahidi et al. |
| 6,447,450 B1 | 9/2002 | Olstad |
| 6,456,868 B2 | 9/2002 | Saito et al. |
| 6,470,207 B1 | 10/2002 | Simon et al. |
| 6,471,366 B1 | 10/2002 | Hughson et al. |
| 6,477,400 B1 | 11/2002 | Barrick |
| 6,478,793 B1 | 11/2002 | Cosman et al. |
| 6,503,195 B1 | 1/2003 | Keller et al. |
| 6,511,418 B2 | 1/2003 | Shahidi et al. |
| 6,517,485 B2 | 2/2003 | Torp et al. |
| 6,518,939 B1 | 2/2003 | Kikuchi |
| 6,527,443 B1 | 3/2003 | Vilsmeier |
| 6,529,758 B2 | 3/2003 | Shahidi |
| 6,537,217 B1 | 3/2003 | Bjærum et al. |
| 6,545,706 B1 | 4/2003 | Edwards et al. |
| 6,546,279 B1 | 4/2003 | Bova et al. |
| 6,551,325 B2 | 4/2003 | Neubauer et al. |
| 6,570,566 B1 | 5/2003 | Yoshigahara |
| 6,579,240 B2 | 6/2003 | Bjaerum et al. |
| 6,587,711 B1 | 7/2003 | Alfano et al. |
| 6,591,130 B2 | 7/2003 | Shahidi |
| 6,592,522 B2 | 7/2003 | Bjaerum et al. |
| 6,594,517 B1 | 7/2003 | Nevo |
| 6,597,818 B2 | 7/2003 | Kumar et al. |
| 6,604,404 B2 | 8/2003 | Paltieli et al. |
| 6,616,610 B2 | 9/2003 | Steininger et al. |
| 6,626,832 B1 | 9/2003 | Paltieli et al. |
| 6,652,462 B2 | 11/2003 | Bjaerum et al. |
| 6,669,635 B2 | 12/2003 | Kessman et al. |
| 6,676,599 B2 | 1/2004 | Torp et al. |
| 6,689,067 B2 | 2/2004 | Sauer et al. |
| 6,695,786 B2 | 2/2004 | Wang et al. |
| 6,711,429 B1 | 3/2004 | Gilboa et al. |
| 6,725,082 B2 | 4/2004 | Sati et al. |
| 6,733,458 B1 | 5/2004 | Steins et al. |
| 6,764,449 B2 | 7/2004 | Lee et al. |
| 6,766,184 B2 | 7/2004 | Utzinger et al. |
| 6,768,496 B2 | 7/2004 | Bieger et al. |
| 6,775,404 B1 | 8/2004 | Pagoulatos et al. |
| 6,782,287 B2 | 8/2004 | Grzeszczuk et al. |
| 6,783,524 B2 | 8/2004 | Anderson et al. |

(56) References Cited

U.S. PATENT DOCUMENTS

| | | |
|---|---|---|
| 6,827,723 B2 | 12/2004 | Carson |
| 6,863,655 B2 | 3/2005 | Bjaerum et al. |
| 6,873,867 B2 | 3/2005 | Vilsmeier |
| 6,875,179 B2 | 4/2005 | Ferguson et al. |
| 6,881,214 B2 | 4/2005 | Cosman et al. |
| 6,895,268 B1 | 5/2005 | Rahn et al. |
| 6,915,150 B2 | 7/2005 | Cinquin et al. |
| 6,917,827 B2 | 7/2005 | Kienzle, III |
| 6,923,817 B2 | 8/2005 | Carson et al. |
| 6,936,048 B2 | 8/2005 | Hurst |
| 6,947,783 B2 | 9/2005 | Immerz |
| 6,968,224 B2 | 11/2005 | Kessman et al. |
| 6,978,167 B2 | 12/2005 | Dekel et al. |
| 7,008,373 B2 | 3/2006 | Stoianovici et al. |
| 7,033,360 B2 | 4/2006 | Cinquin et al. |
| 7,072,707 B2 | 7/2006 | Galloway, Jr. et al. |
| 7,077,807 B2 | 7/2006 | Torp et al. |
| 7,093,012 B2 | 8/2006 | Olstad et al. |
| 7,110,013 B2 | 9/2006 | Ebersole et al. |
| 7,209,776 B2 | 4/2007 | Leitner |
| 7,245,746 B2 | 7/2007 | Bjaerum et al. |
| 7,248,232 B1 | 7/2007 | Yamazaki et al. |
| 7,261,694 B2 | 8/2007 | Torp et al. |
| 7,313,430 B2 | 12/2007 | Urquhart et al. |
| 7,331,932 B2 | 2/2008 | Leitner |
| 7,351,205 B2 | 4/2008 | Szczech et al. |
| 7,379,769 B2 | 5/2008 | Piron et al. |
| 7,385,708 B2 | 6/2008 | Ackerman et al. |
| 7,392,076 B2 | 6/2008 | Moctezuma de La Barrera |
| 7,398,116 B2 | 7/2008 | Edwards |
| 7,466,303 B2 | 12/2008 | Yi et al. |
| 7,480,533 B2 | 1/2009 | Cosman et al. |
| 7,505,809 B2 | 3/2009 | Strommer et al. |
| 7,588,541 B2 | 9/2009 | Floyd et al. |
| 7,662,128 B2 | 2/2010 | Salcudean et al. |
| 7,678,052 B2 | 3/2010 | Torp et al. |
| 7,728,868 B2 | 6/2010 | Razzaque et al. |
| 7,798,965 B2 | 9/2010 | Torp et al. |
| 7,833,168 B2 | 11/2010 | Taylor et al. |
| 7,833,221 B2 | 11/2010 | Voegele et al. |
| 7,846,103 B2 | 12/2010 | Cannon, Jr. et al. |
| 7,876,942 B2 | 1/2011 | Gilboa |
| 7,889,905 B2 | 2/2011 | Higgins et al. |
| 7,912,849 B2 | 3/2011 | Ohrn et al. |
| 7,920,909 B2 | 4/2011 | Lyon et al. |
| 7,962,193 B2 | 6/2011 | Edwards et al. |
| 7,976,469 B2 | 7/2011 | Bonde et al. |
| 8,023,712 B2 | 9/2011 | Ikuma et al. |
| 8,038,631 B1 | 10/2011 | Sanghvi et al. |
| 8,041,413 B2 | 10/2011 | Barbagli et al. |
| 8,050,736 B2 | 11/2011 | Piron et al. |
| 8,052,636 B2 | 11/2011 | Moll et al. |
| 8,066,644 B2 | 11/2011 | Sarkar et al. |
| 8,073,528 B2 | 12/2011 | Zhao et al. |
| 8,086,298 B2 | 12/2011 | Whitmore, III et al. |
| 8,135,669 B2 | 3/2012 | Olstad et al. |
| 8,137,281 B2 | 3/2012 | Huang et al. |
| 8,147,408 B2 | 4/2012 | Bunce et al. |
| 8,152,724 B2 | 4/2012 | Ridley et al. |
| 8,216,149 B2 | 7/2012 | Oonuki et al. |
| 8,221,322 B2 | 7/2012 | Wang et al. |
| 8,228,028 B2 | 7/2012 | Schneider |
| 8,257,264 B2 | 9/2012 | Park et al. |
| 8,296,797 B2 | 10/2012 | Olstad et al. |
| 8,340,379 B2 | 12/2012 | Razzaque et al. |
| 8,350,902 B2 | 1/2013 | Razzaque et al. |
| 8,482,606 B2 | 7/2013 | Razzaque et al. |
| 2001/0007919 A1 | 7/2001 | Shahidi |
| 2001/0016804 A1 | 8/2001 | Cunningham et al. |
| 2001/0045979 A1 | 11/2001 | Matsumoto et al. |
| 2002/0010384 A1 | 1/2002 | Shahidi et al. |
| 2002/0032772 A1 | 3/2002 | Olstad et al. |
| 2002/0049375 A1 | 4/2002 | Strommer et al. |
| 2002/0077540 A1 | 6/2002 | Kienzie, III |
| 2002/0077543 A1 | 6/2002 | Grzeszczuk et al. |
| 2002/0135673 A1 | 9/2002 | Favalora et al. |
| 2002/0138008 A1 | 9/2002 | Tsujita et al. |
| 2002/0140814 A1 | 10/2002 | Cohen-Solal et al. |
| 2002/0156375 A1 | 10/2002 | Kessmam et al. |
| 2002/0198451 A1 | 12/2002 | Carson |
| 2003/0040743 A1 | 2/2003 | Cosman et al. |
| 2003/0073901 A1 | 4/2003 | Simon et al. |
| 2003/0135119 A1 | 7/2003 | Lee et al. |
| 2003/0163142 A1 | 8/2003 | Paltieli et al. |
| 2003/0164172 A1 | 9/2003 | Chumas et al. |
| 2003/0231789 A1 | 12/2003 | Willis et al. |
| 2004/0034313 A1 | 2/2004 | Leitner |
| 2004/0078036 A1 | 4/2004 | Keidar |
| 2004/0095507 A1 | 5/2004 | Bishop et al. |
| 2004/0116810 A1 | 6/2004 | Olstad |
| 2004/0147920 A1 | 7/2004 | Keidar |
| 2004/0152970 A1 | 8/2004 | Hunter et al. |
| 2004/0181144 A1 | 9/2004 | Cinquin et al. |
| 2004/0215071 A1 | 10/2004 | Frank et al. |
| 2004/0238732 A1 | 12/2004 | State et al. |
| 2004/0243146 A1 | 12/2004 | Chesbrough et al. |
| 2004/0243148 A1 | 12/2004 | Wasielewski |
| 2004/0249281 A1 | 12/2004 | Olstad |
| 2004/0249282 A1 | 12/2004 | Olstad |
| 2004/0254454 A1 | 12/2004 | Kockro |
| 2005/0010098 A1 | 1/2005 | Frigstad et al. |
| 2005/0085717 A1 | 4/2005 | Shahidi |
| 2005/0085718 A1 | 4/2005 | Shahidi |
| 2005/0090742 A1 | 4/2005 | Mine et al. |
| 2005/0111733 A1 | 5/2005 | Fors et al. |
| 2005/0159641 A1 | 7/2005 | Kanai |
| 2005/0182316 A1 | 8/2005 | Burdette et al. |
| 2005/0192564 A1 | 9/2005 | Cosman et al. |
| 2005/0219552 A1 | 10/2005 | Ackerman et al. |
| 2005/0222574 A1 | 10/2005 | Giordano et al. |
| 2005/0251148 A1 | 11/2005 | Friedrich et al. |
| 2006/0004275 A1 | 1/2006 | Vija et al. |
| 2006/0020204 A1 | 1/2006 | Serra et al. |
| 2006/0036162 A1 | 2/2006 | Shahidi et al. |
| 2006/0052792 A1 | 3/2006 | Boettiger et al. |
| 2006/0058609 A1 | 3/2006 | Olstad |
| 2006/0058610 A1 | 3/2006 | Olstad |
| 2006/0058674 A1 | 3/2006 | Olstad |
| 2006/0058675 A1 | 3/2006 | Olstad |
| 2006/0089625 A1 | 4/2006 | Voegele et al. |
| 2006/0100505 A1 | 5/2006 | Viswanathan |
| 2006/0122495 A1 | 6/2006 | Kienzle, III |
| 2006/0184040 A1 | 8/2006 | Keller et al. |
| 2006/0193504 A1 | 8/2006 | Salgo et al. |
| 2006/0229594 A1 | 10/2006 | Francischelli et al. |
| 2006/0235290 A1 | 10/2006 | Gabriel et al. |
| 2006/0235538 A1 | 10/2006 | Rochetin et al. |
| 2006/0241450 A1 | 10/2006 | Da Silva et al. |
| 2006/0253030 A1 | 11/2006 | Altmann et al. |
| 2006/0253032 A1 | 11/2006 | Altmann et al. |
| 2006/0271056 A1 | 11/2006 | Terrill-Grisoni et al. |
| 2006/0282023 A1 | 12/2006 | Leitner |
| 2006/0293643 A1 | 12/2006 | Wallace et al. |
| 2007/0016035 A1 | 1/2007 | Hashimoto |
| 2007/0032906 A1 | 2/2007 | Sutherland et al. |
| 2007/0073155 A1 | 3/2007 | Park et al. |
| 2007/0073455 A1 | 3/2007 | Oyobe et al. |
| 2007/0078346 A1 | 4/2007 | Park et al. |
| 2007/0167699 A1 | 7/2007 | Lathuiliere et al. |
| 2007/0167701 A1 | 7/2007 | Sherman |
| 2007/0167705 A1 | 7/2007 | Chiang et al. |
| 2007/0167771 A1 | 7/2007 | Olstad |
| 2007/0167801 A1 | 7/2007 | Webler et al. |
| 2007/0225553 A1 | 9/2007 | Shahidi |
| 2007/0239281 A1 | 10/2007 | Gotte et al. |
| 2007/0244488 A1 | 10/2007 | Metzger et al. |
| 2007/0255136 A1 | 11/2007 | Kristofferson et al. |
| 2007/0270718 A1 | 11/2007 | Rochetin et al. |
| 2007/0276234 A1 | 11/2007 | Shahidi |
| 2008/0004481 A1 | 1/2008 | Bax et al. |
| 2008/0004516 A1 | 1/2008 | DiSilvestro et al. |
| 2008/0030578 A1 | 2/2008 | Razzaque et al. |
| 2008/0039723 A1 | 2/2008 | Suri et al. |
| 2008/0051910 A1 | 2/2008 | Kammerzell et al. |

(56) References Cited

U.S. PATENT DOCUMENTS

| | | |
|---|---|---|
| 2008/0091106 A1 | 4/2008 | Kim et al. |
| 2008/0114235 A1 | 5/2008 | Unal et al. |
| 2008/0161824 A1 | 7/2008 | McMillen |
| 2008/0200794 A1 | 8/2008 | Teichman et al. |
| 2008/0208031 A1 | 8/2008 | Kurpad et al. |
| 2008/0208081 A1 | 8/2008 | Murphy et al. |
| 2008/0214932 A1 | 9/2008 | Mollard et al. |
| 2008/0232679 A1 | 9/2008 | Hahn et al. |
| 2008/0287805 A1 | 11/2008 | Li |
| 2009/0024030 A1 | 1/2009 | Lachaine et al. |
| 2009/0118724 A1 | 5/2009 | Zvuloni et al. |
| 2009/0137907 A1 | 5/2009 | Takimoto et al. |
| 2009/0226069 A1 | 9/2009 | Razzaque et al. |
| 2009/0234369 A1 | 9/2009 | Bax et al. |
| 2009/0312629 A1 | 12/2009 | Razzaque et al. |
| 2010/0045783 A1 | 2/2010 | State et al. |
| 2010/0198045 A1 | 8/2010 | Razzaque et al. |
| 2010/0208963 A1 | 8/2010 | Kruecker et al. |
| 2010/0268067 A1 | 10/2010 | Razzaque et al. |
| 2010/0268072 A1 | 10/2010 | Hall et al. |
| 2010/0268085 A1 | 10/2010 | Kruecker et al. |
| 2010/0305448 A1 | 12/2010 | Dagonneau et al. |
| 2010/0312121 A1 | 12/2010 | Guan |
| 2011/0043612 A1 | 2/2011 | Keller et al. |
| 2011/0046483 A1 | 2/2011 | Fuchs et al. |
| 2011/0057930 A1 | 3/2011 | Keller |
| 2011/0082351 A1 | 4/2011 | Razzaque et al. |
| 2011/0130641 A1 | 6/2011 | Razzaque et al. |
| 2011/0137156 A1 | 6/2011 | Razzaque et al. |
| 2011/0201915 A1 | 8/2011 | Gogin et al. |
| 2011/0201976 A1 | 8/2011 | Sanghvi et al. |
| 2011/0237947 A1 | 9/2011 | Boctor et al. |
| 2011/0238043 A1 | 9/2011 | Kleven |
| 2011/0251483 A1 | 10/2011 | Razzaque et al. |
| 2011/0282188 A1 | 11/2011 | Burnside et al. |
| 2011/0288412 A1 | 11/2011 | Deckman et al. |
| 2011/0295108 A1 | 12/2011 | Cox et al. |
| 2011/0301451 A1 | 12/2011 | Rohling |
| 2012/0035473 A1 | 2/2012 | Sanghvi et al. |
| 2012/0059260 A1 | 3/2012 | Robinson |
| 2012/0071759 A1 | 3/2012 | Hagy et al. |
| 2012/0078094 A1 | 3/2012 | Nishina et al. |
| 2012/0101370 A1 | 4/2012 | Razzaque et al. |
| 2012/0108955 A1 | 5/2012 | Razzaque et al. |
| 2012/0143029 A1 | 6/2012 | Silverstein et al. |
| 2012/0143055 A1 | 6/2012 | Ng et al. |
| 2012/0165679 A1 | 6/2012 | Orome et al. |
| 2012/0259210 A1 | 10/2012 | Harhen et al. |
| 2013/0132374 A1 | 5/2013 | Olstad et al. |
| 2013/0151533 A1 | 6/2013 | Udupa et al. |

FOREIGN PATENT DOCUMENTS

| | | |
|---|---|---|
| AU | 1719601 A | 6/2001 |
| AU | 9036301 A | 3/2002 |
| AU | 2003297225 A1 | 7/2004 |
| AU | 2001290363 B2 | 2/2006 |
| BR | 0113882 A | 7/2003 |
| CA | 2420382 C | 4/2011 |
| DE | 69618482 T2 | 8/2002 |
| DE | 60126798 T2 | 10/2007 |
| EP | 0 427 358 | 5/1991 |
| EP | 1955284 | 8/2008 |
| JP | S63-290550 A | 11/1988 |
| JP | H07-116164 A | 5/1995 |
| JP | 2005-058584 | 3/2005 |
| JP | 2005-323669 | 11/2005 |
| JP | 2009-517177 | 4/2009 |
| WO | WO 9605768 | 2/1996 |
| WO | WO 97/15249 | 5/1997 |
| WO | WO 97/17014 | 5/1997 |
| WO | WO 99/26534 | 6/1999 |
| WO | WO 01/039683 | 6/2001 |
| WO | WO 03/032837 | 4/2003 |
| WO | PCT/US2003/17987 | 12/2003 |
| WO | WO 2005/010711 | 2/2005 |
| WO | WO 2007/019216 | 2/2007 |
| WO | WO 2007/067323 A2 | 6/2007 |
| WO | WO 2007/067323 A3 | 9/2007 |
| WO | WO 2008/017051 | 2/2008 |
| WO | WO 2009/094646 | 7/2009 |
| WO | WO 2010/057315 | 5/2010 |
| WO | WO 2010/096419 | 8/2010 |
| WO | WO 2009/063423 | 10/2010 |
| WO | WO 2011/014687 | 2/2011 |
| WO | PCT/US2013/023678 | 2/2013 |

OTHER PUBLICATIONS

"3D Laparoscope Technology," http://www.inneroptic.com/tech_3DL.htm, copyright 2007 InnerOptic Technology, Inc. printed Sep. 19, 2007, 2 pages.

"Cancer Facts & Figures 2004," www.cancer.org/downloads/STT/CAFF_finalPWSecured.pdf, copyright 2004 American Cancer Society, Inc., printed Sep. 19, 2007, 60 pages.

"David Laserscanner <-Latest News <- Institute for Robotics and Process Control <- Te . . . ," http://www/rob.cs.tu-bs.de/en/news/david, printed Sep. 19, 2007, 1 page.

"laser scanned 3d model Final" video, still image of video attached, http://www.youtube.com/watch?v+DaLgIgmoUf8, copyright 2007 YouTube, LLC, printed Sep. 19, 2007, 2 pages.

"Olympus Endoscopic Ultrasound System," www.olympusamerica.com/msg_section/download_brochures/135_b_gfum130.pdf, printed Sep. 20, 2007, 20 pages.

"Point Grey Research Inc.—Imaging Products—Triclops SDK Samples," http://www.ptgrey.com/products/triclopsSDK/samples.asp, copyright 2007 Point Grey Research Inc., printed Sep. 19, 2007, 1 page.

"Robbins, Mike—Computer Vision Research—Stereo Depth Perception," http://www.compumike.com/vision/stereodepth.php, copyright 2007 Michael F. Robbins, printed Sep. 19, 2007, 3 pages.

"Rue, Registered Ultrasound-Endoscope," copyright 2007 InnerOptic Technology, Inc., 2 pages.

Advertisement, "Inspeck 3DC 3D Capturor," Inspeck 3DC 3D Capturor (www.inspeck.com), 1998.

Advertisement, "Virtual 3D High Speed Non-Contact Surface Perception," Virtual 3-D Technologies Corporation (www.virtual3dtech.com)., Dec. 21, 1998.

Advertisements, "Virtuoso," Visual Interface, Inc. (www.visint.com), Dec. 21, 1998.

Akka, "Automatic Software Control of Display Parameters for Stereoscopic Graphics Images," SPIE vol. 1669: Stereoscopic Displays and Applications III, pp. 31-38 (1992).

Ali et al., "Near Infrared Spectroscopy and Imaging to Probe Differences in Water Content in Normal and Cancer Human Prostate Tissues," Technology in Cancer Research & Treatment; Oct. 2004; 3(5):491-497; Adenine Press.

Aylward et al., Analysis of the Parameter Space of a Metric for Registering 3D Vascular Images, in W. Niessen and M. Viergever (Eds.): MICCAI 2001, LNCS 2208, pp. 932-939, 2001.

Aylward et al., Registration and Analysis of Vascular Images, International Journal of Computer Vision 55(2/3), 123-138, 2003.

Aylward, et al., Intra-Operative 3D Ultrasound Augmentation, Proceedings of the IEEE International Symposium on Biomedical Imaging, Washington, Jul. 2002.

Azuma, "A Survey of Augmented Reality," Presence: Teleoperators and Virtual Environments 6, 4:1-48 (Aug. 1997).

Bajura, Michael et al.,, "Merging Virtual Objects with the Real World: Seeing Ultrasound Imagery within the Patient," Computer Graphics, Proceedings of SIGGRAPH 1992, vol. 26(2), pp. 203-210, available from www.cs.unc.edu/~fuchs/publications/MergVirtObjs92.pdf, printed Sep. 20, 2007, 8 pages.

Benavides et al., "Multispectral digital colposcopy for in vivo detection of cervical cancer," Optics Express; May 19, 2003; 11(1 0) Optical Society of America; USA.

Beraldin, J.A. et al., "Optimized Position Sensors for Flying-Spot Active Triangulation Systems," Proceedings of the Fourth International Conference on a 3-D Digital Imaging and Modeling (3DIM),

(56) References Cited

OTHER PUBLICATIONS

Banff, Alberta, Canada, Oct. 6-10, 2003, pp. 334-341, NRC 47083, copyright 2003 National Research Council of Canada, http://iit-iti.nrc-cnrc.gc.ca/iit-publications-iti/docs/NRC-47083.pdf, printed Sep. 19, 2007, 9 pages.

Billinghurst, M. et al., Research Directions in Handheld AR; Int. J. of Virtual Reality 5(2),51-58 (2006).

Bishop, Azuma et al., "Improving Static and Dynamic Registration in an Optical See-Through HMD," Paper Presented at SIGGRAPH '94 Annual Conference in Orlando, FL (1994).

Blais, F., "Review of 20 Years of Range Sensor Development," Journal of Electronic Imaging, 13(1): 231-240, Jan. 2004, NRC 46531, copyright 2004 National Research Council of Canada, http://iit-iti.nrc-cnrc.gc.ca/iit-publications-iti/docs/NRC-46531.pdf, printed Sep. 19, 2007, 14 pages.

Bouguet, Jean-Yves, "Camera Calibration Toolbox for Matlab," www.vision.caltech.edu/bouguetj/calib_doc, printed Sep. 20, 2007, 5 pages.

Cancer Prevention & Early Detection Facts & Figures 2004; National Center for Tobacco-Free Kids; 2004; American Cancer Society; USA.

Cantor et al., "Cost-Effectiveness Analysis of Diagnosis and Management of Cervical Squamous Intraepithelial Lesions," Diagnostic Strategies for SILs; Feb. 1998; 91(2):270-277.

Catalano et al. "Multiphase helical CT findings after percutaneous ablation procedures for hepatocellular carcinoma." Abdom. Imaging, 25(6),2000, pp. 607-614.

Chiriboga et al., "Infrared Spectroscopy of Human Tissue. IV. Detection of Dysplastic and Neoplastic Changes of Human Cervical Tissue Via Infrared Microscopy," Cellular and Molecular Biology; 1998; 44(1): 219-229.

Crawford, David E. et al., "Computer Modeling of Prostate Biopsy: Tumor Size and Location—Not Clinical Significance—Determine Cancer Detection," Journal of Urology, Apr. 1998, vol. 159(4), pp. 1260-1264, 5 pages.

Deering, Michael "High Resolution Virtual Reality." Proceedings of SIGGRAPH '92, Computer Graphics, 26(2), 1992, pp. 195-202.

Depiero et al., "3-D Computer Vision Using Structured Light: Design, Calibration and Implementation Issues," The University of Tennessee, pp. 1-46, (1996).

Dodd, G.D. et al. "Minimally invasive treatment of malignant hepatic tumors: at the threshold of a major breakthrough." Radiographies 20(1),2000, pp. 9-27.

Drascic et al., "Perceptual Issues in Augmented Reality," SPIE vol. 2653: Stereoscopic Displays and Virtual Reality Systems III, pp. 123-134 (Feb. 1996).

Fahey et al., "Meta-analysis of Pap Test Accuracy; American Journal of Epidemiology," 1995 141(7):680-689; The John Hopkins University School of Hygiene and Public Health; USA.

Foxlin et al., "An Inertial Head-Orientation Tracker with Automatic Drift Compensation for Use with HMD's," Proceedings of the 1994 Virtual Reality Software and Technology Conference, Aug. 23-26, 1994, Singapore, pp. 159-173 (1994).

Fronheiser et al., Real-Time 3D Color Doppler for Guidance of Vibrating Interventional Devices, IEEE Ultrasonics Symposium, pp. 149-152 (2004).

Fuchs, Henry et al. "Augmented Reality Visualization for Laparoscopic Surgery," Proceedings of Medical Image Computing and Computer-Assisted Intervention (MICCAI) 1998, pp. 934-943, available from www.cs.unc.edu/—fuchs/publications/AugRealVis_LaparoSurg98.pdf, printed Sep. 20, 2007, 10 pages.

Fuchs, et al.: "Virtual Environments Technology to Aid Needle Biopsies of the Breast," Health Care in the Information Age, Ch. 6, pp. 60-61, Presented in San Diego, Jan. 17-20, 1996, published by IOS Press and Ohmsha Feb. 1996.

Garrett, William F. et al., "Real-Time Incremental Visualization of Dynamic Ultrasound Volumes Using Parallel BSP Trees," Proceedings of IEEE Visualization 1996, pp. 235-240, available from www.cs.unc.edu/~andrei/pubs/1996_VIS_dualBSP_Mac.pdf, printed Sep. 20, 2007, 7 pages.

Georgakoudi et al., "Trimodal spectroscopy for the detection and characterization of cervical precancers in vivo," American Journal of Obstetrics and Gynecology; Mar. 2002; 186(3):374-382; USA.

Herline et al., Surface Registration for Use in Interactive, Image-Guided Liver Surgery, Computer Aided Surgery 5:11-17 (2000).

Holloway, R.; Registration Error Analysis for Augmented Reality; Presence: Teleoperators and Virtual Environments 6(4), 413—432 (1997).

Hornung et al., "Quantitative near-infrared spectroscopy of cervical dysplasia in vivo," Human Reproduction; 1999; 14(11):2908-2916; European Society of Human Reproduction and Embryology.

Howard, M.D., et al.: "An Electronic Device for Needle Placement during Sonographically Guided Percutaneous Intervention", Radiology 2001; 218:905-911.

InnerAim Brochure; 3D Visualization Software for Simpler, Safer, more Precise Aiming, Published no earlier than Apr. 1, 2010.

InVision System Brochure; A "GPS" for Real-Time 3D Needle Visualization & Guidance, Published no earlier than Mar. 1, 2008.

InVision User Manual; Professional Instructions for Use, Published no earlier than Dec. 1, 2008.

Jacobs, Marco C. et al., "Managing Latency in Complex Augmented Reality Systems," ACM SIGGRAPH Proceedings of the Symposium of Interactive 3D Graphics 1997, pp. 49-54, available from www.cs.unc.edu/~us/Latency//ManagingRelativeLatency.html, printed Sep. 20, 2007, 12 pages.

Kanbara et al., "A Stereoscopic Video See-through Augmented Reality System Based on Real-time Vision-Based Registration," Nara Institute of Science and Technology, pp. 1-8 (2000).

Lass, Amir, "Assessment of Ovarian Reserve," Human Reproduction, 2004, vol. 19(3), pp. 467-469, available from http://humrep.oxfordjournals.orgcgi/reprint/19/3/467, printed Sep. 20, 2007, 3 pages.

Lee et al., "Modeling Real Objects Using Video See-Through Augmented Reality," Presence, 11(2):144-157 (Apr. 2002).

Leven et al., DaVinci Canvas: A Telerobotic Surgical System with Integrated, Robot-Assisted, Laparoscopic Ultrasound Capability, in J. Duncan and G. Gerig (Eds.): MICCAI 2005, LNCS 3749, pp. 811-818, 2005.

Levy, et al., An Internet-Connected, Patient Specific, Deformable Brain Atlas Integrated into a Surgical Navigation System, Journal of Digital Imaging, vol. 10, No. 3. Suppl. 1 Aug. 1997: pp. 231-237.

Livingston, Mark A. et al., "Magnetic Tracker Calibration for Improved Augmented Reality Registration," Presence: Teleoperators and Virtual Environments, 1997, vol. 6(5), pp. 532-546, available from www.cs.unc.edu/~andrei/pubs/1997_Presence_calibr.pdf, printed Sep. 20, 2007, 14 pages.

Matsunaga et al., "The Effect of the Ratio Difference of Overlapped Areas of Stereoscopic Images on each Eye in a Teleoperalion," Stereoscopic Displays and Virtual Reality Systems VII, Proceedings of SPIE, 3957:236-243 (2000).

Meehan, Michael et al., "Effect of Latency on Presence in Stressful Virtual Environment," Proceedings of IEEE Virtual Reality 2003, pp. 141-148, available from http://www.cs.unc.edu/~eve/pubs.html, printed Sep. 20, 2007, 9 pages.

Milgram et al., "Adaptation Effects in Stereo due to Online Changes in Camera Configuration," SPIE vol. 1669-13, Stereoscopic Displays and Applications III, pp. 1-12 (1992).

Mtchell et al., "Colposcopy for the Diagnosis of Squamous Intraepithelial lesions: A metaanalysis," Obstetrics and Gynecology; Apr. 1998; 91(4):626-631.

Nakamoto et al., 3D Ultrasound System Using a Magneto-optic Hybrid Tracker for Augmented Reality Visualization in Laparoscopic Liver Surgery, in T. Dohi and R. Kikinis (Eds.): MICCAI 2002, LNCS 2489, pp. 148-155, 2002.

Nordstrom et al., "Identification of Cervical Intraepithelial Neoplasia (CIN) Using UV-Excited Fluorescence and Diffuse-Reflectance Tissue Spectroscopy," Lasers in Surgery and Medicine; 2001; 29; pp. 118-127; Wiley-Liss, Inc.

Ohbuchi et al. "An Incremental Volume Rendering Algorithm for Interactive 3D Ultrasound Imaging", UNC-CH Computer Science Technical Report TR91-003, (1991).

(56) References Cited

OTHER PUBLICATIONS

Ohbuchi et al., "Incremental Volume Reconstruction and Rendering for 3D Ultrasound Imaging," Visualization in Biomedical Computing, SPIE Proceedings, pp. 312-323, (Oct. 13, 1992).
Ohbuchi, "Incremental Acquisition and Visualization of 3D Ultrasound Images," Ph.D. Dissertation, UNC-CH Computer Science Technical Report TR95—023, (1993).
PCT, International Search Report and Written Opinion, re PCT Application No. PCT/US07/75122, mailing date Aug. 20, 2008.
PCT, International Preliminary Report on Patentability, re PCT Application No. PCT/US07/75122, mailing date Mar. 3, 2009.
PCT, International Search Report and Written Opinion, re PCT Application No. PCT/US2010/024378, mailing date Oct. 13, 2010.
PCT, International Search Report and Written Opinion, re PCT Application No. PCT/US2010/043760, mailing date Mar. 3, 2011.
PCT, The International Search Report and Written Opinion of the International Searching Authority, mailed Sep. 9, 2009, for case PCT/US2009/032028.
Pogue, Brian W. et al., "Analysis of acetic acid-induced whitening of high-grade squamous intraepitheliallesions," Journal of Biomedical Optics; Oct. 2001; 6(4):397-403.
Raij, A.B., et al., Comparing Interpersonal Interactions with a Virtual Human to Those with a Real Human; IEEE Transactions on Visualization and Computer Graphics 13(3), 443-457 (2007).
Raz et al, Real-Time Magnetic Resonance Imaging-Guided Focal Laser Therapy in Patients with Low-Risk Prostate Cancer, European Urology 58, pp. 173-177. Mar. 12, 2010.
Robinett et al., "A Computational Model for the Stereoscopic Optics of a Head-Mounted Display," SPIE vol. 1457, Stereoscopic Displays and Applications II, pp. 140-160 (1991).
Rolland et al., Towards Quantifying Depth and Size Perception in Virtual Environments, Presence: Teleoperators and Virtual Environments, Winter 1995, vol. 4, Issue 1, pp. 1-21 and 24-49.
Rosenthal, Michael et al., "Augmented Reality Guidance for Needle Biopsies: An Initial Randomized, Controlled Trial in Phantoms," Proceedings of Medical Image Analysis, Sep. 2002, vol. 6(3), pp. 313-320, available from www.cs.unc.edu/~fuchs/publications/AugRealGuida_NeedleBiop02.pdf, printed Sep. 20, 2007, 8 pages.
Rosenthal, Michael et al., "Augmented Reality Guidance for Needle Biopsies: A Randomized, Controlled Trial in Phantoms," Proceedings of MICCAI 2001, eds. W. Niessen and M. Viergever, Lecture Notes in Computer Science, 2001, vol. 2208, pp. 240-248, available from www.cs.unc.edu/~us/AugmentedRealityAssistance.pdf, printed Sep. 20, 2007, 9 pages.
Splechtna, Fuhrmann A. et al., Comprehensive calibration and registration procedures for augmented reality; Proc. Eurographics Workshop on Virtual Environments 2001,219—228 (2001).
State et al., "Case Study: Observing a Volume Rendered Fetus within a Pregnant Patient," Proceedings of IEEE Visualization 1994, pp. 364-368, available from www.cs.unc.edu/~fuchs/publications/cs-ObservVolRendFetus94.pdf, printed Sep. 20, 2007, 5 pages.
State et al., "Interactive Volume Visualization on a Heterogenous Message-Passing Multicomputer," Proceedings of 1995 Symposium on Interactive 3D Graphics, 1995, pp. 69-74, 208, available from www.cs.unc.edu/~andrei/pubs/1995_I3D_vol2_Mac.pdf, printed Sep. 20, 2007.
State et al., "Simulation-Based Design and Rapid Prototyping of a Parallax-Free, Orthoscopic Video See-Through Head-Mounted Display," Proceedings of International Symposium on Mixed and Augmented Reality (ISMAR) 2005, available from www.cs.unc.edu/~andrei/pubs/2005_ISMAR_VSTHMD_design.pdf, printed Sep. 20, 2007, 4 pages.
State et al., "Stereo Imagery from the UNC Augmented Reality System for Breast Biopsy Guidance" Proc. Medicine Meets Virtual Reality (MMVR) 2003 (Newport Beach, CA, Jan. 22-25, 2003).
State et al., "Superior Augmented Reality Registration by Integrating Landmark Tracking and Magnetic Tracking," ACM SIGGRAPH Computer Graphics, Proceedings of SIGGRAPH 1996, pp. 429-438, available from www.cs.princeton.edu/courses/archive/fall01/cs597d/papers/state96.pdf, printed Sep. 20, 20007, 10 pages.
State et al., "Technologies for Augmented Reality Systems: Realizing Ultrasound-Guided Needle Biopsies," Computer Graphics, Proceedings of SIGGRAPH 1996, pp. 429-438, available from www.cs.princeton.edu/courses/archive/fall101/cs597d/papers/state96.pdf, printed Sep. 20, 2007.
State, Andrei "Exact Eye Contact with Virtual Humans." Proc. IEEE International Workshop on Human Computer Interaction 2007 (Rio de Janeiro, Brazil, Oct. 20, 2007), pp. 138-145.
Takagi et al., "Development of a Stereo Video See-through HMD for AR Systems," IEEE, pp. 68-77 (2000).
Ultraguide 1000 System, Ultraguide, www.ultraguideinc.com, 1998.
Van Staveren et al., "Light Scattering in Intralipid-10% in the wavelength range of 400-1100 nm," Applied Optics; Nov. 1991; 30(31):4507-4514.
Viola et al., "Alignment by Maximization of Mutual Information," International Journal of Computer Vision, vol. 24, No. 2, pp. 1-29 (1997).
Viola, Paul A., Alignment by Maximization of Mutual Information, Ph.D. Dissertation, MIT—Artificial Intelligence Laboratory Technical Report No. 1548 (Jun. 1995).
Ware et al., "Dynamic Adjustment of Stereo Display Parameters," IEEE Transactions on Systems, Many and Cybernetics, 28(1):1-19 (1998).
Watson et al., "Using Texture Maps to Correct for Optical Distortion in Head-Mounted Displays," Proceedings of the Virtual Reality Annual Symposium '95, IEEE, pp. 1-7 (1995).
Welch, Hybrid Self-Tracker: An Inertial/Optical Hybrid Three-Dimensional Tracking System, University of North Carolina Chapel Hill Department of Computer Science, TR 95-048 (1995).
Yinghui et al., Real-Time Deformation Using Modal Analysis on Graphics Hardware, Graphite 2006, Kuala Lumpur, Malaysia, Nov. 29-Dec. 2, 2006.
Zitnick et al., "Multi-Base Stereo Using Surface Extraction," Visual Interface Inc., (Nov. 24, 1996).
Bajura, Michael et al.,, "Merging Virtual Objects with the Real World: Seeing Ultrasound Imagery within the Patient," Computer Graphics, Proceedings of SIGGRAPH 1992, vol. 26(2), pp. 203-210, available from www.cs.unc.edu/~fuchs/publications/MergVirtObjs92.pdf, printed Sep. 20, 2007, 8 pages.
Buxton et al.; "Colposcopically directed punch biopsy: a potentially misleading investigation," British Journal of Obstetrics and Gynecology; Dec. 1991; 98:1273-1276.
Caines, Judy S. et al. Stereotaxic Needle Core Biopsy of Breast Lesions Using a Regular Mammographic Table with an Adaptable Stereotaxic Device, American Journal of Roentgenology, vol. 163, No. 2, Aug. 1994, pp. 317-321. Downloaded from www.ajrorline.org on Jul. 10, 2013.
Dumoulin, C.L. et al, Real-Time Position Monitoring of Invasive Devices Using Magnetic Resonance, Magnetic Resonance in Medicine, vol. 29, Issue 3, Mar. 1993, pp. 411-415.
Jolesz, Ferenc A, M.D., et al. MRI-Guided Laser-Induced Interstitial Thermotherapy: Basic Principles, SPIE Institute on Laser-Induced Interstitial Thermotherapy (L1TT), Jun. 22-23, 1995, Berlin, Germany.
Kadi, A Majeed, et al., Design and Simulation of an Articulated Surgical Arm for Guidling Sterotactic Neurosurgery, SPIE vol. 1708 Applications of Artificial Intelligence X: Machine Vision and Robotics (1992). Downloaded from: http://proceedings.spiedigitallibrary.org/ on Jul. 11, 2013.
Kato, Amami, et al., A frameless, armless navigational system for computer-assisted neurosurgery, Journal of Neurosurgery, vol. 74, No. 5, May 1991, pp. 845-849.
PCT International Search Report and Written Opinion, re PCT Application No. PCT/US2013/023678, mailed Jun. 13, 2013.
Screenshots from video produced by the University of North Carolina, produced circa 1992.
State et al., Contextually Enhanced 3D Visualization for Multi-burn Tumor Ablation Guidance, Departments of Computer Science and Radiology,and School of Medicine, University of North Carolina at Chapel Hill; InnerOptic Technology, Inc., 2008, Chapel Hill, NC, pp. 70-77.
Fuchs, et al., Optimizing a Head-Tracked Stereo Display System to Guide Hepatic Tumor Ablation, Departments of Computer Science and Radiology,and School of Medicine, University of North Carolina at Chapel Hill; InnerOptic Technology, Inc., 2008, Chapel Hill, NC.

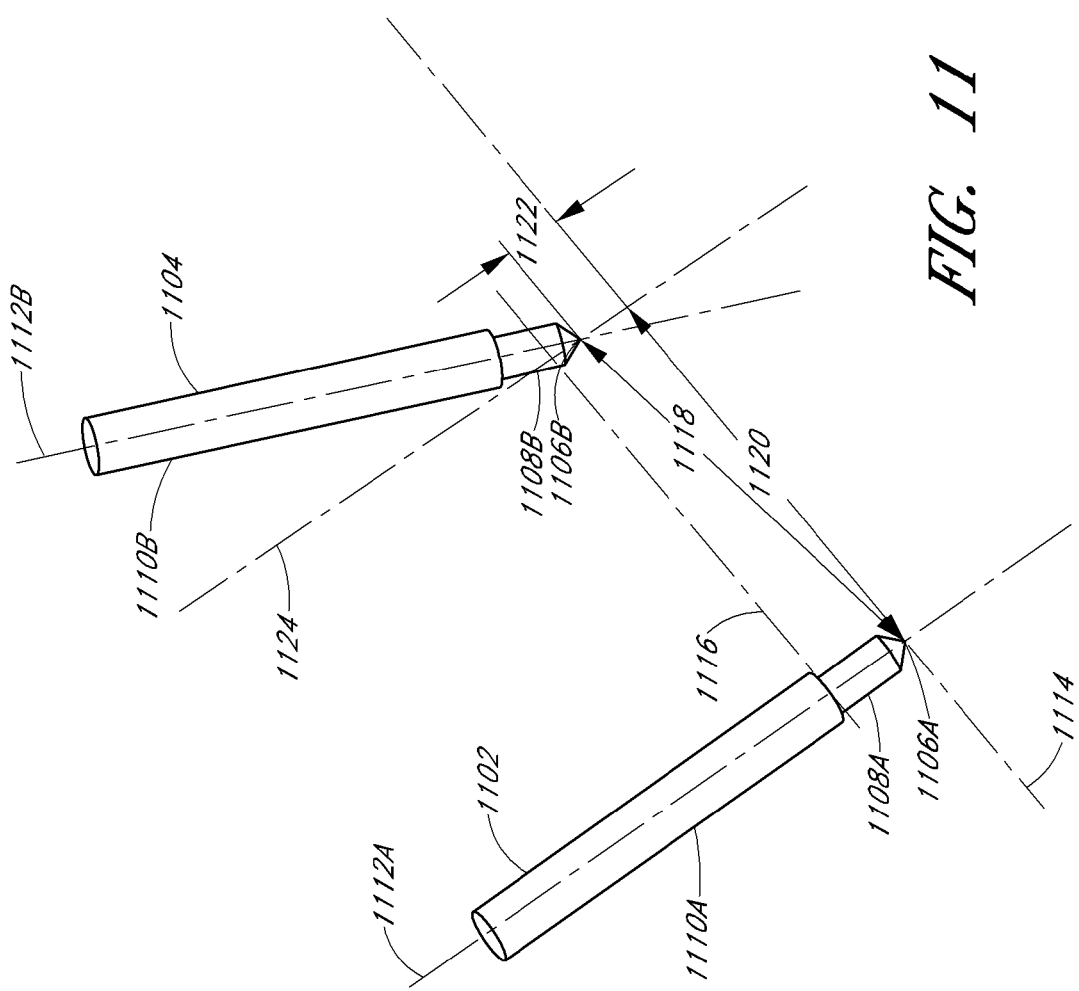

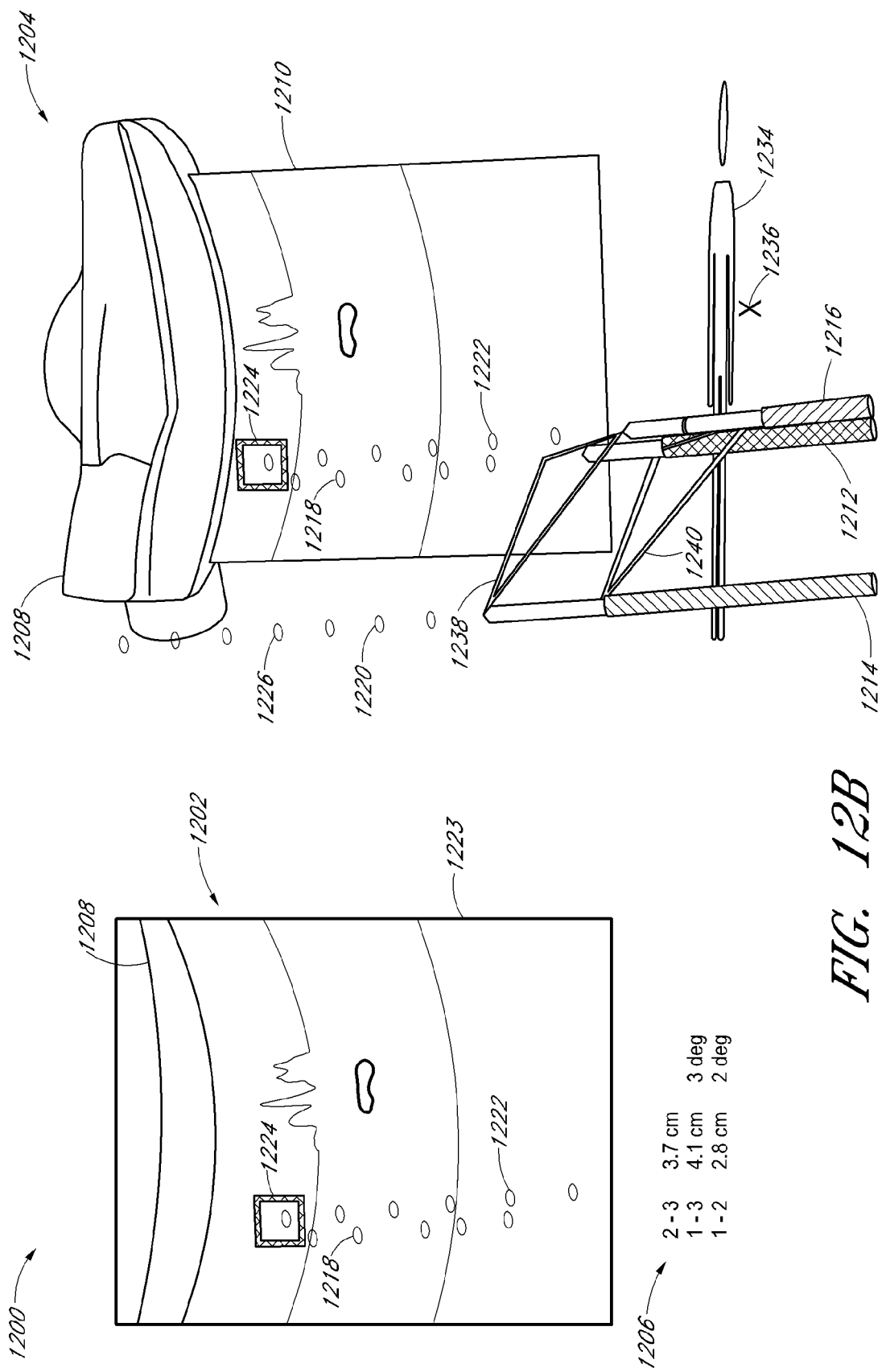

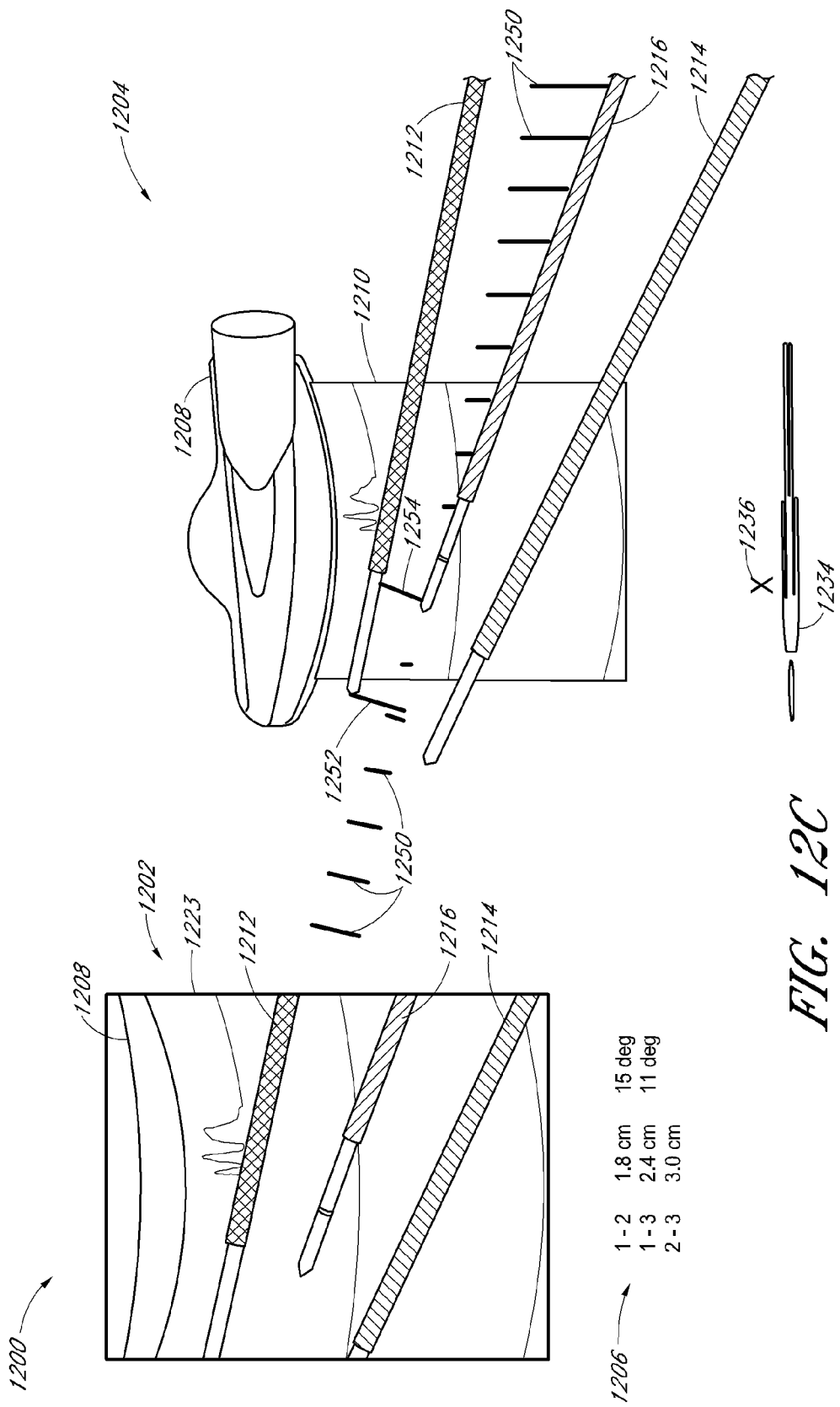

MULTIPLE MEDICAL DEVICE GUIDANCE

CROSS-REFERENCE TO RELATED APPLICATIONS

The present application claims priority benefit to U.S. Provisional Application Nos. 61/592,531, filed Jan. 30, 2012 and 61/736,789 filed Dec. 13, 2012, each of which is hereby incorporated herein by reference in its entirety.

TECHNICAL FIELD

The systems and methods disclosed herein relate generally to computer systems facilitating medical device guidance through tissue by a medical practitioner.

BACKGROUND

Various existing medical device systems, such as for ablation procedures, require a healthcare provider, such as a physician, to place controlled formations of medical devices into patient tissue. Examples of these systems include the RFA Medical InCircle™ System and the AngioDynamics NanoKnife™ system. Similarly, the Covidien Evident™ MWA System does not require, but supports, multi-medical device configurations. Many of these systems include a plastic guide piece to help the healthcare provider hold the medical devices in an acceptable spatial configuration (e.g. three medical devices held parallel, with shafts 2 cm apart).

Unfortunately, controlled placement of the medical devices often comes at the expense of operator flexibility and responsiveness. Accordingly, there is a need for a medical device guidance system which assists operators in placing medical devices, while permitting the operator to maintain an appropriate degree of hand flexibility.

BRIEF DESCRIPTION OF THE DRAWINGS

FIG. 11 is a diagram illustrating various features of multiple medical devices that can be tracked by the system.

FIGS. 12A-12D illustrate embodiments of displaying image guidance data for multiple medical devices.

DETAILED DESCRIPTION

System Overview

Figure 1A:
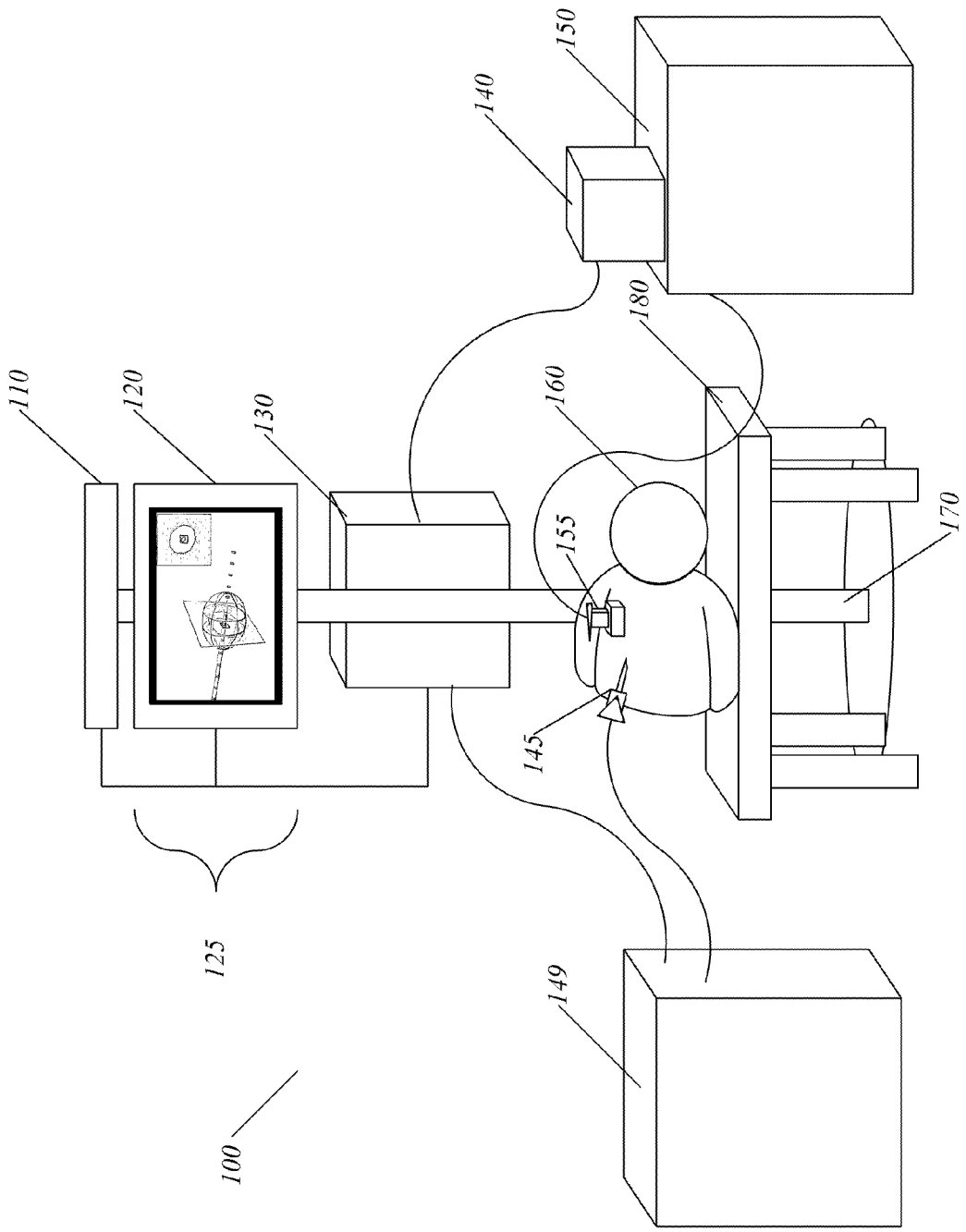
FIG. 1A illustrates a first exemplary system for image-guided medical procedures.

Implementations disclosed herein provide systems, methods and apparatus for generating images facilitating medical device insertion into tissue by an operator. Certain embodiments pertain to a free-hand medical device guidance system. The system can provide the healthcare provider full manual control over the medical device, while making the spatial relationships between the target, medical device and U/S image more intuitive via a visual display. Using this visual feedback, the operator can adjust the medical device's position, orientation, or trajectory. Particularly, the system can be used to facilitate multiple-medical device configurations. Certain of the contemplated embodiments can be used in conjunction with previous systems, such as U.S. patent application Ser. No. 13/014,587 and U.S. patent application Ser. No. 11/137,156, each of which is hereby incorporated by reference in its entirety.

In some embodiments, a user desires that the medical devices that are used together (e.g., used simultaneously for treating one tumor) are parallel to each other. In certain embodiments, the medical devices are arranged to be equally spaced from the center of the tumor. In some embodiments, a user desires that the tips of the medical devices be in the same plane, and all medical device shafts be perpendicular to that plane. In some embodiments, each medical device includes a single shaft-like electrode surrounded by a tube of electrically insulating material. The medical provider can expose some length of the electrode by sliding the insulating tube partially into the medical device's handle. In some embodiments, the length of the exposed electrode can be specified by the user (e.g. 0.5 cm-2 cm). In some embodiments, the length of the exposed electrodes can be the same for all medical devices. In certain embodiments, the healthcare provider exposes the electrode (by withdrawing the insulating sleeve) before placing the medical device into the patient. In some embodiments, the power generator is provided the distances between the medical devices, and the length of the exposed electrodes. In some embodiments, the medical devices can move continuously, even after the healthcare provider has placed them into the proper position in the patient's tissue because of patient motion from breathing, manual manipulation, etc. In some embodiments, the medical devices are not parallel to an image plane.

The system can aid the healthcare provider in placing the medical devices. In some embodiments, the system improves the healthcare provider's ability to place the medical devices level with each other (e.g., tips are co-planar) and parallel with each other. The system can also aid the healthcare provider in determining the number of medical devices to be used and what their optimal positions are, including: distance from tumor's center; distance from tumor's extent or boundary; medical device depth; spacing between medical devices; angle between medical devices; exposure of the deployable electrodes (or optimal retraction of the electrode's insulation), etc.

The system can also help the healthcare provider determine what healthy tissues are in an ablation zone volume (by displaying the predicted ablation zone of the multi-medical device configuration). The system can help the healthcare provider place the medical devices in the above determined (planned) configuration. The system can help the healthcare provider understand how the current configuration (i.e. the way the medical devices are currently placed) differs from the optimal, acceptable or pre-planned configurations. The system can output the distance between medical devices to the power generator, so that the ablation time, the ablation power and other ablation parameters can be automatically computed by the ablation generator. The system can be used for treatment of tumors, fibroids or cysts, with bipolar radiofrequency medical device ablation, multiple microwave medical devices, electroporation, and/or electrochemotherapy systems. It can also be used for nerve or muscle stimulation or sensing (electrodes in the spine, brain). The system can be used during open surgery, laparoscopic surgery, endoscopic procedures, biopsies, and/or interventional radiology procedures.

The system can be used in conjunction with live intraoperative ultrasound (U/S), pre-operative CT, or any cross-sectional medical imaging modality (e.g. MRI, OCT, etc.). In addition, the system can use a variety of techniques to determine each medical device's position and orientation. For example, the system can use the NDI Aurora magnetic system, NDI Polaris optical system, etc. In some embodiments, a position sensor can be embedded inside, or affixed to the outside of each medical device, at the tip, along the shaft, or on the handle. Sensors can be built into the medical devices or attached after manufacturing, before use. Each medical device can have its own sensor, which continually reports position and orientation, or a single sensor can be used for all the medical devices. In embodiments where one sensor is used, the healthcare provider can attach the sensor to the particular medical device that she is intentionally repositioning, and then, once she has placed that medical device, she would remove the sensor and attach it to the next medical device she is repositioning. In some embodiments, the medical devices, U/S probe and/or laparoscope can be manipulated by the healthcare provider. In certain embodiments, the system can be used with a robotic manipulator, where the robot controls the medical devices, U/S probe and/or laparoscope.

Figure 1B:
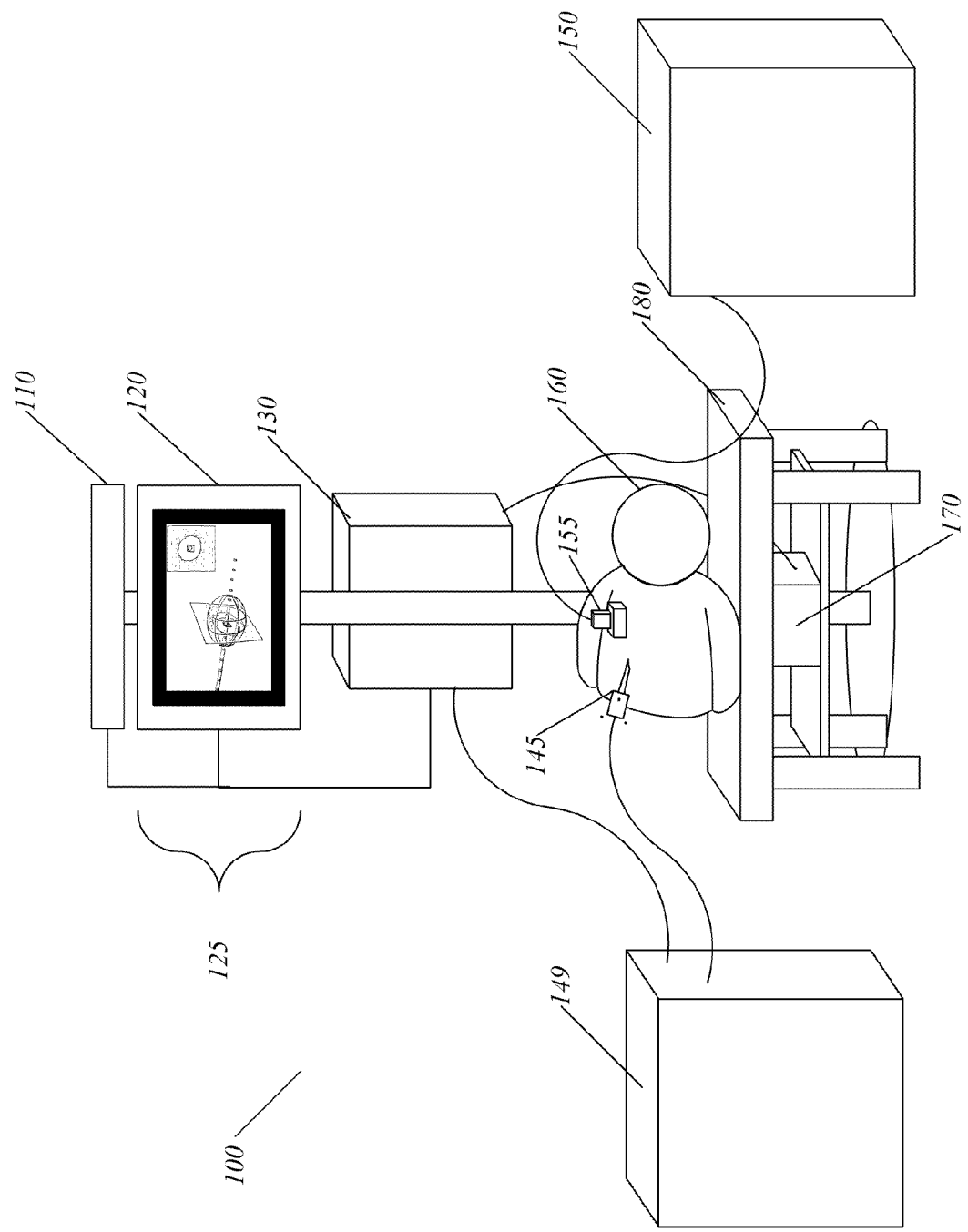
FIG. 1B illustrates a second exemplary system for image-guided medical procedures.

In some embodiments, the handles of medical devices can have push-button switches, to allow the user to select a medical device, indicate a tissue target, etc. The handle can also have an indicator light to indicate to the users which medical device is selected. Finally, the handle can have an encoder to detect how much length of electrode has been exposed by the user, and report this information to the guidance system and therapeutic generator Image Guidance Systems FIG. 1A illustrates a first exemplary system for image management in image-guided medical procedures. FIG. 1B illustrates a second exemplary system for image management in image-guided medical procedures. In many respects the embodiments illustrated by FIGS. 1A and 1B are similar and use similar numbering. Where the two are different, those differences are noted. The differences between the two figures can include that, in FIG. 1A, two position sensing units 110 and 140 are shown, whereas in FIG. 1B, only a single position sensing unit 110 is shown.

In some embodiments, position sensing units 110 and 140 can track surgical instruments, also referred to herein as medical devices, within a tracking area and provide data to the image guidance unit. The medical devices can include invasive medical devices, biopsy needles, ablation needles, surgical needles, nerve-block needles, or other needles, electrocautery device, catheters, stents, laparoscopic cameras, or other instruments that enter a part of the body, and non-invasive medical devices that do not enter the body, such as ultrasound transducers. The medical devices can also include medical imaging devices that provide or aid in the selection of medical images for display. In some embodiments, the medical imaging device can be any device that is used to select a particular medical image for display. The medical imaging devices can include invasive medical devices, such as laparoscopic cameras, and non-invasive medical devices, such as ultrasound transducers.

Although only two surgical instruments 145 and 155 are shown in FIGS. 1A and 1B, it will be understood that additional surgical instruments can be tracked and associated data can be provided to the image guidance unit 130. The image guidance unit 130 can process or combine the data and show image guidance data on display 120. This image guidance data can be used by a healthcare provider to guide a procedure and improve care. There are numerous other possible embodiments of system 100. For example, many of the depicted modules can be joined together to form a single module and can be implemented in a single computer or machine. Further, position sensing units 110 and 140 can be combined and track all relevant surgical instruments 145 and 155, as discussed in more detail below and exemplified in FIG. 1B. Additional imaging units 150 can be included, and combined imaging data from the multiple imaging units 150 can be processed by image guidance unit 130 and shown on display unit 120. Additionally, two or more surgical systems 149 can also be included.

Information about and from multiple surgical systems 149 and attached surgical instruments 145 (and additional surgical instruments not shown) can be processed by image guidance unit 130 and shown on display 120. These and other possible embodiments are discussed in more detail below. Imaging unit 150 can be coupled to image guidance unit 130. In some embodiments, imaging unit 150 can be coupled to a second display unit (not shown). The second display unit can display imaging data from imaging unit 150. The imaging data displayed on display unit 120 and displayed on second display unit can be the same or different. In some embodiments, the imaging unit 150 is an ultrasound machine 150, the movable imaging device 155 is an ultrasound transducer 155 or ultrasound probe 155, and the second display unit is a display associated with the ultrasound machine 150 that displays the ultrasound images from the ultrasound machine 150. In some embodiments, a movable imaging unit 155 can be connected to image guidance unit 130. The movable imaging unit 155 can be useful for allowing a user to indicate what portions of a first set of imaging data are to be displayed. For example, the movable imaging unit 155 can be an ultrasound transducer 155, a needle or other medical device, for example, and can be used by a user to indicate what portions of imaging data, such as a pre-operative CT scan, to show on a display unit 120 as image 125. Further, in some embodiments, there can be a third set of pre-operative imaging data that can be displayed with the first set of imaging data.

In some embodiments, system 100 comprises a first position sensing unit 110, a display unit 120, and second position sensing unit 140 (if it is included) all coupled to image guidance unit 130. In some embodiments, first position sensing unit 110, display unit 120, and image guidance unit 130 are all physically connected to stand 170. Image guidance unit 130 can be used to produce images 125 that are displayed on display unit 120. The images 125 produced on display unit 120 by the image guidance unit 130 can be determined based on ultrasound or other visual images from the first surgical instrument 145 and second surgical instrument 155.

For example, if the first surgical instrument 145 is an ablation needle 145 and the second surgical instrument 155 is an ultrasound probe 155, then images 125 produced on display 120 can include the images, or video, from the ultrasound probe 155 combined with graphics, such as projected medical device drive or projected ablation volume, determined based on the emplacement of ablation needle 145. If the first surgical instrument 145 is an ultrasound probe 145 and the second surgical instrument 155 is a laparoscopic camera 155, then images 125 produced on display 120 can include the video from the laparoscopic camera 155 combined with ultrasound data superimposed on the laparoscopic image. More surgical instruments can be added to the system. For example, the system can include an ultrasound probe, ablation needle, laparoscopic camera, cauterizer, scalpel and/or any other surgical instrument or medical device. The system can also process and/or display collected data, such as preoperative CT scans, X-Rays, MRIs, laser scanned 3D surfaces etc.

The term "emplacement" and the term "pose" as used herein are broad terms encompassing their plain and ordinary meanings and may refer to, without limitation, position, orientation, the combination of position and orientation, or any other appropriate location information. In some embodiments, the imaging data obtained from one or both of surgical instruments 145 and 155 can include other modalities such as a CT scan, MRI, open-magnet MRI, optical coherence tomography ("OCT"), positron emission tomography ("PET") scans, fluoroscopy, ultrasound, or other preoperative, or intraoperative 2D or 3D anatomical imaging data. In some embodiments, surgical instruments 145 and 155 can also be scalpels, implantable hardware, or any other device used in surgery. Any appropriate surgical system 149 or imaging unit 150 can be attached to the corresponding medical instruments 145 and 155.

As noted above, images 125 produced can also be generated based on live, intraoperative, or real-time data obtained using the second surgical instrument 155, which is coupled to second imaging unit 150. The term "real time" as used herein is a broad term and has its ordinary and customary meaning, including without limitation instantaneously or nearly instantaneously. The use of the term real time can also mean that actions are performed or data is obtained with the intention to be used immediately, upon the next cycle of a system or control loop, or any other appropriate meaning. Additionally, as used herein, real-time data can be data that is obtained at a frequency that would allow a healthcare provider to meaningfully interact with the data during surgery. For example, in some embodiments, real-time data can be a medical image of a patient that is updated one time per second. In some embodiments, real-time data can be ultrasound data that is updated multiple times per second.

Second surgical instrument 155 can be coupled to second position sensing unit 140. Second position sensing unit 140 can be part of imaging unit 150 or it can be separate. Second position sensing unit 140 can be used to determine the emplacement of second surgical instrument 155. In some embodiments, first and/or second position sensing units 110 and/or 140 can be magnetic trackers and magnetic can be coils coupled to surgical instruments 145 and/or 155. In some embodiments, first and/or second position sensing units 110 and/or 140 can be optical trackers and visually-detectable fiducials can be coupled to surgical instruments 145 and/or 155.

Images 125 can be produced based on intraoperative or real-time data obtained using first surgical instrument 145, which is coupled to first surgical system 149. In FIGS. 1A and 1B, first surgical system 149 is shown as coupled to image guidance unit 130. The coupling between first surgical system 149 and image guidance unit 130 may not be present in all embodiments. In some embodiments, the coupling between first surgical system 149 and image guidance unit 130 can be included where information about first surgical instrument 145 available to first surgical system 149 is useful for the processing performed by image guidance unit 130. For example, in some embodiments, the first surgical instrument 145 is an ablation needle 145 and first surgical system 149 is an ablation system 149. In some embodiments, it can be useful to send a signal about the relative strength of planned ablation from ablation system 149 to image guidance unit 130 in order that image guidance unit 130 can show a predicted ablation volume. In other embodiments, the first surgical system 149 is not coupled to image guidance unit 130. Example embodiments including images and graphics that can be displayed are included below.

In some embodiments, the first position sensing unit 110 tracks the emplacement of first surgical device 145. First position sensing unit 110 can be an optical tracker 110 and first surgical device 145 can have optical fiducials attached thereto. The emplacement of optical fiducials can be detected by first position sensing unit 110, and, therefrom, the emplacement of first surgical device 145 can be determined.

In various embodiments, as depicted in FIG. 1B, a single position sensing unit 110 can track both first medical device 145 and second medical device 155. In FIG. 1B, in some embodiments, position sensing unit 110 is a magnetic tracker and is mounted below a surgical table 180. Such an arrangement can be useful when the tracking volume of the position sensing unit 110 is dependent on the location of the position sensing unit, as with many magnetic trackers. Magnetic tracking coils can be mounted in or on the medical devices 145 and 155.

In some embodiments, either or both of the first position sensing unit 110 and the second position sensing unit 140 can be an Ascension Flock of Birds, Nest of Birds, driveBAY, medSAFE, trakSTAR, miniBIRD, MotionSTAR, pciBIRD, or Calypso 2D Localization System and tracking units attached to the first and/or second medical devices 145 and 155 can be magnetic tracking coils. The term "tracking unit," as used herein, is a broad term encompassing its plain and ordinary meaning and includes without limitation all types of magnetic coils or other magnetic field sensing devices for use with magnetic trackers, fiducials or other optically detectable markers for use with optical trackers, such as those discussed above and below. In some embodiments, the tracking units can be implemented using optical position sensing devices, such as the HiBall tracking system and the first and second position sensing units 110 and 140 can form part of the HiBall tracking system. Tracking units can also include a GPS device or signal emitting device that allows for tracking of the position and, optionally, orientation of the tracking unit. In some embodiments, a signal emitting device might include a radio-frequency identifier (RFID). In such embodiments, the first and/or second position sensing unit 110 and 140 can use the GPS coordinates of the tracking units or can, for example, triangulate the radio frequency signal being emitted by the RFID associated with tracking units. The tracking systems can also include one or more 3D mice.

In some embodiments, either or both of the first position sensing unit 110 and the second position sensing unit 140 can be an electromagnetic measurement system (e.g., NDI Aurora system) using sensor coils for tracking units attached to the first and/or second surgical devices 145 and 155. In some embodiments, either or both of the first position sensing unit 110 and the second position sensing unit 140 can be an optical 3D tracking system using fiducials. Such optical 3D tracking systems can include the NDI Polaris Spectra, Vicra, Certus, PhaseSpace IMPULSE, Vicon MX, InterSense IS-900, NaturalPoint OptiTrack, Polhemus FastTrak, IsoTrak, or Claron MicronTracker2. In some embodiments, either or both of position sensing units 110 and 140 can each be an inertial 3D tracking system comprising a compass, accelerometer, tilt sensor and/or gyro, such as the InterSense InertiaCube or the Nintendo Wii controller. In some embodiments, either or both of position sensing units 110 and 140 can be attached to or affixed on the corresponding surgical device 145 and 155. In some embodiments, the position sensing units, 110 and 140, can include sensing devices such as the HiBall tracking system, a GPS device, or signal emitting device that would allow for tracking of the position and, optionally, orientation of the tracking unit. In some embodiments, a position sensing unit 110 or 140 can be affixed to either or both of the surgical devices 145 and 155. The surgical devices 145 or 155 can be tracked by the position sensing units 110 or 140. A room coordinate system reference, such as the display 120 can also be tracked by the position sensing unit 110 or 140 in order to determine the emplacements of the surgical devices 145 and 155 with respect to the room coordinate system. Devices 145 and 155 can also include or have coupled thereto one or more accelerometers, which can be used to estimate movement, position, and location of the devices.

In some embodiments, the display unit 120 displays 3D images to a user, such as a healthcare provider. Stereoscopic 3D displays separate the imagery shown to each of the user's eyes. This can be accomplished by a stereoscopic display, a lenticular auto-stereoscopic display, or any other appropriate type of display. The display 120 can be an alternating row or alternating column display. Example alternating row displays include the Miracube G240S, as well as Zalman Trimon Monitors. Alternating column displays include devices manufactured by Sharp, as well as many "auto-stereoscopic" displays (e.g., Philips). Display 120 can also be a cathode ray tube. Cathode Ray Tube (CRT) based devices, can use temporal sequencing, showing imagery for the left and right eye in temporal sequential alternation. This method can also be used projection-based devices, as well as by liquid crystal display (LCD) devices, light emitting diode (LED) devices, and/or organic LED (OLED) devices.

In certain embodiments, a user can wear a head mounted display in order to receive 3D images from the image guidance unit 130. In such embodiments, a separate display, such as the pictured display unit 120, can be omitted. The 3D graphics can be produced using underlying data models, stored in the image guidance unit 130 and projected onto one or more 2D planes in order to create left and right eye images for a head mount, lenticular, or other 3D display. The underlying 3D model can be updated based on the relative emplacements of the various devices 145 and 155, as determined by the position sensing unit(s), and/or based on new data associated with the devices 145 and 155. For example, if the second medical device 155 is an ultrasound probe, then the underlying data model can be updated to reflect the most recent ultrasound image. If the first medical device 145 is an ablation needle, then the underlying model can be updated to reflect any changes related to the needle, such as power or duration information. Any appropriate 3D graphics processing can be used for rendering including processing based on OpenGL, Direct3D, Java 3D, etc. Whole, partial, or modified 3D graphics packages can also be used, such packages including 3DS Max, SolidWorks, Maya, Form Z, Cybermotion 3D, VTK, Slicer, or any others. In some embodiments, various parts of the needed rendering can occur on traditional or specialized graphics hardware. The rendering can also occur on the general CPU, on programmable hardware, on a separate processor, be distributed over multiple processors, over multiple dedicated graphics cards, or using any other appropriate combination of hardware or technique.

One or more modules, units, devices, or elements of various embodiments can be packaged and/or distributed as part of a kit. For example, in one embodiment, an ablation needle, tracking elements, 3D viewing glasses, and/or a portion of an ultrasound wand can form a kit. Other embodiments can have different elements or combinations of elements grouped and/or packaged together. Kits can be sold or distributed separately from or with the other portions of the system.

One will readily recognize that there are numerous other examples of image guidance systems which can use, incorporate, support, or provide for the techniques, methods, processes, and systems described herein.

Depicting Surgical Instruments

Previous systems do not provide satisfactory image guidance data. It can often be difficult to discern the content of a 3D scene from a 2D depiction of it, or even from a 3D depiction of it. Therefore, various embodiments herein provide image guidance that can help the doctor better understand the scene, relative emplacements or poses of object in the scene and thereby provide improved image guidance.

Figure 2:
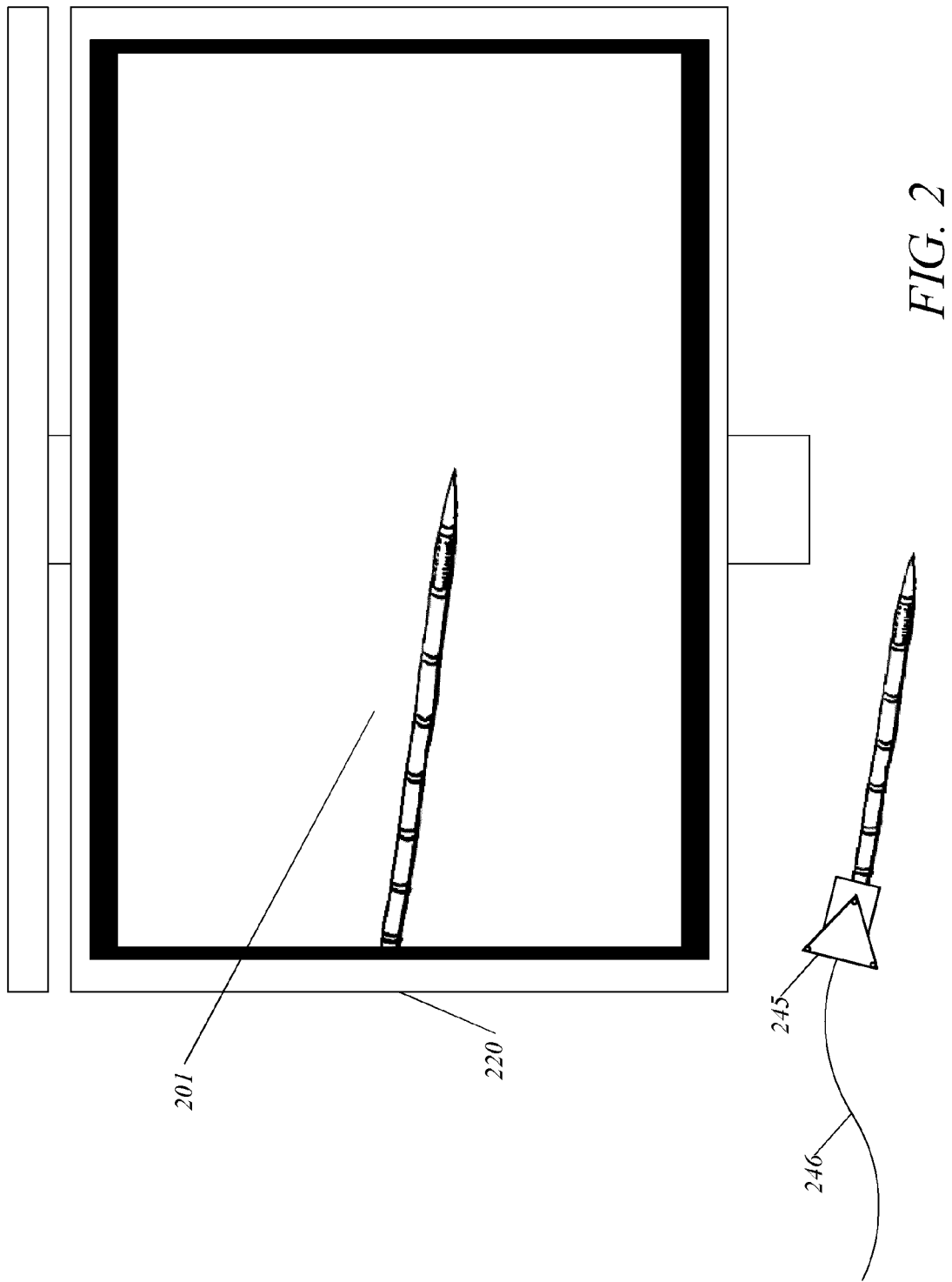
FIG. 2 illustrates a virtual rendering of an exemplary surgical instrument being displayed on a screen.

FIG. 2 illustrates a virtual rendering 201 of an exemplary surgical instrument 245 being displayed on a screen 220. In this case, the surgical instrument displayed is an ablation needle 245. The wire 246 connecting the ablation needle 245 to an ablation system is also depicted. Although only one surgical instrument 245 is displayed, it will be understood that multiple surgical devices can be tracked and displayed simultaneously on screen 220, as described in greater detail below with reference to FIG. 11-17.

The virtual surgical instrument 201 can be displayed in a virtual 3D space with the screen 220 acting as a window into the virtual 3D space, which can also be referred to as the perspective view. Thus, as the surgical instrument 245 is moved to the right, the virtual surgical instrument 201 also moves to the right. Similarly, if the surgical instrument 245 is rotated 90 degrees so that the tip of the surgical instrument is pointing towards the screen 220, the virtual surgical instrument 201 will likewise show the change in orientation, and show the tip of the virtual surgical instrument 201 in the background and the other end of the image 201 in the foreground.

Some models of medical devices have markings such as bands around the shaft (to indicate distance along the shaft), and a colored region near the tip to indicate where the radio frequency or microwave energy is emitted from in the case of an ablation probe. Healthcare providers performing medical device procedures are often familiar with these markings and can use them to help understand the spatial relationship between the medical device and anatomy. In some embodiments, the make and model of the medical device 245 is known to the image guidance system and the virtual medical device displayed (201) in display 220 can resemble medical device 245. The features of medical devices that can be rendered in the scene include the overall shape (diameter, cross sectional shape, curvature, etc.), color, distance markers, visuals or echogenic fiduciary markers, the state of deployable elements such as tines, paddles, anchors, resection loops, stiffening or steerable sleeves, temperature, radiation, light or magnetic field sensors, lens, waveguides, fluid transfer channels, and the like.

The type of medical device being used can be input into the image guidance system, can be a system default, can be detected by a camera or other device, can be received as data from an attached medical device, such as surgical system 149 in FIGS. 1A and 1B, or the information can be received in any other appropriate manner. Making the surgical instrument displayed on display 220 resemble the surgical instrument 245 can help healthcare providers associate the image guidance data with the real world and can provide more familiar guidance information to a healthcare provider, thereby further aiding the healthcare provider in the guidance task. For example, the healthcare provider can see the familiar markings on the medical device being displayed on the display 220 and therefore be familiar with the distance and relative placement of the displayed medical device with respect to other data, such as a tumor seen in an ultrasound (not depicted in FIG. 2). This knowledge of relative placement of items being displayed can help the healthcare provider move the medical device into place.

Consider an embodiment in which the virtual surgical instrument 201 in the display 220 is an ablation needle depicting the portion of the needle that will perform the ablation, for example, the portion that emits the radio or microwave energy. If the display 220 also includes ultrasound data, then the doctor can be able to find the tumor she wishes to ablate by moving the ultrasound probe around until she spots the tumor. In various embodiments, she will be able to see the displayed ultrasound data and its location relative to the displayed medical device with the markings. She can then drive the medical device until she sees, on display 220, that the emitter-portion of the medical device encompasses the tumor in the ultrasound, also seen on display 220. When she activates the ablation, she can then be much more certain that she has ablated the correct portion of the tissue. Various embodiments of this are discussed more below.

As another example, consider the physical markings that can be on the instruments themselves. These markings can help orient a healthcare provider during use of the instrument. In some embodiments, the image guidance unit can represent these markings in the images displayed in the display. For example, certain ultrasound transducers are built with an orientation mark (e.g., a small bump) on one side of the transducing array. That mark can also be shown in the ultrasound image on the scanner's display, to help the healthcare provider understand where the scanned anatomical structures shown on screen are located under the transducer, inside the patient. In some embodiments, the image guidance system can display a symbolic 3D representation of the orientation mark both next to the motion-tracked ultrasound slice (e.g., moving with the displayed ultrasound slice) and next to the 2D ultrasound slice also displayed by the system. An example of this is displayed in FIG. 5, where a small rectilinear volume corresponding to a feature on an ultrasound probe is shown both in proximity to the ultrasound slice displayed in 3D and the ultrasound slice displayed as a 2D image.

Other embodiments can track and display other types of instruments and their features. For example, a healthcare provider may want to track one or more of a scalpel, a biopsy, a cauterizer (including an electrocauterizer and Bovies), forceps, cutting loops on hysteroscopes, harmonic sheers, lasers (including $CO_2$ lasers), etc. For example, in various embodiments, the following devices can be tracked and various aspects of their design displayed on display 220: Olympus™ OES Pro Hystero-Resectoscope, SonoSurg Ultrasonic Surgical System Olympus™ GF-UC 160 Endoscope Wallus™ Embryo Transfer Catheter AngioDynamics® NanoKnife™, VenaCure™ laser, StarBurst, Uniblade, Habib® Resector Bovie™ Electrodes, Covidien Evident™, Cool-tip™ Ablation Antennas, Opti4™ Electrodes Microsulis MEA (microwave endometrial ablation), Acculis Halt™ Medical System Optimed BigLumen Aspiration Catheter Optimed Optipure Stent Central venous catheterization introducer medical device (such as those made by Bard and Arrow).

Once tracked, a healthcare provider is able to see image guidance data on display 220 that will allow her to know the relative pose, location, or emplacement of the tracked instrument(s) with respect to one another or with respect to imaging data and will be able to see, on display 220, the features of the instrument rendered in the scene.

Depicting Ablation Volume and Other Instrument Information

Figure 3:
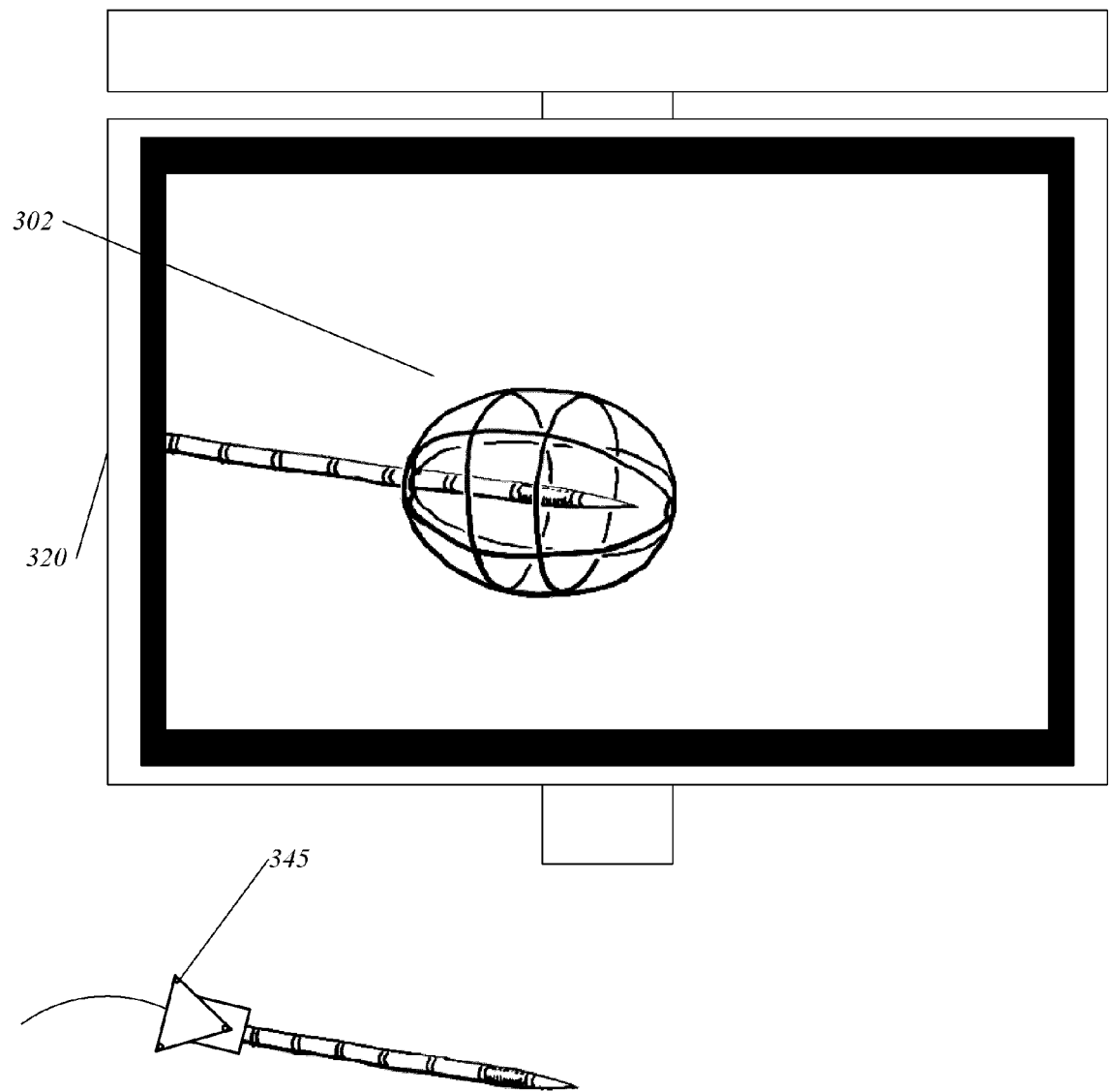
FIG. 3 illustrates a virtual rendering of an ablation volume of a surgical instrument being displayed on a screen.

Various embodiments of the systems herein depict as part of the image guidance data information related to the surgical instruments. For example, in some embodiments, an image guidance system such as the systems of FIG. 1A or 1B can illustrate an expected spherical ablation volume. For example, FIG. 3 shows an ablation needle 345 which has a darkened portion that indicates where the radio frequency or microwave energy for ablation will be emitted. In some embodiments, an image guidance system can display on display 320 the expected ablation volume 302. The ablation volume 302 can be shown as a transparent volume, a wireframe volume (depicted in FIG. 3), as a point cloud of various densities, as an outline, as a volume, or in any other appropriate manner. Although only one ablation volume 302 is displayed, it will be understood that multiple ablation volumes can be displayed for each medical device 345 that is displayed on the screen 320.

For some ablation needles, the expected volume of ablated tissue is neither spherical nor centered at the tip of the medical device. For example: a Covidien surgical microwave medical device has an ellipsoidal ablation volume; a Covidien Evident transcutaneous microwave medical device has a teardrop-like ablation volume; RFA Medical's bipolar ablation system uses two medical devices simultaneously, where each medical device has paddles that deploy after the medical device is inserted inside the tissue (which one can equate to a canoe's oar). In some embodiments, the ablation volume for such a medical device is, to a first approximation, a volume that lies directly between the paddles of the two medical devices.

The position and orientation of the volume can be specified by the placement of a tracked medical device, such as medical device 345 in FIG. 3. In some embodiments, with single medical device ablation systems, the volume's approximate size (e.g., girth and length, if ellipsoidal) can be either specified by the healthcare provider, or automatically computed by the guidance system. The ablation volume can be based on numerous parameters such as the medical device make and model, power and duration settings of the microwave or radio frequency generator, measured or estimated temperature and impedance of the target tissue or other tissue information, a formula, a look-up-table, fixed or default values, or based on any other appropriate available information.

Other instrument information can also be depicted. For example, if a cauterizer is tracked as part of an image guidance system, then the cauterization volume can be determined or estimated and that volume can be displayed. If a laser is tracked as part of the image guidance system, then the projected laser path can be determined or estimated and displayed. In embodiments where multiple medical devices are used, the combined volume can be shown, as described in greater detail below with reference to FIGS. 12A and 12B.

Depicting Medical Device Placement Trajectory, and Other Prediction Information

In certain procedures, the system can provide prediction information related to the surgical instruments. In the context of scalpel movement, this can be the location that the scalpel will hit if a healthcare provider continues to move the scalpel in a particular direction. In the context of ablation or biopsies, this can be the projected medical device placement if it is driven along its central axis, which is also referred to herein as a longitudinal axis.

Figure 4:
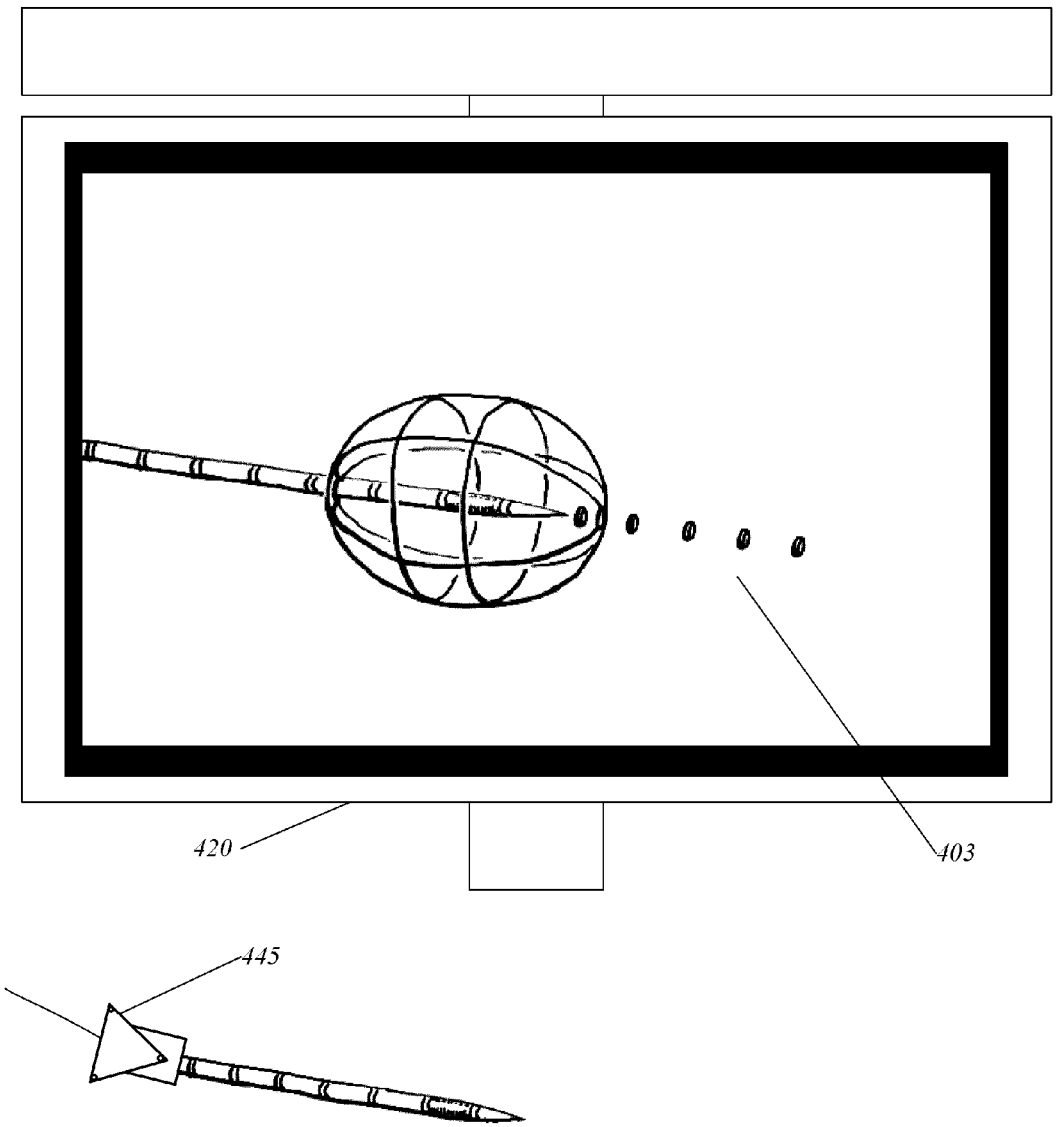
FIG. 4 illustrates a virtual rendering of a trajectory and ablation volume of a surgical instrument being displayed on a screen.

FIG. 4 illustrates both an ablation volume 404 for an ablation needle 445 and a projected needle drive 403. If a healthcare provider is driving an ablation needle 445 into tissue (not pictured), then she can know where the medical device will be driven. In some embodiments, the projected drive of a medical device can be depicted on the display 420 and can show the healthcare provider the projected path 403 that the medical device will take if it is driven along its central axis. Although the trajectory of only one medical device is displayed, it will be understood that the trajectory of multiple medical devices can be determined and displayed simultaneously on screen 420, as described in greater detail below with reference to FIGS. 12A, 12B, 13A, and 13B.

In some embodiments, in order to aid the healthcare provider in placing or orienting a medical device 445, an image guidance system, such as that depicted in FIG. 1A or FIG. 1B, can draw a number of rings about the axis of the medical device shaft, extrapolated beyond its tip, as depicted in FIG. 4. A healthcare provider can view and manipulate the position and orientation of the medical device 445 and its expected drive projection (via its displayed projected trajectory) before it enters the patient's tissue. In some embodiments, this is accomplished by the doctor positioning the virtual rings in the drive projection such that they are co-incident (or pass through) the ultrasound representation of a target, such as a tumor that the doctor has spotted in the ultrasound. This can allow the healthcare provider to verify that the medical device 445 is properly aimed at the target and can drive the medical device 445 forward into the tissue such that it reaches its desired target or destination. For example, if the doctor identifies a tumor in the ultrasound image (not pictured in FIG. 4), she can align the ablation needle 445 such that the drive projection rings on display 420 intersect or otherwise indicate that the medical device, if driven straight, will reach the tumor.

The rings can be spaced at regular (e.g., 0.5, 1, or 2 cm) intervals to provide the healthcare provider with visual or guidance cues regarding the distance from the medical device tip to the targeted anatomy. In some embodiments, the spacing of the rings can indicate other aspects of the data, such as the drive speed of the medical device, the density of the tissue, the distance to a landmark, such as the ultrasound data, or any other appropriate guidance data or property. In some embodiments, the rings or other trajectory indicators can extend beyond the medical device tip, by a distance equal to the length of the medical device-shaft. This way, the user knows if the medical device is long enough to reach the target—even before the tip enters the patient. That is, in some embodiments, if the rings do not reach the target with the tip still outside the body, then the tip won't reach the target even when the entire length shaft is inserted into the body.

Other display markers can be used to show trajectory, such as a dashed, dotted, or solid line, transparent medical device shaft, point cloud, wire frame, etc. In some embodiments, three-dimensional rings can be used and provide depth cues and obscure little of the ultrasound image. Virtual rings or other virtual markers can be displayed semi-transparently, so that they obscure less of the ultrasound image than an opaque marker would.

Other prediction information can also be displayed. For example, if a scalpel is being tracked by the image guidance system, then a cutting plane corresponding to the scalpel can be displayed (not pictured). Such a cutting plan can be coplanar with the blade of the scalpel and can project from the blade of the scalpel. For example, the projected cutting plane can show where the scalpel would cut if the doctor were to advance the scalpel. Similar prediction information can be estimable or determinable for cauterizers, lasers, and numerous other surgical instruments.

Depicting Combinations of Graphics

As discussed herein, when there are multiple instruments or devices being used in a procedure, images, graphics, and data associated with the multiple instruments can be displayed to the healthcare provider. In some embodiments, as depicted in FIG. 5, when there are two medical devices 545 and 555 being used and tracked in a procedure, data, images, and graphics associated with those two images can be combined and displayed on the same display.

Figure 5:
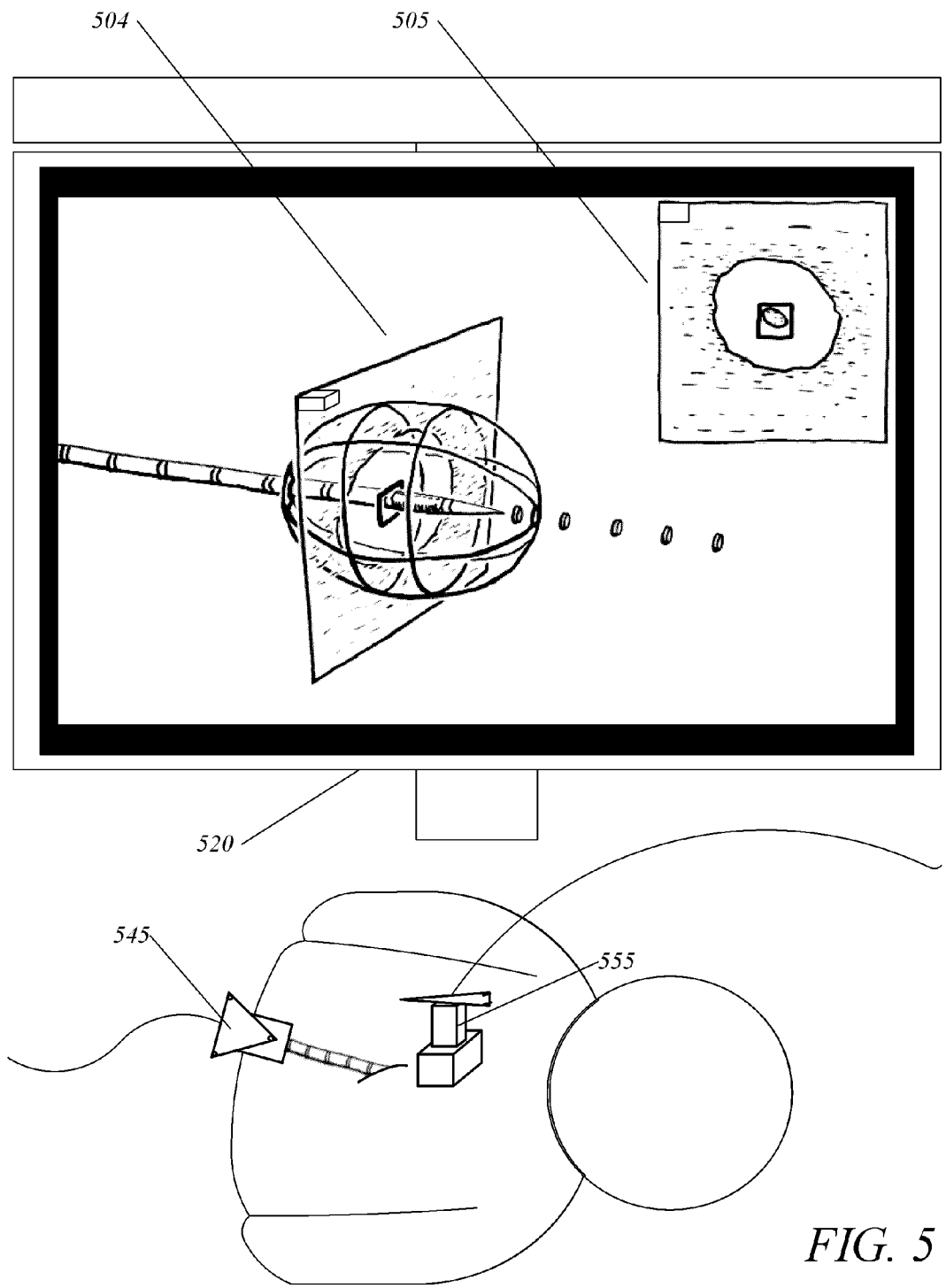
FIG. 5 illustrates a virtual rendering of a surgical instrument and medical images displayed on a screen.
Figure 6:
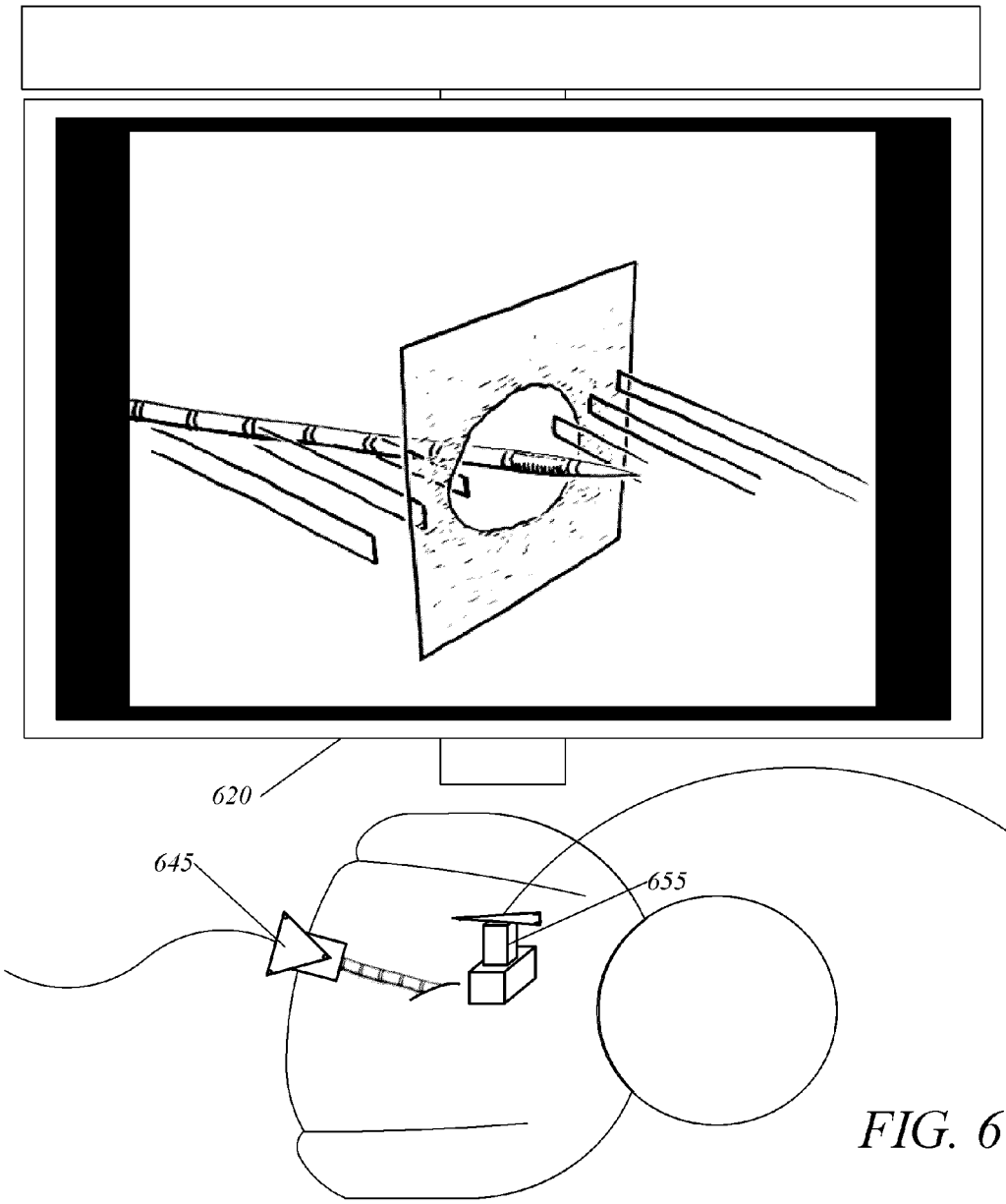
FIG. 6 illustrates a virtual rendering of a surgical instrument and guidance cues displayed on a screen.

FIG. 5 depicts an ablation needle 545 and an ultrasound probe 555 being used during a procedure. Data associated with each of the devices 545 and 555 are displayed on the display 520. As described previously with reference to FIG. 2, the devices 545 and 555 can be displayed in a virtual 3D space with the screen 520 acting as a window into the virtual 3D space and providing a perspective view. Thus, as the surgical instrument 545 are moved to the right, the virtual surgical instrument 501 also moves to the right. Similarly, if the ultrasound probe 555 is moved to the right, the ultrasound image 504 is also moved to the right. If the surgical instrument 545 is rotated 90 degrees so that the tip of the surgical instrument is pointing towards the screen 520, the system 100 will likewise adjust the virtual surgical instrument 501 to show the change in orientation, and show the tip of the virtual surgical instrument 501 in the background and the other end of the virtual surgical instrument 201 in the foreground. Similarly a rotation of the ultrasound probe 555 will result in a rotation of the ultrasound image 504.

The data from two or more devices can be combined and displayed based on their relative emplacements or poses. For example, the system 100 can determine an image plane based on the emplacement information of the ultrasound probe 555. Further, the ultrasound image 504 can be displayed on the image plane with respect to a virtual ablation needle 502 on a display 520 in a manner that estimates the relative emplacements or poses of an ultrasound probe 555 and ablation needle 545. As illustrated in FIG. 5, the graphics associated with the virtual ablation needle 502, including the ablation volume 506 and projected drive location 508, are shown spatially located with the oriented planar ultrasound image 504 on display 520.

In addition, the display 520 includes an intersection indicator 510 that indicates the where the virtual ablation medical device 502 intersects the ultrasound image 504. In some embodiments, the intersection indicator 510 can be displayed before the medical device is inserted, thereby allowing the healthcare provider to see where the medical device will intersect the image.

In this image, a tumor 512 appears in the ultrasound image 504 and the virtual ablation needle 502 is shown driven through the tumor 512. The ablation volume 506 estimates where ablation would occur if the tissue were ablated at that time. The healthcare provider can see that the ablation volume 506 appears to cover the tumor displayed in the ultrasound image.

Various embodiments can include any combinations of the graphics described above with reference to FIGS. 2-7 and/or other graphics. For example, in some embodiments, data related to a single surgical instrument (such as an ablation needle, ultrasound probe, etc.) can be presented in more than one manner on a single display. Consider an embodiment in which device 545 is an ablation needle and device 555 is an ultrasound transducer. As mentioned previously, as the medical devices are displayed in a virtual 3D space, with the screen 520 acting as a window into the virtual 3D space, if a healthcare provider orients ultrasound transducer 555 such that it is perpendicular to the monitor, the 3D view of the ultrasound image would show only the edge and the ultrasound image would not be visible. In some embodiments, the image guidance system can track the healthcare provider's head using a position sensor, such as first and/or second position sensing units 110 and/or 140 of FIG. 1A or FIG. 1B. The healthcare provider can then move her head to the side, so that she sees the ultrasound image from a different perspective.

In some embodiments, the image guidance system can constantly display an additional 2D view of the ultrasound image 505 (in screen space), simultaneous to the 3D depiction of the procedure, so that the ultrasound image is always visible, regardless of the orientation in which the healthcare provider holds the transducer. This is illustrated in FIG. 5. This display of the ultrasound data can be similar to what a healthcare provider is accustomed to seeing with traditional ultrasound displays. This can be useful to provide the healthcare provider with imaging to which she is accustomed and allows a healthcare provider to see the ultrasound data regardless of the then-current orientation of the ultrasound probe with respect to the user.

In some embodiments, the 2D view 505 of an ultrasound image is depicted in the upper right corner of the monitor (though it can be placed in any location). In some embodiments, the guidance system can automatically (and continually) choose a corner in which to render the 2D view of the ultrasound image, based on the 3D position of the surgical instruments in the rendered scene. For example, in FIG. 5, ablation needle 545 can be held in the healthcare provider's left hand and the medical device shaft is to the left of the 3D ultrasound image slice, so that the 2D ultrasound image 505 in the upper right corner of display 520 does not cover any of the 3D features of the medical device (or vice-versa). If the medical device were held in the healthcare provider's right hand, the virtual medical device shaft would appear on the right side. To prevent the 2D ultrasound image in the corner of display 520 from covering the medical device shaft, the system can automatically move it to a corner that would not otherwise be occupied by graphics or data.

In some embodiments, the system attempts to avoid having the 2D ultrasound image quickly moving among corners of the display in order to avoid overlapping with graphics and data in the display. For example, a function f can be used to determine which corner is most suitable for the 2D ultrasound image to be drawn in. The inputs to f can include the locations, in the screen coordinate system, of the displayed medical device tip, the corners of the 3D ultrasound image, etc. In some embodiments, f's output for any given point in time is independent of f's output in the previous frames, which can cause the ultrasound image to move among corners of the display rapidly. In some embodiments, the image guidance system will filter f's output over time. For example, the output of a filter g, for any given frame, could be the corner which has been output by f the most number of times over the last n frames, possibly weighting the most recent values for f most heavily. The output of the filter g can be used to determine in which corner of display 520 to display the 2D ultrasound image and the temporal filtering provided by g can allow the 2D ultrasound image display to move more smoothly among the corners of the display 520.

In some embodiments, other appropriate virtual information can be overlaid on the 2D ultrasound image as well. Examples include: an indication of the distance between the medical device's tip and the point in the plane of the ultrasound image that is closest to the medical device tip; the cross section or outline of the ablation volume that intersects with the ultrasound slice; and/or the intersection point, box, outline, etc. between the medical device's axis and the ultrasound image plane.

Representing Spatial Relationships

At times, when three dimensional relationships are depicted in 2D, or even in 3D, it can be difficult to gauge the relative positions, orientations, and distances among various objects. Consider FIG. 5, in which an ablation needle is shown intersecting an ultrasound image. Depending on the embodiment, it can be difficult to determine the relative angle of the ablation needle and the ultrasound image as well as the distances of various portions of the image plane to the ablation needle.

In some embodiments, the image guidance system can indicate spatial relationships with graphical indicators. For example, in FIG. 6, graphical indicators help indicate the spatial relationship between a medical device and an ultrasound image plane. These also provide an indication of the relative angle of the medical device and the image plane.

In some unpictured embodiments, the image guidance system can draw "guidance graphics" in the form of projective lines between the medical device and the ultrasound slice. These lines can be perpendicular to the plane of the slice and serve to indicate the most likely location in the slice where the medical device will become visible if it is moved to become coplanar with the slice. Together with stereoscopic head-tracked visualization, the projective lines help a healthcare provider determine a more accurate assessment of the location of the medical device with respect to the ultrasound slice.

Returning to FIG. 6, in some embodiments, uniform-thickness lines 602 between virtual medical device and the image plane can be displayed on display 620. The lines can represent the spatial relationship with three-dimensional rectangular (or any shape) medical device projection bars, lines (dashed or solid), etc. In various embodiments, the projection bars can be drawn perpendicular to the image, and in such a way that their small edges are aligned with (or parallel to) either the vertical (FIG. 6) or the horizontal margins of the ultrasound slice. In some embodiments, the screen-space size of the projection bars can be variable (e.g., distance-dependent) due to perspective. Thus, they can provide depth cues for the healthcare provider. Further, the staircase appearance of the bars' end edges at the plane of the slice can be a further visual cue for the orientation of the medical device with respect to the image plane.

Representing Non-Intersecting Objects or Images

Figure 7:
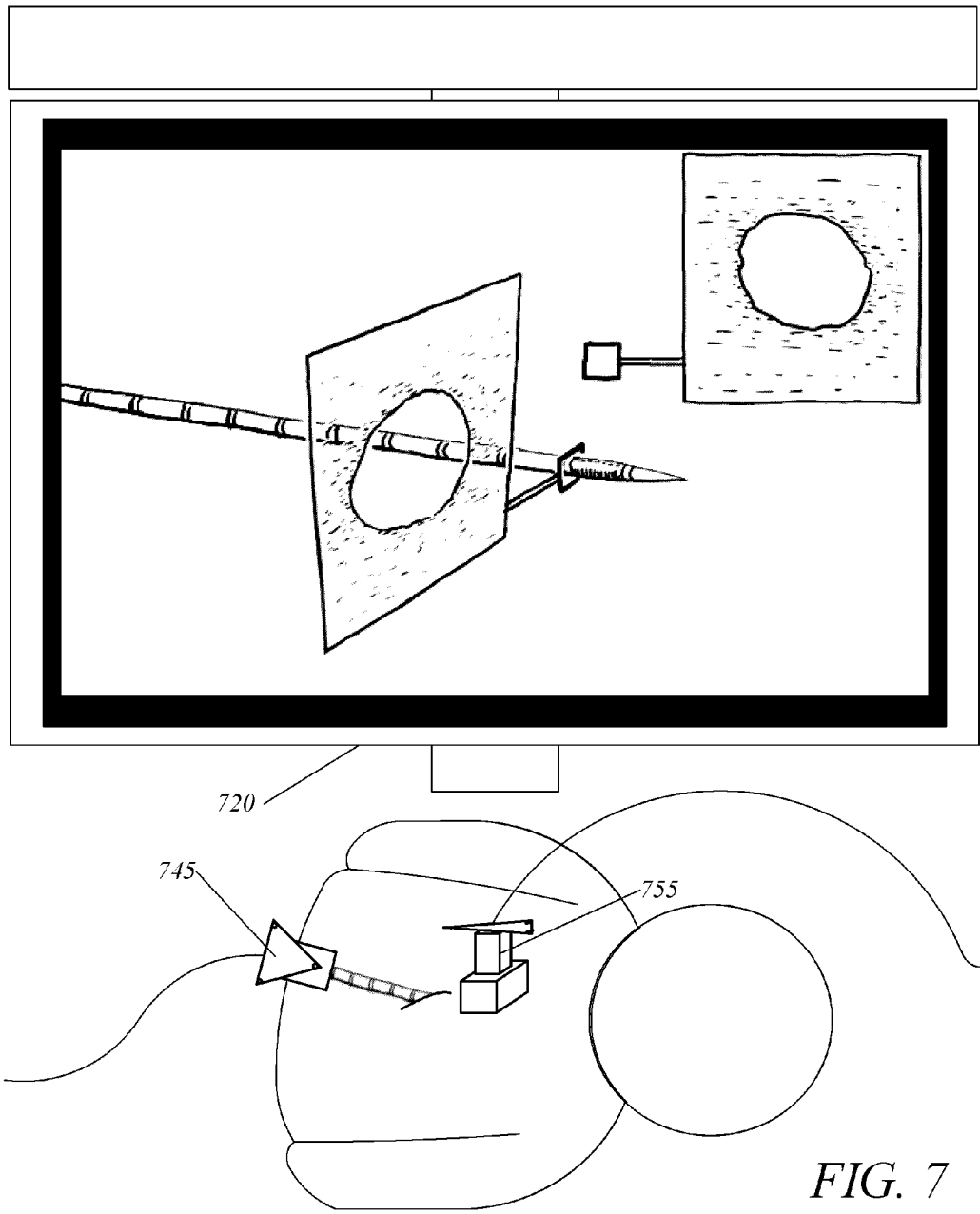
FIG. 7 illustrates a virtual rendering of a surgical instrument and guidance cues displayed on a screen.

When data related to two devices or surgical instruments are displayed with relative emplacement, it can be difficult to orient their relative locations if they do not intersect. In some embodiments, an image guidance system will render relative location information. The relative location information can be shown with color (e.g., objects can be rendered in brighter colors if they are closer), with rendering techniques (e.g., objects can be rendered with transparency so that one object behind another can be visible, but visually appear behind the closer object), with geometry (e.g., a geometric connector can be shown that will allow the viewer to discern the relative relationships), or with any other appropriate technique. FIG. 7 illustrates example geometry and transparency being used to show relative locations of two objects.

For example, in some embodiments, if the intersection point of a medical device 702 is outside of the area of the ultrasound slice 704, the image guidance system can draw geometry, such as a line (or rectangle) in the image plane to indicate the relative positions of the medical device(s) and ultrasound image. This is depicted in FIG. 7. In some embodiments, the relative locations can also be represented using vertical and horizontal elements coplanar with the ultrasound or other image. In some embodiments, using geometry that is coplanar with the ultrasound image slice can provide an intuitive understanding of the relative locations of an image slice and an ablation needle.

Marking Points of Interest

In certain procedures, healthcare providers desire to keep track of multiple spots within the volume of the patient or keep track of a single point or feature while looking at other parts of the volume. For example, when a healthcare provider is going to perform an ablation, before inserting any medical devices, the healthcare provider will often scan the tissues at the procedures site to find all targets (e.g., tumors) and note other features of the tissues. Then, later in the procedure, the healthcare provider can return to the previously identified points-of-interest. For example, a healthcare provider might first scan the liver and find seven lesions that she will attempt to ablate. After ablating the first lesion, she might be required to find the second lesion again, and so forth. Before finishing the procedure, she might be required to verify that she has ablated all seven of the lesions that she identified at the beginning of the procedure. This constant scanning and rescanning can be time consuming and error prone. Further, in a procedure where the healthcare provider is attempting to locate, for example, fluid-filled cysts, once a medical device pierces the cyst, the fluid can drain out, making the target difficult or impossible to locate again with ultrasound.

Figure 8:
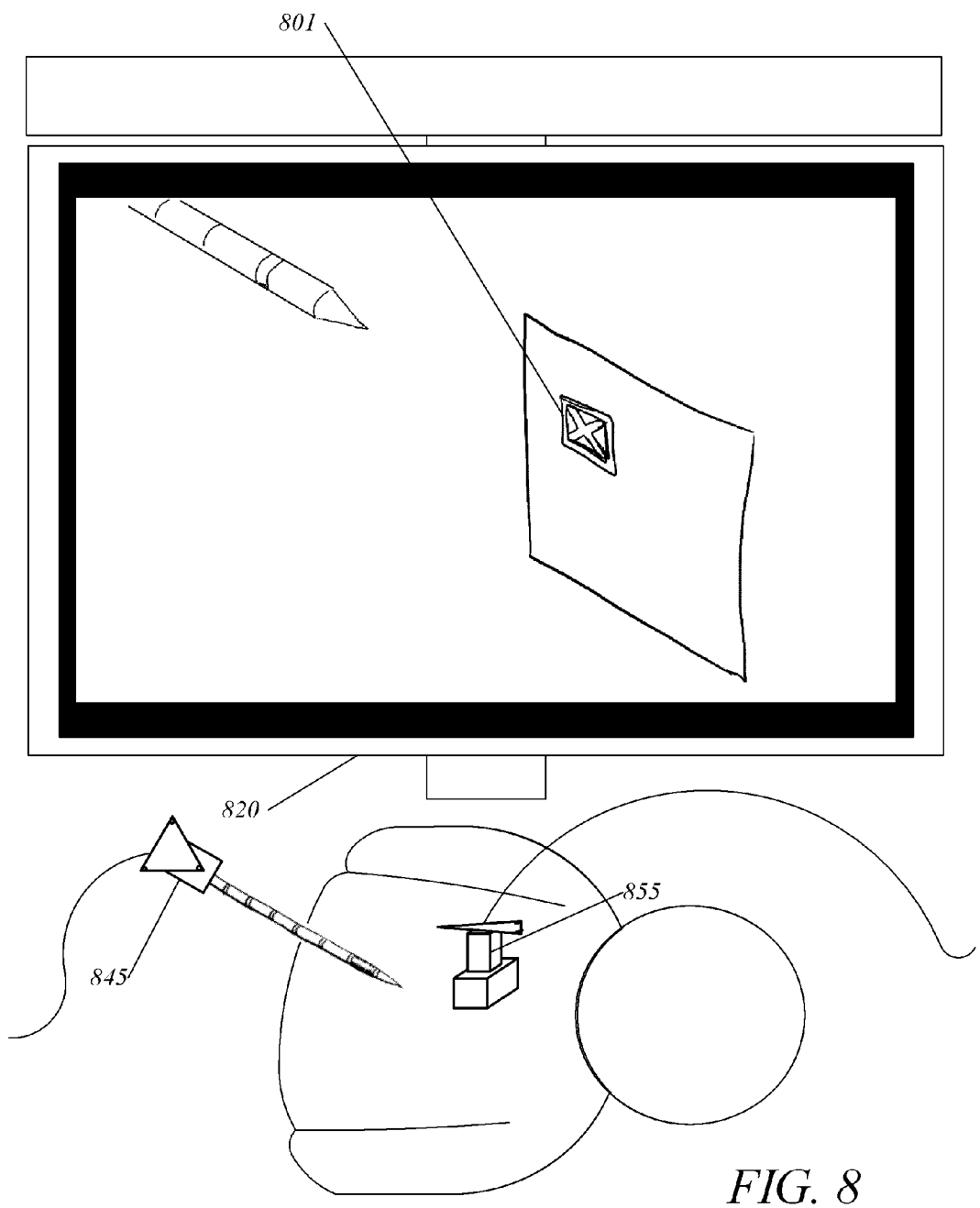
FIG. 8 illustrates a virtual rendering of a surgical instrument and guidance cues displayed on a screen.
Figure 9:
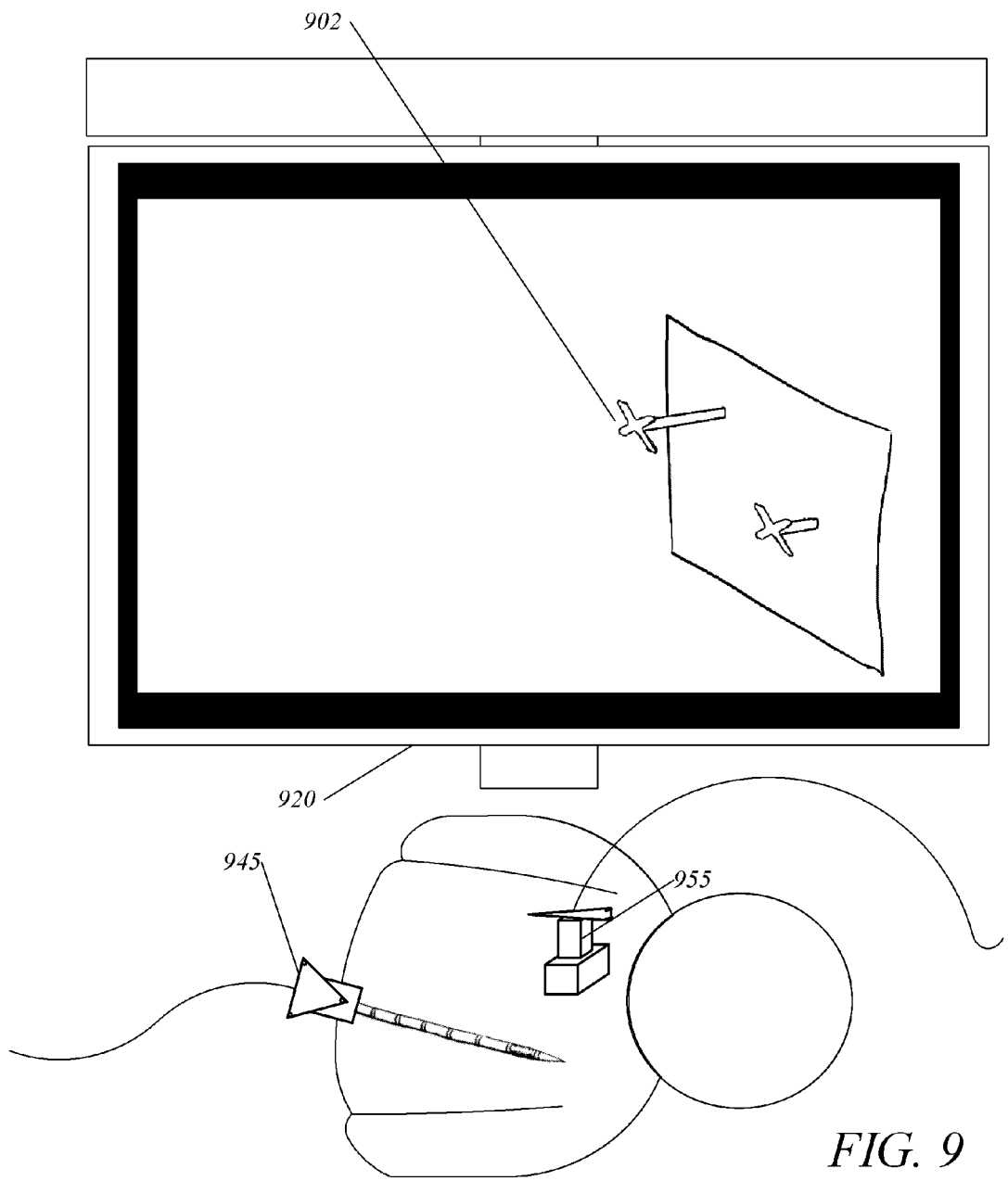
FIG. 9 illustrates a virtual rendering of a surgical instrument and guidance cues displayed on a screen.

In some embodiments, the image guidance system allows the healthcare provider to mark or keep track of points or features of interest. In various embodiments, the healthcare provider can mark the points or features of interest in various ways. For example, consider a procedure where the doctor is using the image guidance system with an ablation needle and an ultrasound probe. The doctor can be able to mark the point by pressing a button on a keyboard or medical device, by gesturing or issuing a verbal command, or with any other appropriate method. The point of interest can be marked at the point where the medical device intersects with the ultrasound image plane, where the medical device's projection intersects with the ultrasound image plane, or any other appropriate relationship (such as at the location of the tip of the medical device). For example, when the healthcare provider identifies a point-of-interest within the ultrasound image, she can point to it using the medical device even if the medical device is outside the body of the patient. This is depicted in FIG. 8. The healthcare provider (or assistant) can then press, for example, a button or foot pedal, which informs the image guidance system to store the 3D position of this point-of-interest 801. FIG. 8 illustrates an X being displayed where a point of interest 801 has been marked. In some embodiments, the system can then display the position of this point-of-interest 801 relative to the ultrasound plane and the medical device. For example, an X-shaped marker 902 can be displayed on display 920 to show the relative position of the marked position and the surgical instruments, as depicted in FIG. 9. In some embodiments, the system can also display a bar that connects the X marker 902 of the point-of-interest to the nearest point (or the point to which a normal vector of the image plane would reach the X), as depicted in FIG. 9. This visually indicates to the healthcare provider the distance between the ultrasound image and this point-of-interest. Should the healthcare provider want to see the point of interest again in the live ultrasound image, the graphics indicate to where she should move the ultrasound transducer to view that point in the ultrasound image. In some embodiments, the image guidance system can also display the numerical distance (e.g., in mm) between the ultrasound image and the point-of-interest (not shown).

Healthcare providers, during some liver ablation procedures, can manage fifteen points-of-interest, or even more. As depicted in FIG. 9, in some embodiments, there can also be multiple markers 902 of point of interest simultaneously displayed. The image guidance system can be able to store and display any number of points of interest simultaneously. If there is more than one point-of-interest in view, the image guidance system can display a number next to each one (not pictured). In some embodiments, in order to reduce visual clutter if there are many points of interest, those points which are closer to the ultrasound image plane are drawn more saliently or vividly (with more bold color and thicker lines) while the points that are far away are drawn less saliently (more transparent, blurred, muted colors, etc.). Additionally, in various embodiments, other representations other than an X (such as a point, point cloud, sphere, box, etc.) can be used and multiple markers or locations can be represented with different markings.

In some embodiments, the image guidance system stores the points-of-interests' positions in the position sensing system's coordinate system. If the position sensing system is fixed to the image guidance system, then, if the patient or image guidance system are moved, stored points-of-interest can become incorrectly located. In some embodiments, this can be remedied via a fiducial or other detectable feature or item, the pose of which relative to the tracking system can be continually, continuously, periodically, or occasionally measured. The fiducial can be attached to the operating table, the patient's skin, or even embedded into the tissue itself (e.g., as a magnetic tracking coil), and the points-of-interest' positions, relative to it, can be stored and displayed. For example, in a system where magnetic tracking is used, a magnetic tracking coil can be affixed to the operating table or patient. In some embodiments, the healthcare provider can draw the annotations.

Figure 10A:
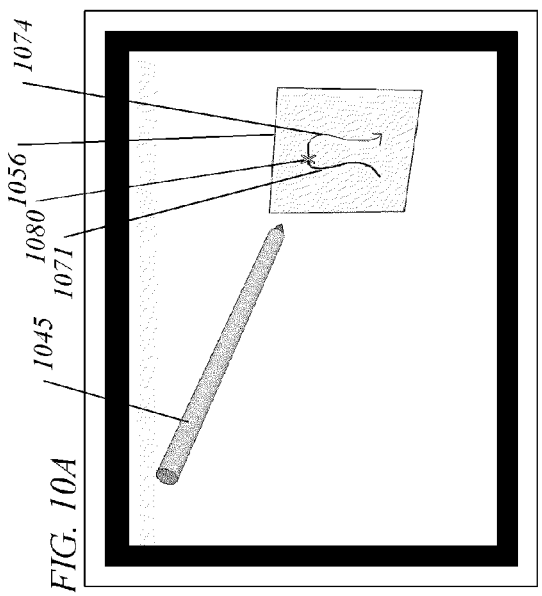
FIG. 10A-10D illustrates a virtual rendering of a surgical instrument and annotations displayed on a screen.
Figure 10B:
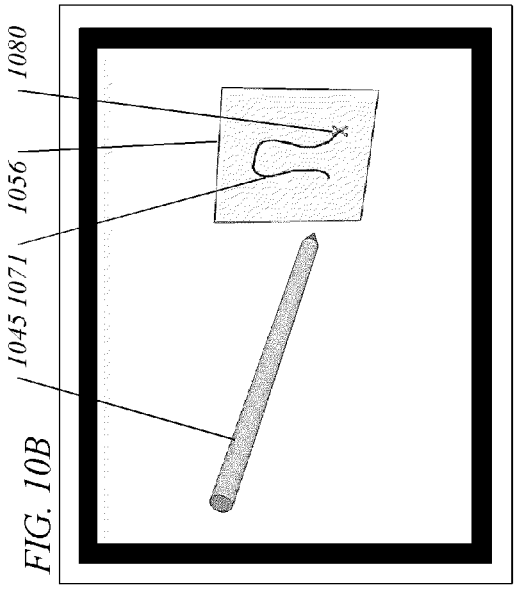

FIGS. 10A-10D illustrate examples of image annotation in image-guided medical procedures. FIGS. 10A-10D show a representation on a computer screen 1020 of an annotation being made with a medical device (represented on the display 1020 as medical device 85). The medical device can be used to annotate an image 1056. FIG. 10A illustrates the manipulation of a medical device 85 pointing at an image 1056 (e.g., an ultrasound image 1056). The operator can make an annotation by moving the medical device 85 through space in order to draw curve 1071 on image 1056. In certain embodiments, arrow 1074 can indicate the direction that the operator plans to or will draw in the future. In some embodiments, arrow 1074 is not displayed. Location indicator 1080 can represent the place on image 1056 currently pointed to by medical device 85. Location indicator 1080 can be any appropriate indicator such as an "X," an arrow, a differently-colored area, etc. In FIG. 10B the operator has further moved medical device 85 in order to complete the annotation 1071 on image 1056. As is depicted in FIG. 10B, the indicator 1080 of the intersection between the axis of the medical device 85 and the image 1056 has now reached the lower-right quadrant of the image 1056.

The image 1056 can be associated with a medical device, such as an ultrasound transducer (not pictured in FIGS. 10A-10D). The image 1056 can be an ultrasound image 1056, or the image 1056 can be a slice or image from other 3D visualizable medical data such as is described above.

Figure 10C:
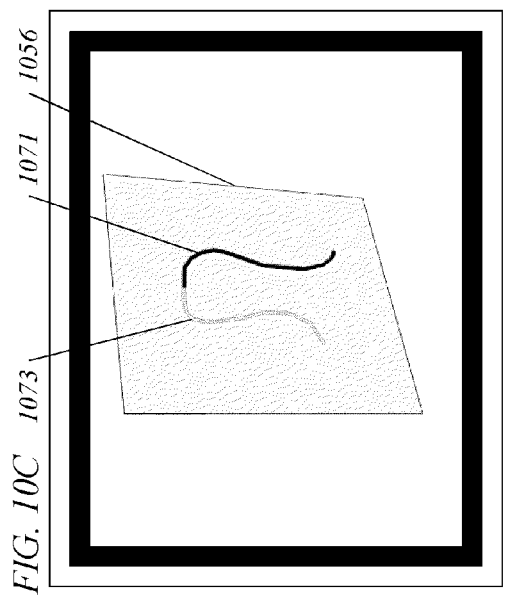

The annotation 1071, although it has been drawn on an image 1056, can be located in the virtual 3D space—defined by the placement of the image 1056 and the annotation 1071. FIG. 10C depicts image 1056, associated with the ultrasound transducer turned or rotated about its vertical axis (axis not depicted in FIG. 10C). Therefore, part of the annotation 1071 is depicted in front of the image 1056, and part of the annotation 1073 is behind the image 1056 thus illustrating the existence in the virtual 3D space of the annotation 1071/1073. The location and display of annotations in the virtual 3D space allow an operator to make an annotation for a feature (e.g., a tumor, cyst, or vein), and allow her to locate that feature again later.

Figure 10D:
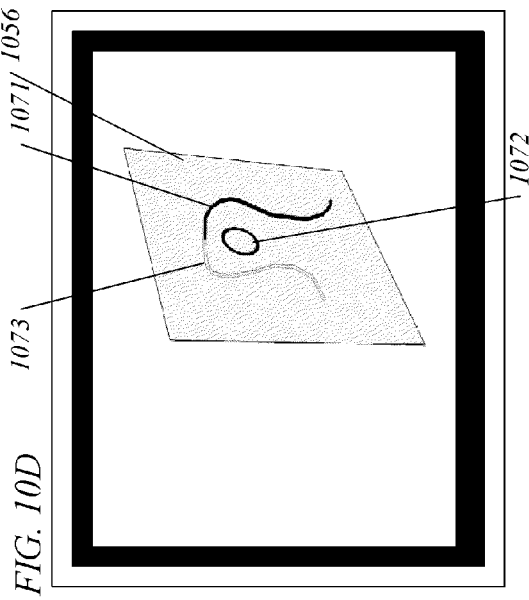

FIG. 10D illustrates that an operator can make a second annotation 1072 on the image 1056. Part of the first annotation 1071 is in front of the image 1056 and part 1073 is behind. By manipulating the pose of the image 1056 (e.g. by manipulating the ultrasound transducer), the operator can choose new locations within 3D space for annotations. As noted above, the annotations can be for a blood vessel, tumor, or any other object or location of interest for the operator. There need not even be a particular object in the medical image that the operator is annotating. The operator can, for example, sign her name or write a note. For example, an operator can circle or make marks near multiple tumors, trace a line such as annotation 1071 along a vein or artery, etc. In some embodiments, if the operator moves image 1056 during annotation, the operator can make non-planar annotation (see, e.g., FIGS. 2 and 3). As such, the operator can make a sphere or other non-planar annotation in order to annotate the volumetric aspects of a feature of interest. For example, the operator can draw the outline of a sphere around a tumor or cyst.

Multiple Medical Device Tracking

FIG. 11 is a diagram illustrating various features of multiple medical devices 1102, 1104 that can be tracked by the system. Although two medical devices are illustrated, it will be understood that the system can track and/or display fewer or more medical devices as desired. In the illustrated embodiment, each medical device has a tip 1106A, 1106B, an exposed electrode 1108A, 1108B, an insulating tube 1110A, 1110B, and are associated with one or more tracking units (not shown), each of which are described in greater detail above.

Using the emplacement information received from the tracking units, the system can calculate the emplacement of each medical device within a predefined area as well as the relative emplacement with respect to each other. The system can also determine the longitudinal axis 1112A, 1112B (also referred to as the central axis) of the medical devices 1102, 1104 and use the longitudinal axes to calculate the trajectories, of each medical device, angle differences between the medical devices, etc. This data can be used to generate useful information for display for the healthcare provider.

As mentioned previously, in some medical procedures that use multiple medical devices, it is desirable to have the medical devices on the same plane (e.g., the tips on the same plane) and parallel with each other. The system described herein can aid a healthcare provider in placing the medical devices so that they are level and parallel with each other.

During, or prior to, a medical procedure, one of the medical devices can be selected as the foundational medical device. In the illustrated embodiment of FIG. 11, medical device 1102 is selected as the foundational medical device. In some embodiments, the foundational medical device is selected as the first medical device placed in the tissue, and secondary medical devices (e.g., medical device 1104 in the illustrated embodiment) are placed thereafter. In certain embodiments, the foundational medical device is 1102 selected by the user and the remaining medical devices are the secondary medical device 1104.

Once a foundational medical device is selected, the system can calculate one or more foundational planes, and can generate foundational plane indicators for the different foundational planes. As used herein, a foundational plane is a plane that is perpendicular to a trajectory of the foundational medical device and intersects at least one point of the foundational medical device and/or intersects at least one point in the trajectory of the foundational medical device. In some embodiments, the trajectory of the foundational medical device is determined by the longitudinal axis of the foundational medical device.

Accordingly, a variety of foundational planes can be calculated and used as described herein. For example, the foundational tip plane 1114 is a foundational plane that intersects a tip of the foundational medical device 1102. As another example, the foundational electrode plane 1116 is a foundational plane that intersects the electrode of the foundational medical device 1102. In some embodiments, the foundational electrode plane intersects the electrode at a location where the exposed electrode 1108A ends, such as where the exposed electrode meets the insulated tube 1110A or handle. In certain embodiments the foundational electrode plane 1116 intersects the exposed electrode 1108A at any location.

The emplacement information can also be used to calculate various distances between the foundational medical device and other medical devices and between the foundational planes and the medical devices. In some embodiments, the emplacement information can be used to calculate the relative distance 1118 between the tips 1106A, 1106B of the medical devices 1102, 1104.

In certain embodiments, the emplacement information can be used to calculate the horizontal distance 1120 between the tips 1106A, 1106B of the medical devices 1102, 1104. The horizontal distance 1120 can represent the distance between the tips 1106A, 1106B if the tips were (or are) level (e.g., on the same plane, such as the foundational tip plane). In some embodiments, the horizontal distance can be calculated by determining the distance between the tip 1106A of the foundational medical device 1102 and the location of the tip 1106B of the secondary medical device 1104 if the secondary medical device 1104 were on the foundational tip plane 1114.

The emplacement information can also be used to calculate the vertical distance 1122 between the tips 1106A, 1106B of the medical devices 1102, 1104. The vertical distance 1122 represent the distance one tip is in front of or behind the other tip (e.g., how far the tip of one medical device is from the foundational tip plane). In some embodiments, the vertical distance can be calculated by determining the distance between the tip 1106B of the secondary medical device 1104 and the foundational plane 1114. This information can be used to determine whether the medical devices 1102, 1104 are level (e.g., whether the tips are on the same plane, such as the foundational tip plane).

The emplacement information can also be used to calculate the relative difference in degrees between the medical devices 1102, 1104 (e.g., how many degrees from being parallel). For example, the system can compare the longitudinal axis 1112A of the foundational medical 1102 with the longitudinal axis 1112B of the secondary medical device 1104 to determine how many degrees difference there is between the two. The difference in degrees can be displayed as a number or graphical indicator. For example, the system can provide projective lines as discussed previously and also in greater detail below with reference to FIGS. 12C and 12D to indicate the difference in degrees between medical devices. The number or graphical indicator can aid a user in placing the needles parallel to each other. This can be used in conjunction with the foundational plane information to place the needles level (e.g., the tips on the same plane) and parallel with each other.

The emplacement information can also be used to determine a target axis 1124 for the secondary medical device 1104. In some embodiments, the target axis 1124 can be the axis at which the secondary medical device 1104 is to be placed. The target axis 1124 location can be based on user input entered prior to or during the procedure, such as where the user wants the secondary medical device to be placed for a medical procedure and/or dynamically determined based on the emplacement of the foundational medical device 1102. In certain embodiments, the target axis 1124 is a predetermined distance from and parallel to the longitudinal axis 1112A of the foundational medical device 1102. The predetermined distance can be selected by a user or dynamically determined by the system 100 based on the length of the exposed electrodes of the medical devices, a model of the ablation or biopsy parameters of the medical devices (e.g. a lookup table), 4) tumor size, etc.

In some embodiments, the system can determine relative spatial indicators that indicate the relative distance between portions of the secondary medical device 1104 and the target plane or target axis (e.g., the longitudinal axis 1112A of the foundational medical device 1102, location of the preferred placement of the secondary medical device 1104, etc.). In certain embodiments, the relative spatial indicators can indicate the distance from portions of the secondary medical device 1104 to corresponding portions of the foundational medical device 1102.

Once the system determines one or more of the parameters described above, it can cause a display device to display those parameters. In some embodiments, one or more of the determined parameters are displayed for each medical device that is being tracked. In certain embodiments, the system displays one or more parameters of a selected medical device (or multiple selected devices) that is being tracked. In some embodiments, the one or more parameters of the selected medical device are displayed in conjunction with the foundational medical device.

A user can select the selected medical device using any number of different inputs (e.g., touchscreen, keyboard, mouse, foot pedal, button, etc.). Once the selected medical device is selected, the system can cause the display device to display one or more of the associated parameters. For example, when a user is attempting to place a medical device during a procedure, she can press a button that causes the medical device to be the selected medical device. In response, the system can display one or more parameters associated with the selected medical device, such as, but not limited to, trajectory, intersection indicators, relative spatial indicators, etc., as will be described in greater detail below with reference to FIGS. 12A-12D.

In addition, the system can use the emplacement information to determine a perspective view of the virtual 3D space. For example, the system can use any one or a combination of the following points as the center of perspective for the perspective view: an image (e.g., center of an ultrasound image); the center of the foundational needle; the center of the exposed electrode 1108A of the foundational medical device 1102, the center of the exposed electrode 1108B of the selected secondary medical device 1104 (or other secondary medical device); the location between the foundational medical device 1102 and the selected secondary medical device 1104; the center of the exposed electrode of a non-selected secondary medical device; the center of all medical devices selected thus far in the procedure; the center of all medical devices within a distance from the foundational medical device; the center of all medical devices.

Using the emplacement information and calculated data, the system can provide a user various indicators to aid in the placement of the medical devices, as will be described in greater detail below with reference to FIGS. 12A-17. The system can determine, calculate and/or display any of the emplacement information, or any combination of the emplacement information described herein in an embodiment.

Rendering with Multiple Medical Devices

FIGS. 12A-12D illustrate embodiments of displaying image guidance data for multiple medical devices. In the illustrated embodiments of FIGS. 12A and 12B, the display 1200 includes a 2D image display area 1202, as described in greater detail above with reference to FIG. 5, a 3D image display area 1204, and a relative emplacement measurement display area 1206. However, it will be understood that in some embodiments, fewer or more of the areas described can be included. For example, in certain embodiments any one or any combination of the areas mentioned above can be included in the display 1200.

2D Image Display Area

The 2D image display area 1202, described in greater detail above with reference to FIG. 5, can include an image 1223 and image guidance cues. The image 1123 can include any one of, or any combination of, an ultrasound image or images, ultrasound video, MRI, CT scan images, and/or any other image. In some embodiments, the image 1223 in the 2D image display area 1202 is the same as, or identical to, the image data 1224 provided in the 3D image display area 1204. In addition, the 2D image display area 1202 can include some or all of the image guidance cues and virtual medical devices described in greater detail below with reference to the 3D image display area 1204. In the illustrated embodiment of FIG. 12A, the 2D image display area 1202 includes trajectory indicators 1218, 1222 and an image plane intersection indicator 1226 overlaid onto an ultrasound image.

3D Image Display Area

The 3D image display area 1204 can represent a virtual 3D space that corresponds to an actual 3D space that is being tracked. In the illustrated embodiment, the 3D image display area 1204 includes a virtual medical imaging device 1208, an image 1210, as described in greater detail above with reference to FIGS. 2 and 5.

Furthermore, the 3D image display area 1204 can include multiple virtual medical devices 1212, 1214, 1216, image guidance cues (e.g., trajectory indicators 1218, 1220, 1222, image plane intersection indicators 1224, 1226, foundational plane indicators, 1228, 1330, and foundational plane intersection indicator 1232), a patient orientation indicator 1234, and medical provider indicator 1236.

Figure 12A:
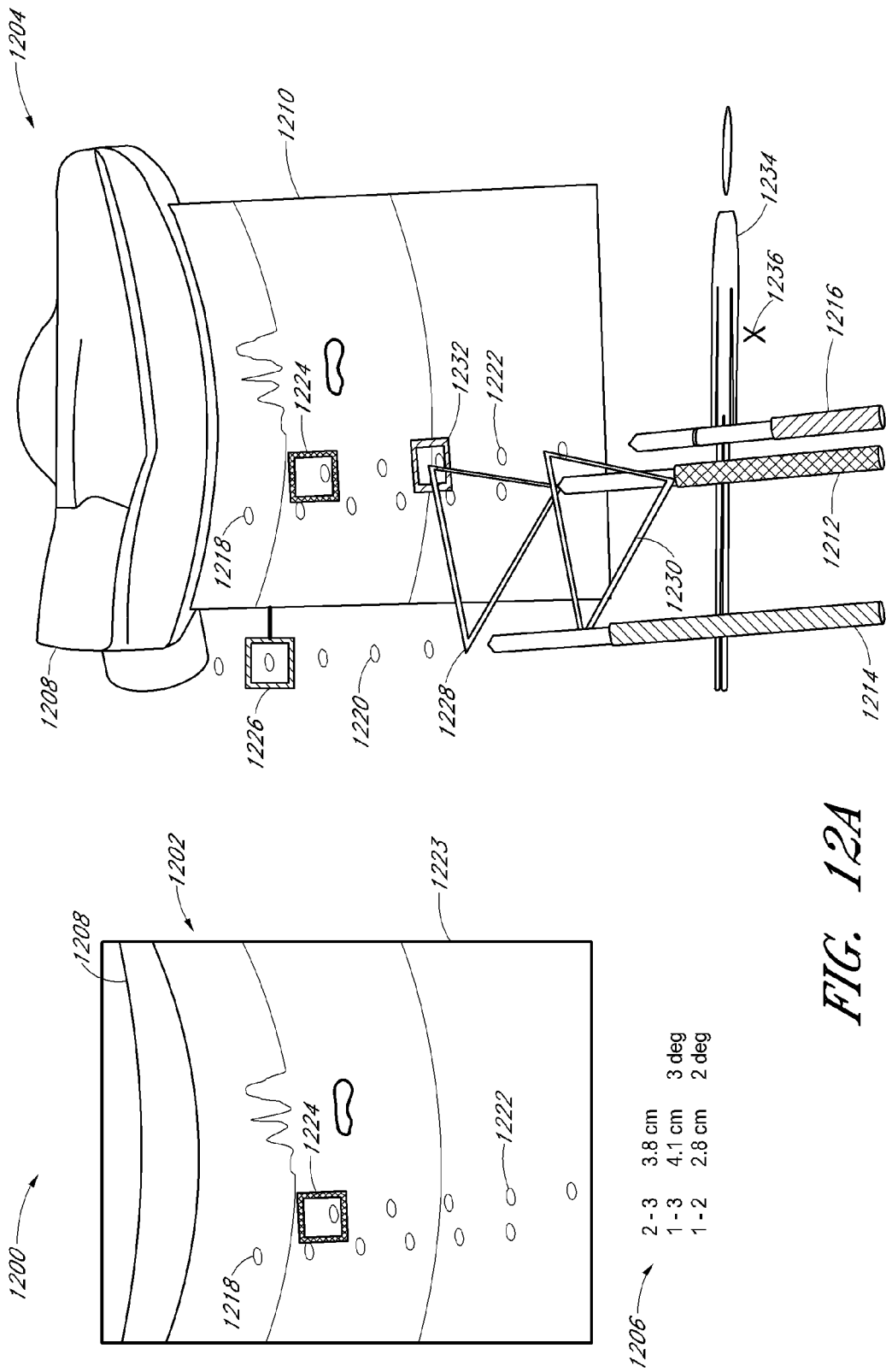

Although three medical devices 1212, 1214, 1216 are displayed, it will be understood that fewer or more medical devices can be used and displayed as desired. In addition, it will be understood that in some embodiments not all of the features shown in FIG. 12A are present in the 3D image display area 1204. For example, in some embodiments, any one or any combination of the features described above can be included in the 3D image display area 1204.

The multiple virtual medical devices 1212, 1214, 1216, can be implemented by tracking emplacement information of multiple real medical devices located within a predetermined area. The predetermined area can correspond to a location of a medical procedure, the location of a patient, the location of tracking units, the range of position sensing units, a surgical table, an area corresponding to a virtual 3D area displayed on a display etc. Tracking emplacement information for a medical device is described in greater detail above with reference to FIGS. 1A and 1B. For example, a tracking unit can be associated with each medical device and provide emplacement information for the medical device. The system can use the emplacement information of the medical devices to generate the display illustrated in FIG. 12A. Furthermore, as described previously with reference to FIGS. 2-10, any one or any combination of cues can be displayed for each of the medical devices 1212, 1214, 1216.

In some embodiments, each medical device and its associated image guidance cues (e.g. trajectory rings, intersection square, text, etc.) can be associated with a color. In some embodiments, each medical device with its associated image guidance cues is associated with a different color. For example, the first medical device 1212 and image guidance cues related to it can be drawn in pink, a second medical device 1214 and its associated image guidance cues can be drawn in green, and a third medical device 1216 and its associated image guidance cues can be drawn in blue. It will be understood that any combination of colors can be used as desired. Furthermore, the medical devices and associated image guidance cues can be distinguished based on different patterns or markings. For example, the system can cause the medical devices to have zigzags, lines, be bolded, flicker, etc.

Foundational Plane Indicators

In some embodiments, the image guidance cues can include foundational plane indicators, such as foundational plane indicators 1228, 1230 and foundational plane intersection indicators, such as foundational plane intersection indicator 1232. The foundational plane indicators 1228, 1230 can indicate a location of a foundational plane and/or indicate a location where secondary medical devices are to be placed in order to be level with the foundational medical device. In some embodiments, the foundational plane indicators 1228, 1230 can also indicate how the medical devices are to be placed so they are parallel to each other. The foundational plane intersection indicators (e.g., foundational plane intersection indicator 1232) can indicate a location where the trajectory of a medical device intersects a foundational plane.

In the illustrated embodiment of FIG. 12A, the first medical device 1212 is selected as the foundational medical device. As mentioned previously, the foundational medical device can be the first medical device placed in the tissue and or selected by the user. Once the foundational medical device is selected, the system can calculate one or more foundational planes, as described in greater detail above with reference to FIG. 11, and can generate foundational plane indicators. In the illustrated example of FIG. 12A, the 3D image display area 1204 includes a foundational tip plane indicator 1228 and a foundational electrode plane indicator 1230. However, it will be understood that in some embodiments only one foundational plane indicator is displayed. Furthermore, in certain embodiments, three or more foundational plane indicators can be displayed.

In the illustrated embodiment, the foundational tip plane indicator 1228 extends from the tip of the foundational medical device 1212 to locations on the foundational tip plane where the tips secondary medical devices 1214, 1216, are to be placed. Accordingly, a user can use the foundational tip plane indicator 1228 to identify the location where the secondary medical devices 1214, 1216 are to be located to be level with the foundational medical device 1212. In certain embodiments, the foundational electrode plane indicators can indicate the location where the trajectories of the secondary medical devices intersect the foundational plane.

In some embodiments, the desired location for the tips of the secondary medical devices on the foundational tip plane is determined based on user input. For example, the user can indicate at what distances and locations the secondary medical devices are to be placed with respect to the foundational medical device. Based on the input, the system can determine the appropriate shape and size of the foundational tip plane indicator. In certain embodiments, the system dynamically calculates the location for the tips of the secondary medical devices on the foundational tip plane based on an identified object, such as a tumor, fibroid, etc., the size of the identified object, the number of medical devices to be used, electrical power specifications of the medical devices, etc.

In the illustrated embodiment of FIG. 12A, the foundational tip plane indicator 1230 creates a triangular shape because three medical devices are used. However, it will be understood that the shape created by the foundational tip plane indicator 1228 can be any shape or line, and in some embodiments, is based at least in part on the number of medical devices used. For example, the foundational tip plane indicator 1228 can create a line when two medical devices are used (or when one medical device is selected as described in greater detail below in FIGS. 12B and 12C), a quadrilateral (e.g., square, rectangle, parallelogram, kite, etc.) when four medical devices are used, a pentagon when five medical devices are used, a hexagon when six medical devices are used, etc.

The foundational electrode plane indicator 1230 extends from the electrode of the foundational medical device 1212 to locations on the foundational electrode plane where the electrodes of secondary medical devices are to be placed. In the illustrated embodiment of FIG. 12A, the foundational electrode plane indicator 1230 extends from a location on the foundational medical device 1212 where the electrode ends. However, it will be understood that the foundational electrode plane indicator 1230 can extend from any location on the foundational medical device. As described above, with reference to the foundational tip plane indicator 1230, the foundational electrode plane indicator 1230 location and shape of the foundational electrode plane indicator 1230 can be determined based on user input, the number of medical devices used, and/or dynamically.

The foundational plane intersection indicator 1232 can be used to indicate where the trajectory of a medical device intersects with a foundational plane, or where a medical device will be if it is moved forward. In the illustrated embodiment of FIG. 12A, the display 1200 includes foundational plane intersection indicator 1232 indicating the intersection of the foundational tip plane and the trajectory of the medical device 1216. However, it will be understood that a foundational plane intersection indicator can be used to indicate the intersection of any foundational plane with a trajectory of any medical device.

In some embodiments, the guidance cues (e.g., trajectory indicators, intersection indicators, etc.) associated with one or more medical devices are displayed simultaneously. In certain embodiments, the guidance cues associated with each medical device are displayed only when the associated medical device is selected. For example, in the illustrated embodiment of FIG. 12A, the medical device 1216 is selected. Accordingly, the foundational plane intersection indicator 1232 indicates the intersection of the trajectory of the medical device 1216 and the foundational tip plane, and the image plane intersection indicator 1226 indicates the intersection of the trajectory of the medical device 1216 and the image plane.

Patient and Provider Indicators

The patient orientation indicator 1234 can indicate the orientation of the patient with respect to the perspective view of the 3D image display area 1204. In the illustrated embodiment of FIG. 12A, the patient orientation indicator 1234 indicates that the head of the patient is on the right side with respect to the image 1210. In addition, in the illustrated embodiment of FIG. 12A, the patient orientation indicator 1234 is implemented as a human figure, however, it will be understood that the patient orientation indicator 1234 can be implemented as any number of graphical indicators, such as a line, an arrow, a shape, etc. For example, an arrow can point in the direction of the head of a patient, or a shape or letter can be used to indicate the location of the head, feet, or other part of the patient. Furthermore, in some embodiments, the 3D image display area 1204 does not include the patient orientation indicator 1234.

In some embodiments, the display 1200 can include a provider indicator 1236 that indicates the location of a medical provider with respect to the patient. The provider indicator can be implemented as a dot, shape, color, arrow, line, or any other graphical indicator to indicate the location of the medical provider with respect to the patient. The system can determine the location of the provider based on user input and/or dynamically based on one or more tracking units associated with the medical provider.

In certain embodiments, the location of the medical provider coincides with the perspective view of the virtual 3D space. In the illustrated embodiment of FIG. 12A, the provider indicator indicates that the medical provider is located in front of the patient with respect to the perspective view. With reference to FIG. 12C, the provider indicator 1236 indicates that the medical provider is located behind the patient with respect to the perspective view.

Emplacement Measurement Display Area

The emplacement measurement display area 1206 can provide a user with information regarding the emplacement of the medical devices. In some embodiments, the emplacement measurement display area 1206 provides relative emplacement information of the medical devices. For example, the emplacement measurement display area 1206 can indicate relative distances between the medical devices, relative degrees between the medical devices, etc. The relative distances between the medical devices can include the distance between the ends of the medical devices, the distance between other corresponding portions of the medical devices, the horizontal distance between corresponding portions of medical devices (e.g., the distance between a tip of the foundational medical device and the tip of the second medical device if the tip of the second medical device was on the foundational tip plane), the vertical distance between corresponding portions of medical devices (e.g., the distance between the foundational tip plane and the tip of a second medical device), etc. The relative degrees between the medical devices can include the difference in degrees between the longitudinal axis of one medical device and the longitudinal axis of another medical device or some other axis of the medical devices. The emplacement measurement display area 1206 can include any one of or any combination of the distances and/or degrees described herein.

In the illustrated embodiment of FIG. 12A, the emplacement measurement display area 1206 includes the relative emplacement information of the medical devices 1212, 1214, 1216, with respect to one another. For example, the emplacement measurement display area 1206 indicates that the tips of the medical devices 1214 (referenced by the '2') and 1216 (referenced by the '3') are 1.8 cm apart and are parallel. The emplacement measurement display area 1206 also indicates that the tips of the foundational medical device 1212 (referenced by the '1') and the medical device 1216 (referenced by the '3') are 2.1 cm apart and 1 degrees off from one another (i.e., there is a 1 degree difference between the longitudinal axis of the foundational medical device 1212 and the medical device 1216). The emplacement measurement display area 1206 further indicates that the tips of the foundational medical device 1212 (referenced by the '1') and the medical device 1214 (referenced by the '2') are 2.8 cm apart and 2 degrees off from one another. As mentioned previously, any one of, or any combination of, the emplacement information described previously can be included in the emplacement measurement display area 1206. For example, the emplacement measurement display area 1206 can include the relative horizontal difference between portions of the medical devices and/or the relative vertical distances between portions of the medical devices, etc.

In some embodiments, the text indicating the distance between the tips of a pair of medical devices can be drawn in a first color (e.g., white) if it satisfies a threshold distance (e.g., 2 cm), and a second color (e.g., red) it does not. Similarly, the angles can be drawn in the first color if they meet a threshold angle (e.g., 10 degrees), and the second color if they do not. It will be understood that other color schemes can be used as well. In some embodiments, the medical device numbers can be included next to the distances and angles, and in certain embodiments, the number of the medical device can be color-coded similar to the image guidance cues discussed previously.

Relative Location Indicators

As illustrated in FIG. 12B, in certain embodiments, relative location indicators, such as relative location indicators 1238, 1240, can be used in place of, or in any combination with, one or more foundational plane indicators, such as foundational plane indicators 1228, 1230 of FIG. 12A. The relative location indicators 1238, 1240 can indicate the relative locations of corresponding locations of the medical devices. For example, the relative location indicators 1238, 1240 can indicate the relative locations between the ends of the medical devices (e.g., location indicators 1238), the exposed electrodes of the medical devices (e.g., location indicators 1240) or other locations of the medical devices. Furthermore, the relative location indicators can be implemented as any graphical indicator between the corresponding locations of the medical devices. For example, the relative location indicators can be implemented as lines, bars, etc. between the corresponding locations of the medical devices. Furthermore, the shape of the location indicators can be any shape, as described in greater detail above with reference to FIG. 12A.

In the illustrated embodiment of FIG. 12B, the relative location indicators include a relative tip location indicator 1238 and a relative electrode location indicator 1240, and are implemented as bars between the corresponding locations of the medical devices. The relative tip location indicator 1238 indicates the relative location of the tips of each of the medical devices 1212, 1214, 1216 with respect to one another and the relative electrode location indicator 1240 indicates the relative location of the ends of the exposed electrodes of each of the medical devices 1212, 1214, 1216 with respect to one another. It will be understood that in some embodiments, any one of, or any combination of, the relative tip location indicator 1238 and a relative electrode location indicator 1240 can be included in the display 1200. Furthermore, it will be understood that other relative location indicators can be used in place of, or in any combination with, the relative tip location indicator 1238 and/or the relative electrode location indicator 1240.

Multiple Medical Device Guidance—Relative Spatial Relationships

When multiple medical devices are depicted in 2D or 3D, it can be difficult to determine when the medical devices are parallel. Similarly, it can be difficult to determine the relative angle between a longitudinal axis of the foundational medical device and the longitudinal axis of another medical device. It can also be difficult to determine the distance between various portions of the foundational medical device and corresponding portions of a secondary medical device.

Figure 12D:
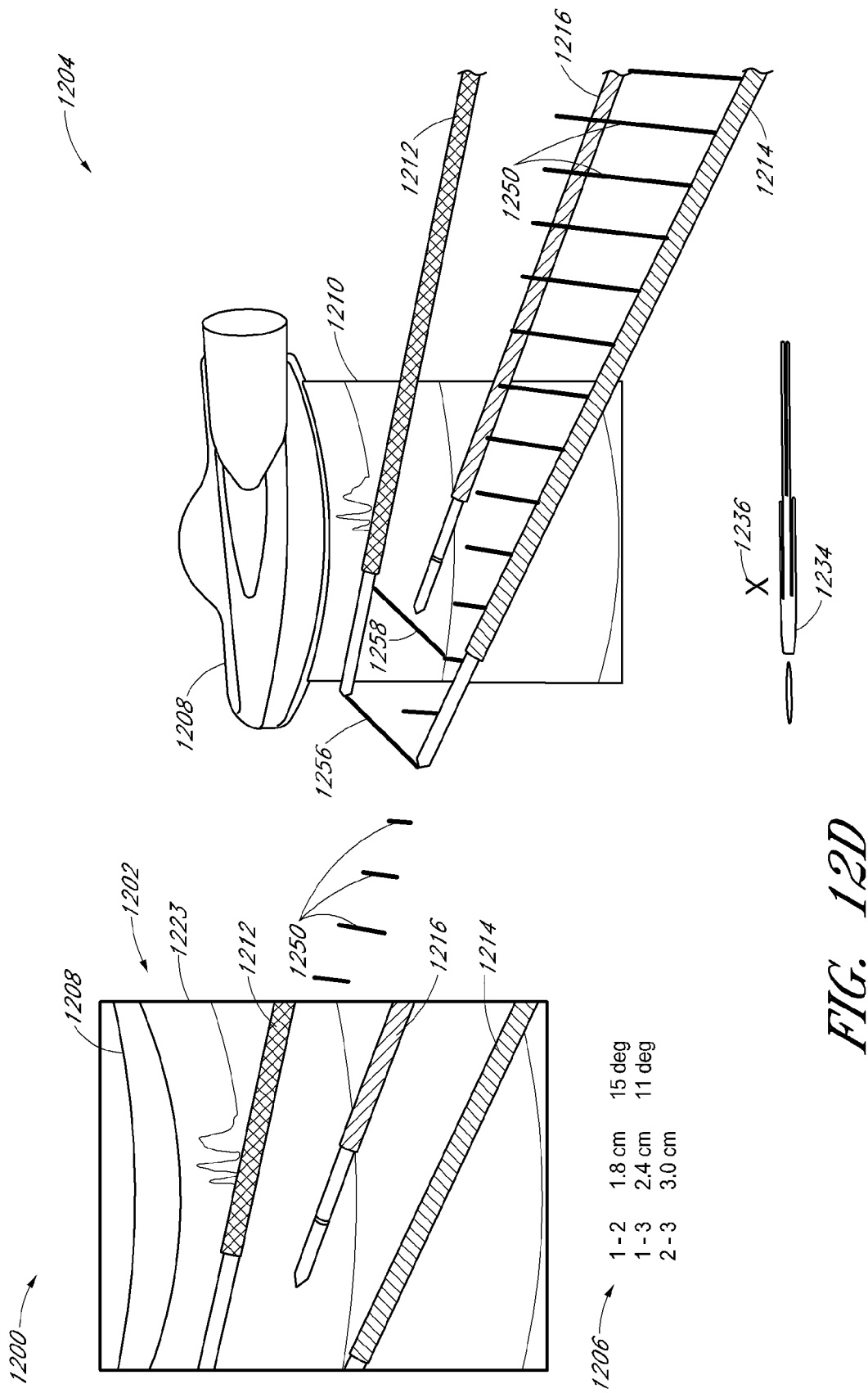

FIGS. 12C and 12D are diagrams illustrating the display 1200 with graphical indicators that indicate spatial relationships. For simplicity, the graphical cues described above with reference to FIGS. 12A and 12B are not shown. However, it will be understood, any one or any combination of the features described with reference to FIGS. 12A and 12B can be included as part of the embodiments described herein with reference to FIGS. 12C and 12D. Furthermore, as mentioned previously, in some embodiments only some of the features described herein are present. For example, in some embodiments, the display 1202 only includes the 3D image display area 1204.

Furthermore, in the illustrated embodiment of FIG. 12C, the medical device 1216 is selected for placement. Based on this selection, only the guidance cues associated with the medical device 1216 are displayed. However, it will be understood that similar guidance cues can be displayed for the other secondary medical device 1214, as illustrated in FIG. 12C. Furthermore, although illustrated as being displayed separately, it will be understood that the guidance cues for more than one secondary medical device and/or the foundational medical device can be displayed simultaneously.

In the illustrated embodiment, the guidance cues include relative spatial indicators 1250 and foundational plane indicators 1252, 1254. The relative spatial indicators 1250 indicate the distance between portions of a longitudinal axis of the secondary medical device 1216 and portions of a target axis or target plane. In some embodiments, the target axis can be the axis at which the secondary medical device 1216 is to be placed. The target axis can be based on user input, such as where the user wants the secondary medical device 1216 to be placed and/or dynamically based on the emplacement of the foundational medical device 1212. In certain embodiments, the target axis or target plane is parallel to the longitudinal axis of the foundational medical device 1212. In some embodiments the target plane is the image plane, described previously.

In some embodiments, the relative spatial indicators 1250 indicate the relative distance between portions of the secondary medical device 1216 and the longitudinal axis of the foundational medical device 1212. In certain embodiments, the relative spatial indicators 1250 can indicate the distance from portions of the secondary medical device 1216 to corresponding portions of the foundational medical device 1212.

As the secondary medical device 1216 is moved closer to, or farther away from, the target axis or target plane, the spatial indicators 1250 can shorten or lengthen, respectively. If the secondary medical device 1212 is placed at the target axis or target plane, the spatial indicators 1250 can disappear. In some embodiments, if the secondary medical device 1212 is parallel to the target axis or target plane, the spatial indicators 1250 can be equal in length. However, if the secondary medical device 1216 is angled with respect to the target axis, the spatial indicators 1250 can have different lengths.

In the illustrated embodiment of FIGS. 12C and 12D, the spatial indicators 1250 are shown as rectangular bars, however, it will be understood that the spatial indicators 1250 can be implemented as any one of, or a combination of, bars, dashed lines, solid lines, symbols, etc.

In the illustrated embodiment of FIG. 12C, the foundational plane indicators 1252, 1254 include a foundational tip plane indicator 1252 and a foundational electrode plane indicator 1254. It will be understood that in some embodiments, only one foundational plane indicator is displayed and in certain embodiments more than two foundational plane indicators are displayed.

The foundational plane indicators 1252, 1254 are similar to the foundational plane indicators 1228, 1230 described above with reference to FIGS. 12A and 12B. However, as illustrated, the foundational plane indicators 1252, 1254 are graphical bars instead of shapes and indicate the location of the foundational plane with respect to the selected medical device (e.g., the medical device 1216) and do not indicate the location of the foundational plane with respect to the other secondary medical device (medical device 1214). However, as illustrated in FIG. 12D, when the secondary medical device 1214 is selected, corresponding foundational plane indicators 1256, 1258 can be displayed. As mentioned previously, the graphical cues associated with the different medical devices can be displayed simultaneously.

In some embodiments, the foundational plane indicators 1252, 1254 can indicate when the secondary medical device 1216 is parallel with the foundational medical device 1212 and/or indicate when the secondary medical device 1216 is level with the foundational medical device 1212. For example, the end of each foundational plane indicator 1252, 1254 can include a line that indicates at what angle the medical device is to be placed in order to be parallel to the target plane or target axis. In certain embodiments, a number indicating the relative difference in degrees can be provided as part of the foundational plane indicators 1252, 1254.

It will be understood that any one, or any combination, of the embodiments described above with respect to the foundational plane indicators of FIGS. 12A and 12B can be used in place of, or in conjunction with, any of the embodiments of the foundational plane indicators 1252, 1254 described above with reference to FIGS. 12C and 12D.

Multiple Medical Device Guidance Routine

Figure 13:
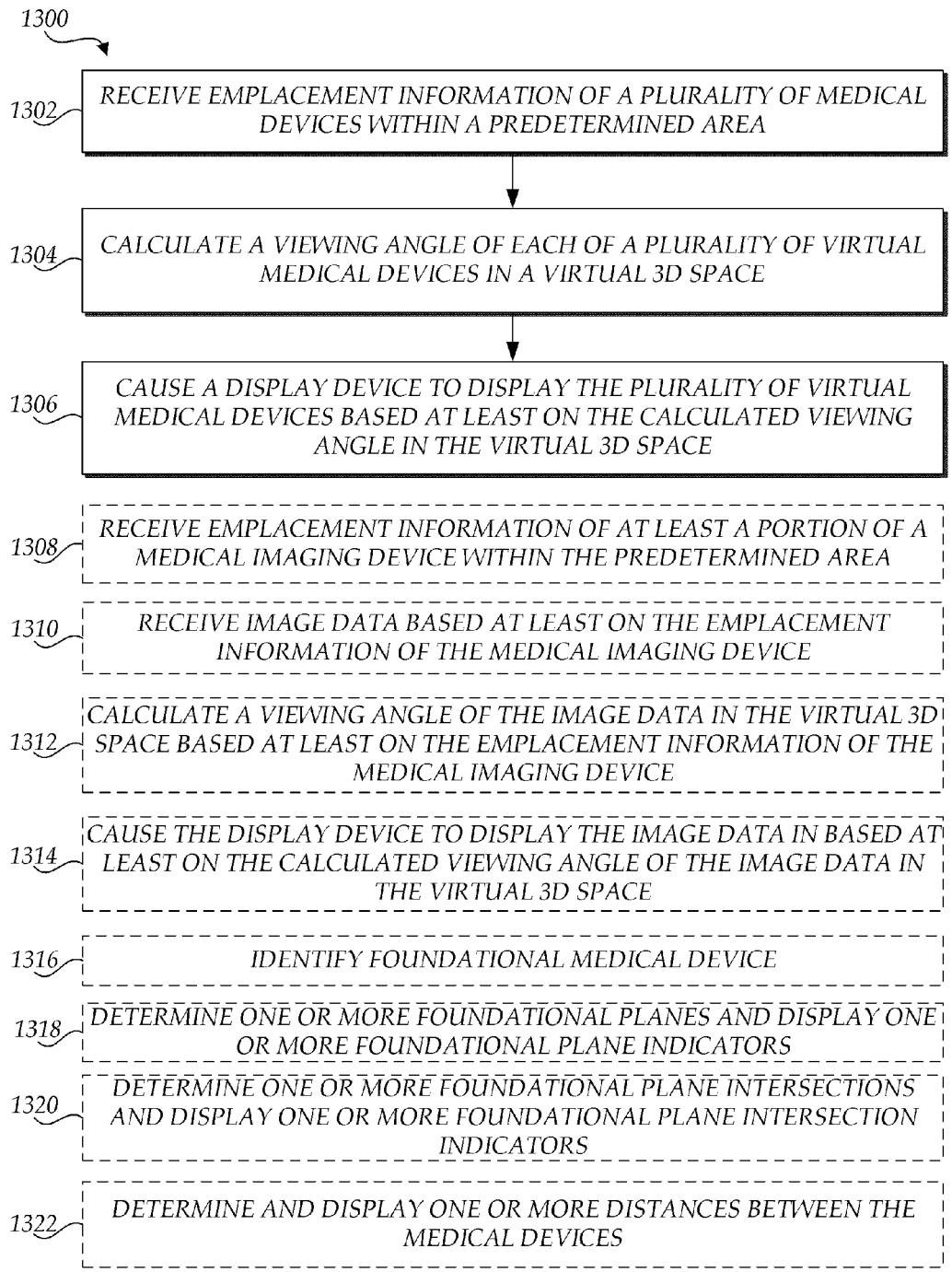
FIG. 13 is a flow diagram illustrative of an embodiment of a routine implemented by the system to display a plurality of virtual medical devices.

FIG. 13 is a flow diagram illustrative of an embodiment of a routine 1300 implemented by the system 100 to display a plurality of virtual medical devices. One skilled in the relevant art will appreciate that the elements outlined for routine 1300 can be implemented by one or more computing devices/components that are associated with the system 100, such as the position sensing units 110, 140, the image guidance unit 130, surgical system 149, and/or imaging unit 150. Accordingly, routine 1300 has been logically associated as being generally performed by the system 100. However, the following illustrative embodiment should not be construed as limiting.

At block 1302, the system 100 receives emplacement information of a plurality of medical devices within a predetermined area. In some embodiments, the medical devices are invasive medical devices, such as ablation or biopsy needles, catheters, etc. As described previously, the medical devices, such as needles, can include tips, electrodes, and handles. In certain embodiments, the medical devices are non-invasive medical devices. In some embodiments, the medical devices are medical imaging devices, such as ultrasound transducers and/or laparoscopic cameras.

As described in greater detail above with reference to FIGS. 1A and 1B, each medical device can be associated with a tracking unit that provides emplacement information, such as position and orientation information. As described previously, the tracking units can be affixed to or implanted into the medical devices. Using the emplacement information of the tracking unit and known characteristics of the medical devices, the emplacement information can be determined. Accordingly, by receiving emplacement information from a tracking unit, the system 100 can also receive and/or determine emplacement information of the medical device.

At block 1304, the system 100 calculates a viewing angle in a virtual 3D space of a plurality of virtual medical devices. The virtual medical devices can correspond to the medical devices that are being tracked. Further, the viewing angle can be based at least on the emplacement information of the plurality of medical devices. In some embodiments, the system calculates a viewing angle for each of the medical devices. In certain embodiments, to calculate the viewing angle, the system determines the emplacement of the medical devices with respect to a perspective view.

As mentioned previously with reference to FIG. 2, the system 100 can use the emplacement information of the plurality of medical devices with respect to the perspective view to determine how the virtual medical devices are to be displayed on a display. The perspective view can be determined based on user input and/or dynamically based on a position of the healthcare provider with respect to the display device and/or the medical devices. In some embodiments, the perspective view corresponds to the position of the healthcare provider with respect to the medical devices and/or or with respect to the display. In addition, as discussed in greater detail with reference to FIG. 11, the perspective view can be based on the number and location of the virtual medical devices as well.

At block 1306, the system 100 causes a display device to display the plurality of virtual medical devices based at least on the calculated viewing angle(s) in the virtual 3D space. Based on the calculated viewing angle(s) and the perspective view, the system 100 can cause the display to display the medical devices with respect to one another. As the system 100 can calculate the viewing angle for each virtual medical device separately, each virtual medical device can be displayed at a different angle with respect to the perspective view. As mentioned previously, the perspective view can be based on the location of the healthcare provider, the location of an image in the virtual 3D space, the location and number of medical devices, etc.

As the position and orientation of the medical devices change, the system 100 can display the change with respect to the perspective view. For example, if the longitudinal axis of a virtual medical device is displayed as being left to right on the display and the medical device is rotated 90 degrees around the z-axis, the system 100 will change the display to show the longitudinal axis of the virtual medical device as being from the foreground to the background (or front to back).

Additional, fewer, or different blocks can be used to implement the routine 1300 without departing from the spirit and scope of the description. For example, any one or a combination of blocks 1308-1322 can be used as part of routine 1300.

At block 1308, the system 100 receives emplacement information of a medical imaging device within the predetermined area. As described previously, the medical imaging device can be an ultrasound transducer, laparoscopic camera, etc. Similar to the receipt of emplacement information described above with reference to block 1302, the system 100 can receive emplacement information of the medical imaging device.

At block 1310, the system 100 receives image data based at least on the emplacement information of the medical imaging device. In some embodiments, system receives one or more images from the medical imaging device. For example, the medical imaging device can be an ultrasound transducer and can provide one or more ultrasound images to the system 100. As described in greater detail above with reference to FIGS. 1A and 1B, in some embodiments, the medical imaging device is used to select image data from a set of image data stored previously. For example, based on the emplacement of the medical imaging device, the system can receive images corresponding to a CT scan or MRI. In such embodiments, any device can be used as the medical imaging device.

At block 1312, the system 100 calculates a viewing angle in the virtual 3D space of the image data (e.g., one or more images) based at least on the emplacement information of the medical imaging device. As described previously with reference to block 1304, the system can calculate viewing angles in the virtual 3D space based on the emplacement information of the medical imaging device with respect to the perspective view. Using this information, the system 100 can calculate a viewing angle for image data in the virtual 3D space.

At block 1314, the system 100 causes the display device to display the image data based at least on the calculated viewing angle in the virtual 3D space. As described previously with reference to block 1306 the system can cause a display device to display images based on the calculated viewing angle. Similarly, the system 100 can cause the display device to display the image data (e.g., one or more images).

At block 1316, the system 100 identifies a foundational medical device. As described in greater detail above with reference to FIGS. 12A and 12B, the system 100 can identify the foundational medical device from among the medical devices being tracked. In some embodiments, the foundational medical device is the first medical device that is placed in the patient.

At block 1318, the system 100 determines one or more foundational planes and displays one or more foundational plane indicators, as described in greater detail above with reference to FIGS. 12A and 12B. As further described previously, the foundational planes can include a foundational tip planes, foundational electrode planes, etc. Once the foundational planes are determined, the system 100 can cause the display device to display foundational plane indicators corresponding to the foundational planes. The foundational plane indicators can indicate relationships between secondary medical devices and the foundational plane and between the foundational medical device and the foundational plane.

Such information can be useful to a healthcare provider when placing the secondary medical devices. For example, the foundational plane indicators can indicate the location at which a secondary medical device is to be placed to be level with the foundational medical device (e.g., corresponding portions, such as the tip or handle, of the two medical devices are parallel).

At block 1320, the system 100 determines one or more foundational plane intersections and displays one or more foundational plane intersection indicators. As described in greater detail above with reference to FIGS. 12A and 12B, the system 100 can determine the points of intersection between the axis of the virtual medical devices and the foundational plane based on the emplacement information of the medical devices. Once determined, the system 100 can display indicators for those intersections. Using the indicators, the healthcare provider can identify where a medical device will intersect the foundational plane if pushed forward. Based on the desired placement of the medical device, the healthcare provider can change the position and orientation of the medical device as desired. Thus, the indicators can aid a healthcare provider during the placement of a medical device. Furthermore, the system can calculate distances between the foundational planes and the tips of the medical devices or other portions of the medical devices. The calculated distances can be displayed and/or used to display the medical devices.

At block 1322, the system 100 determines and displays one or more distances between the medical devices. As described in greater detail above with reference to FIGS. 12A and 12B, the system 100 can use the emplacement information to determine various distances between the medical devices. For example, the system 100 can determine the distance between the tips of two or more medical devices, the horizontal distance between two or more medical devices, and/or the vertical distance between two or more medical devices. The system 100 can display the distances as numbers and/or as graphical indicators as described above.

Furthermore, additional blocks can be used as part of the routine 1300. As described in greater detail above with reference to FIGS. 12A and 12B, the system 100 can determine and display many different parameters using the emplacement information of the multiple medical devices, such as angular differences between medical devices, trajectory intersections with an image plane, distances between the foundational plane and secondary medical devices, relative location differences of different portions of the medical devices with respect to target axis or target planes, and relative size of portions of the medical devices with respect to a target region. The angular differences between the axes of the medical devices can be displayed as a number or graphically as bars or lines between medical devices. The angular differences can be used to determine when two medical devices are parallel. The intersections of the trajectory of medical devices with an image plane can be indicated on the display to aid a healthcare provider in the placement of the medical device. The distances between the foundational plane and secondary medical devices can be displayed numerically or graphically and can aid the healthcare provider in placing the secondary medical devices with respect to the foundational medical device. The relative locations between different portions of the medical devices with respect to a target axis or target plane can be displayed graphically as described in greater detail above, with reference to FIGS. 12C and 12D, and used by a healthcare provider to aid in the placement of the medical devices. The relative size of portions of the medical device with respect to a target region can be displayed graphically, as described in greater detail below with reference to FIG. 14A and can help a healthcare provider determine whether the medical device is large enough to treat a target, such as a tumor.

Figure 14A:
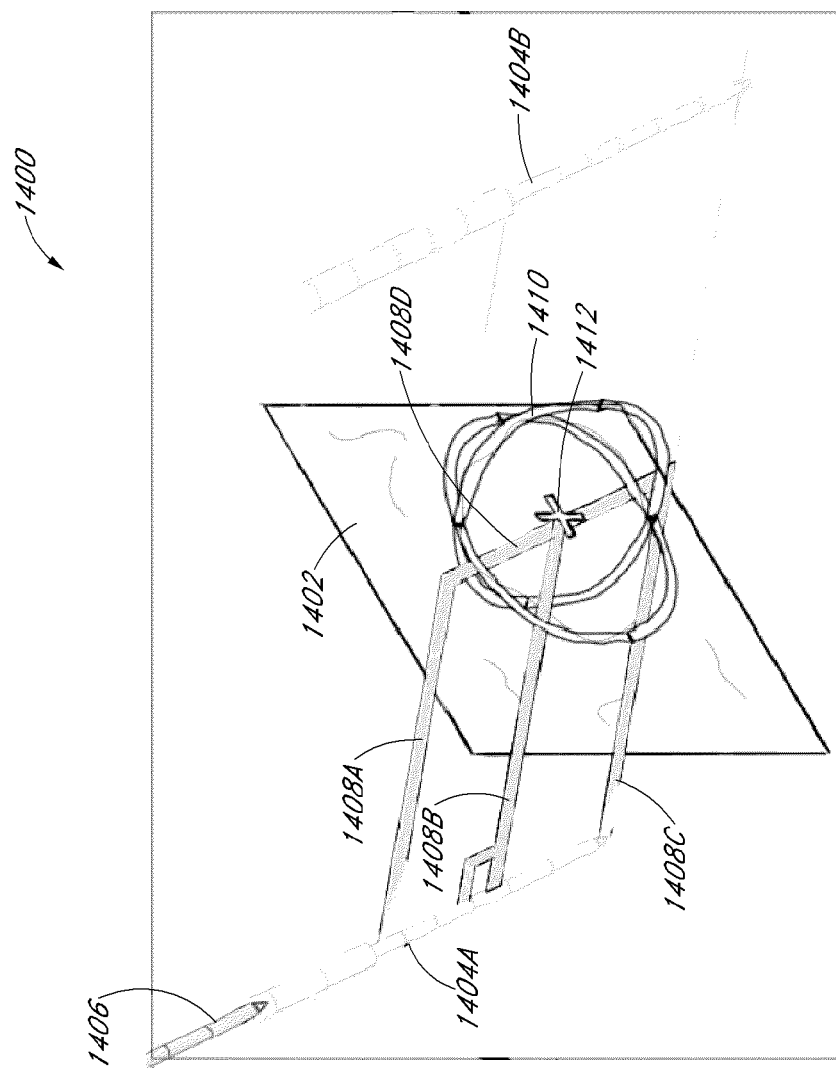
FIG. 14A is a perspective view of an embodiment of a display for medical device placement guidance.

In addition, as described above with reference to FIGS. 12A-12D, the system 100 can cause the display device to display a second set of the image data (e.g., in the Medical Device Guidance—Planning Mode FIG. 14A is a perspective view of an embodiment of a display in which the system provides medical device placement guidance to a user. In the illustrated embodiment, the display 1400 includes an image 1402, medical device placement suggestions 1404A and 1404B, a virtual medical device 1406, and guidance cues 1408, 1410, 1412. Furthermore, any one or any combination of the guidance cues described above with reference to FIGS. 2-11 and 12A-12D can be used in conjunction with any of the embodiments described herein with reference to FIGS. 14A and 14B. For example, the system can identify one of the medical devices or one of the suggested placements as the foundational medical device and can calculate and display the various guidance cues associated with the foundational plane, etc. Furthermore, it will be understood that although described in the context of providing guidance for the placement of multiple medical devices, the embodiments described herein can provide guidance for the placement of a single medical device with respect to a target region.

The guidance cues in the illustrated embodiment include the center of the tumor marker 1412, which can be manually placed by a user, and tumor boundary markers 1410 which indicates the extents or boundary of the tumor in two perpendicular planes. As described in greater detail above with reference to FIGS. 8, 9, and 10A-10D, a user can mark and/or annotate images. The system 100 can store the emplacement information of the markers and annotations in the virtual 3D space.

The guidance cues in the illustrated embodiment also include draws bars 1408A-1408D, which can be generated by the system after the user has marked the center of the tumor (or other point in the tumor) and the boundary of the tumor. The system can calculate the location of the draw bars based on the suggested placement of a medical device, the length of the exposed electrode of the medical device and/or different locations within the exposed electrode of the medical device (e.g., tip, center, and end).

In the illustrated embodiment, the draw bars include draw bar 1408A between the end of the exposed electrode of the virtual medical device 1406 (when placed at the placement suggestion 1404A) and the image 1402, draw bar 1408B between the center of the exposed electrode of the medical device 1406 (when placed at the placement suggestion 1404A) and the center of the tumor marker 1412, draw bar 1408C between the tip of the virtual medical device 1406 (when placed at the placement suggestion 1404A) and the image 1402, and draw bar 1408D parallel to the exposed electrode of the virtual medical device (when placed at the placement suggestion 1404A), but running through the previously marked center of the tumor.

The draws bars 1408A-1408D can show the user 1) if the exposed electrode is long enough to cover the extent/boundary of the tumor, 2) if the exposed electrode is centered with respect to the tumor, and 3) the distance between the tumor-center and the electrode. This distance can also be displayed numerically on the screen (not shown).

In addition, the system can display placement suggestions 1404A, 1404B for the medical devices. The system can generate the placement suggestions 1404A, 1404B and number of placement suggestions based on: 1) the distance between the first medical device (after placement) and the tumor-center 2) the length of the exposed electrodes of the medical devices, 3) a model of the ablation parameters of the medical device (e.g. a lookup table), 4) tumor size, etc. In illustrated example, the system suggests a configuration of two medical devices.

In the illustrated embodiment, the placement suggestions 1404A, 1404B are illustrated as faded virtual medical devices, however, it will be understood that other method can be used to provide the placement suggestions. For example, the placement suggestion 1404A, 1404B can be illustrated as lines, bars, cylinders, letters (e.g., X's), etc.

Furthermore, when the medical device 1406 is close to, or enters the predetermined area, the system can generate the virtual medical device 1406 and the user can guide the virtual medical device 1406 to the placement suggestion 1404A. The system's proposed configuration can be repeatedly updated as the user manipulates the first medical device (still outside the patient), until she accepts the proposed position.

Figure 14B:
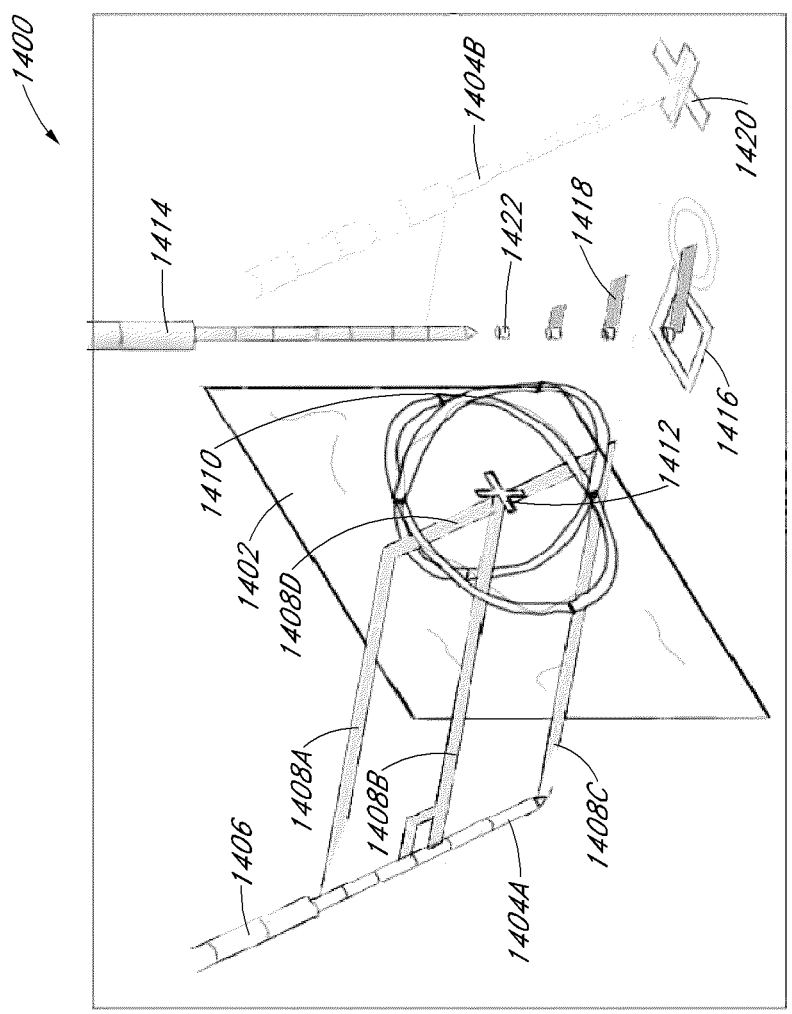
FIG. 14B illustrates the content on a display 1500 in certain embodiments depicting manipulation of a second medical device with respect to a target region.

FIG. 14B illustrates the content on a display 1400 in certain embodiments depicting manipulation of the second medical device in context with the target region. Here, the first medical device has already been placed as indicated by the location of the first virtual medical device 1406, and the system provides the user with the placement suggestion 1404B for the second medical device.

The second virtual medical device 1414 is in a vertical orientation, and the user manipulates the second medical device corresponding to the second virtual medical device 1414 (e.g., while it is outside the patient) such that the intersection indicator 1416 (described in FIGS. 12A and 12B) is co-located with the suggested intersection indicator 1420 that the system displays at the tip of the placement suggestion 1404B. Once this is achieved, the second medical device will be lined up with its trajectory directly toward the placement suggestion 1404B. The user can then push the second medical device into the patient tissue until the system displays the tip of the second virtual medical device 1414 at the suggested intersection indicator 1420. To aid a user in the placement of the second virtual medical device, the system includes relative spatial indicators 1418 and trajectory indicators 1422, as described in greater detail above with reference to FIGS. 12A-12D.

Medical Device Guidance—Planning Routine

Figure 15:
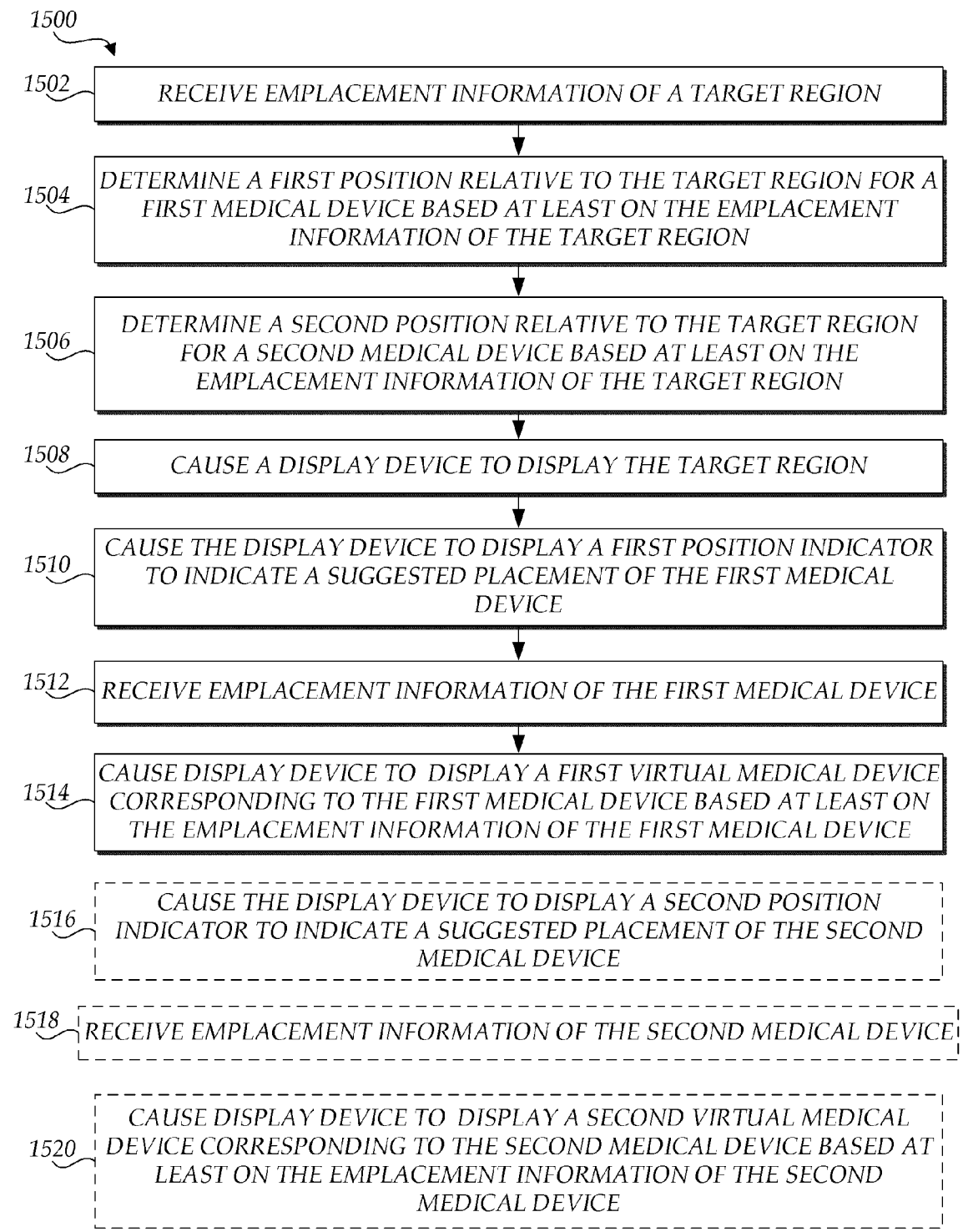
FIG. 15 is a flow diagram illustrative of an embodiment of a routine implemented by the system to provide medical device placement guidance.

FIG. 15 is a flow diagram illustrative of an embodiment of a routine 1500 implemented by the system 100 to provide medical device placement guidance. The medical devices can include invasive medical devices, non-invasive medical devices, and/or medical imaging devices. In some embodiments, the medical devices include ablation and/or biopsy needles. One skilled in the relevant art will appreciate that the elements outlined for routine 1500 can be implemented by one or more computing devices/components that are associated with the system 100, such as the position sensing units 110, 140, the image guidance unit 130, surgical system 149, and/or imaging unit 140. Accordingly, routine 1500 has been logically associated as being generally performed by the system 100. However, the following illustrative embodiment should not be construed as limiting.

At block 1502, the system 100 receives emplacement information associated with a target region. The emplacement information associated with the target region can be based on a marker or annotation placed by a healthcare provider as described earlier with reference to FIGS. 8, 9, and 10A-10D. The system can use the emplacement of the marker and/or annotation to determine the emplacement of the target region. In some embodiments, the emplacement information is received during a medical procedure. In certain embodiments, the emplacement information is received prior to a medical procedure.

At block 1504, the system 100 determines a first position relative to the target region for a first medical device based at least on the emplacement information of the target region. As described in greater detail above with reference to FIGS. 14A and 14B, the system 100 can determine a suggested placement of a first medical device with respect to the target region. As described previously, the suggested placement can be based on the length of the exposed electrodes of the medical device a model of ablation parameters, tumor size, number of medical devices to be used, etc.

At block 1506, the system 100 determines a second position relative to the target region for a second medical device. As mentioned previously the second position can be based on the emplacement information of the target region, the emplacement information of the first position, and/or any one or any combination of the parameters described above with reference to FIGS. 14A and 14B.

At block 1508, the system 100 causes a display device to display the target region, as described in greater detail above with reference to FIGS. 14A and 14B. The display can be based on a calculated viewing angle in a virtual 3D space, described in greater detail above with reference to FIGS. 2, 5, and 12A-12D, of the target region.

At block 1510, the system 100 causes the display device to display a first position indicator. The system can cause the display device to display the first position indicator at the first position. As discussed previously with reference to FIGS. 14A and 14B, the first position indicator can be in the form of the first virtual medical device or some other graphical indicator. A user can use the first position indicator to place the first medical device.

As described in greater detail above with reference to FIGS. 13, 14A, and 14B, the system 100 can receive emplacement information of the first medical device, as illustrated at block 1512. At block 1514, the system 100 causes the display device to display a first virtual medical device corresponding to the first medical device based at least on the emplacement information of the first medical device, as also described in greater detail above with reference to FIGS. 13, 14A, and 14B.

Additional, fewer, or different blocks can be used to implement the routine 1500 without departing from the spirit and scope of the description. For example, any one or a combination of blocks 1516-1520 can be used as part of routine 1500.

Similar to blocks 1510-1514 described previously, the system can display a second position indicator, receive emplacement information for the second medical device and display a virtual second medical device, as illustrated at blocks 1516-1520, respectively.

Furthermore, in some embodiments and as described in greater detail above with reference to FIGS. 14A and 14B, the system 100 can determine and display draw bars indicating the relative emplacement of the virtual medical devices and/or suggested placements of the virtual medical devices with the target region. In addition, as described in greater detail above, with reference to FIGS. 12A-12D, the system can cause the display device to display various guidance cues (e.g., trajectory indicators, intersection indicators, patient orientation indicators, medical provider location indicators, etc.). As also described in greater detail above, with reference to FIGS. 12A-12D, the system can identify one of the virtual medical devices or position indicators as the foundational medical device and calculate and display various distances between the first and second medical devices, the foundational plane and the medical devices, a target plane and a medical device, etc.

Previous Emplacement of a Medical Device

Referring back to FIG. 14A, FIG. 14A also provides a perspective view of an embodiment in which the location of a medical device that has been removed is shown. In this embodiment, the system receives emplacement information of a medical device within a predetermined area at a first time. In some embodiments the first time is during a medical procedure. Based on the emplacement information, the system can display the medical device, as described previously. The system can also use emplacement information to determine when the medical device has been removed (or when a tracking unit associated with the medical device has been removed).

Typically, when a medical device is removed (or the associated tracking unit is removed), the corresponding virtual medical device is not shown on the display. However, in some embodiments, when a medical device is removed (or when a tracking unit associated with the medical device is removed), the system can display an altered image 1404B (e.g., a faded image) of the virtual medical device.

The system can use the emplacement information received at the first time to determine the emplacement of the altered image 1404B. In certain embodiments, the system displays the altered image 1404B at the location of the virtual medical device at the first time. Over time, as the location of the previously removed (or no longer tracked) medical device becomes less reliable (e.g., due to normal organ movement, etc.), the system can continue to alter the altered image 1404B, until it is removed. For example, the system can make the altered image 1404B more transparent over time (e.g., more faded).

In the interim, a user can use the altered image 1404B to place a second medical device 1406. For example, this can be done when a second biopsy is taken. The system can provide the user with the guidance cues described above with reference to FIGS. 2-12D to aid in the placement of the second medical device 1406. For example, the system can identify the altered image 1404B as a foundational medical device and the second medical device 1406 as a secondary medical device. Using this information, the system can calculate and display one or more guidance cues associated with the altered image 1404B, such as foundational plane indicators, foundational plane intersection indicators, relative spatial indicators, relative distances between portions the second medical device 1406 and the altered image 1404B, etc.

Previous Emplacement of a Medical Device Routine

Figure 16:
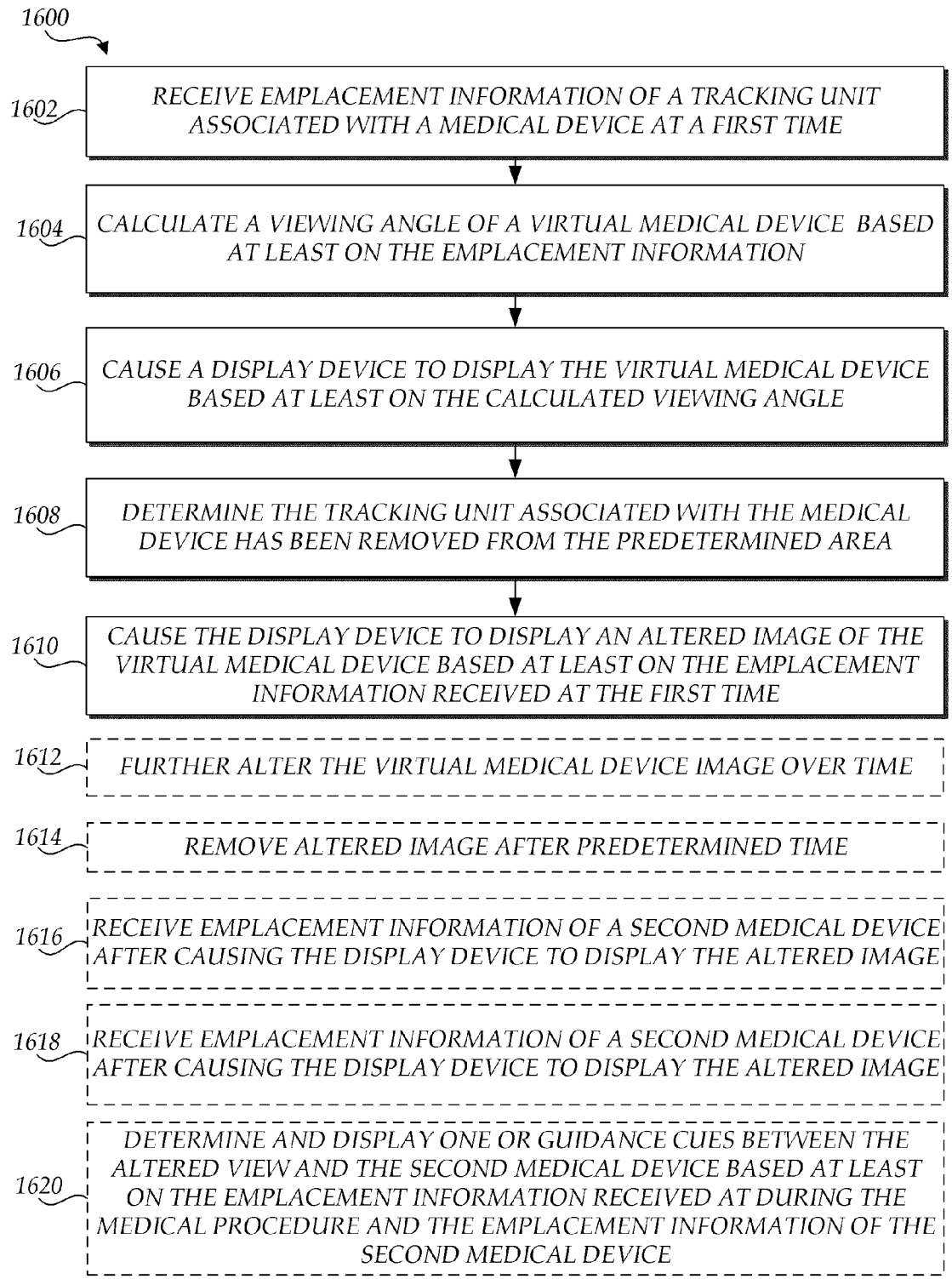
FIG. 16 is a flow diagram illustrative of an embodiment of a routine implemented by the system to display an altered image of a virtual medical device after a medical device has been removed from a predetermined area.

FIG. 16 is a flow diagram illustrative of an embodiment of a routine 1600 implemented by the system 100 to display an altered image of a virtual medical device after a medical device has been removed from a predetermined area. One skilled in the relevant art will appreciate that the elements outlined for routine 1600 can be implemented by one or more computing devices/components that are associated with the system 100, such as the position sensing units 110, 140, the image guidance unit 130, surgical system 149, and/or imaging unit 150. Accordingly, routine 1600 has been logically associated as being generally performed by the system 100. However, the following illustrative embodiment should not be construed as limiting.

At block 1602, the system 100 receives emplacement information of a tracking unit associated with a medical device at a first time. As described in greater detail above with reference to block 1302 of FIG. 13, the system 100 can receive emplacement information of medical devices. In some embodiments, the first time is during a medical procedure, such as during an ablation or biopsy procedure. In certain embodiments, the first time is based on a user input. For example, a healthcare provider can indicate a certain time at which the system 100 is to receive and/or collect the emplacement information. To indicate the predetermined time, the healthcare provider can touch a screen, click a button, or enter information into the system 100, etc.

At block 1604, the system 100 calculates a viewing angle of a virtual medical device in a virtual 3D space based at least on the emplacement information. As described in greater detail above with reference to block 1302 of FIG. 13, the system 100 can calculate the viewing angle of virtual medical devices using received emplacement information.

At block 1606, the system 100 causes a display device to display the virtual medical device based at least on the calculated viewing angle. As described in greater detail above with reference to block 1302 of FIG. 13, the system 100 can cause a display device to display a virtual medical device based on emplacement information of the corresponding medical device within a predetermined area. As mentioned previously, the predetermined area can correspond to a location of a medical procedure, the location of a patient, the location of tracking units, the range of position sensing units, a surgical table, an area corresponding to a virtual 3D area displayed on a display etc.

At block 1608, the system 100 determines that the tracking unit associated with the medical device has been removed from the predetermined area. As the system 100 receives emplacement information from the tracking unit, it can determine the location of the tracking unit and associated medical device. Further, it can determine when the tracking unit has left the predetermined area, such as the area corresponding to the virtual 3D space displayed by the display. To determine that the tracking unit has left the predetermined area, the system 100 can compare the emplacement information of the tracking unit with emplacement information of the predetermined area. When the tracking unit is outside the predetermined area, the system 100 can determine that the tracking unit has been removed from the predetermined area.

In some embodiments, the removal of the tracking unit from the predetermined area corresponds to the removal of the medical device from the predetermined area. In certain embodiments, the removal of the tracking unit from the predetermined area does not correspond to the removal of the medical device from the predetermined area. As described in greater detail above with reference to FIGS. 1A and 1B, in some embodiments, the tracking units can be removed from the medical device. For example, in some cases the tracking unit can be snapped on and/or off of a medical device. In certain embodiments, the tracking unit cannot be easily removed from the medical device. For example, in some cases, the tracking unit is embedded into the medical device or located at or near the tip of the medical device and is inserted into the patient. Accordingly, in some cases a tracking unit can be used with multiple medical devices. Thus, removal of the tracking unit can mean that the associated medical device has been removed or that it is no longer associated with the tracking unit.

At block 1610, the system 100 causes the display device to display an altered image of the virtual medical device based at least on the emplacement information received at the first time. Upon determining that the tracking unit has left the predetermined area, the system 100 can cause the display device to display an altered the image of the virtual medical device.

Typically, when a medical device is removed from the predetermined area, the corresponding virtual medical device is no longer displayed by the system 100. However, in some cases it can be useful to identify where medical devices were located at a first time, such as during previous medical procedures (e.g., ablations, biopsies, etc.). Accordingly, in some embodiments, the system 100 can use the emplacement information received at the first time to display an altered image of the medical device on the display. In some embodiments, the virtual medical device is displayed at its previous location at the predetermined time. In certain embodiments, the system 100 can cause the virtual medical device to be faded or grayed out to indicate that it is no longer present.

Similarly, in cases where a tracking unit is removed from one medical device (or stops working) it can be useful to retain an image of the virtual medical device on the display. Accordingly, in some embodiments, the system 100 can use the emplacement information received during at the predetermined time to display an altered image of the medical device on the display. In some embodiments, the altered image of the virtual medical device is displayed at its last known location (based on the first time). In certain embodiments, the system 100 can cause the virtual medical device to be faded or grayed out to indicate that its location is no longer being tracked and/or may be unreliable.

Additional, fewer, or different blocks can be used to implement the routine 1600 without departing from the spirit and scope of the description. For example, the system can omit blocks 1604 and 1606 determine a previous placement of a medical device based on emplacement information received previously. Using that information, the system can cause the display device to display an altered image of the virtual medical device or can cause the display device to display the virtual medical device. Further, any one or a combination of blocks 1612-1020 can be used as part of routine 1600.

At block 1612, the system 100 further alters the image over time. Over time the reliability of the location of the altered virtual medical device will decrease. This can be due to normal organ movement of the patient or movement due to the healthcare provider. Accordingly, based at least on an amount of time that has passed since the first time, the system can further alter (e.g., fade or gray out) the altered virtual medical device. Thus, the altered virtual medical device can continue to fade until it is removed from the display (e.g., the system ceases to display the altered image), as illustrated at block 1614.

At block 1616, the system 100 can receive emplacement information of a tracking unit associated with a second medical device after causing the display device to display the altered image. In some embodiments, the second medical device is the same as the first medical device. For example, after the medical device has been removed from the predetermined area, the healthcare provider may re-introduce it at another location for another medical procedure. Accordingly, the system 100 can receive the new emplacement information of the tracking unit associated with the medical device. Based on the new emplacement information, the system 100 can calculate the new viewing angle of the virtual medical device in the virtual 3D space and cause the display to display it. However, as mentioned previously, the system 100 can retain the altered image as a reference for the healthcare provider.

Similarly, the system can receive emplacement information of a tracking unit (the same or different tracking unit from the one mentioned above with reference to block 1616) associated with a second medical device after causing the display device to display the altered image, as illustrated at block 1618. The second medical device can be a different medical device with its own tracking unit or a different medical device using the same tracking unit as the first medical device. In either instance, the system 100 can receive the emplacement information of the second medical device (via the emplacement information of the tracking unit), calculate the viewing angle of the second virtual medical device in the virtual 3D space, and cause the display to display it. As mentioned previously, the system 100 can retain the altered image of the first virtual medical device on the display as a reference.

At block 1620, the system 100 determines and displays one or more guidance cues associated with the altered image of the first virtual medical device, the first virtual medical device (based on new emplacement information), and/or the second virtual medical device. The guidance cues can be any one or more of the guidance cues described above with reference to FIGS. 2-12D, 14A, and 14B (e.g., foundational plane indicators, intersection indicators, trajectories, ablation volumes, annotations, etc.). For example, the system can use the altered image of the first virtual medical device as the foundational medical device or as a secondary medical device in determining and displaying the guidance cues. As another example, the system can use the axis of the altered image as a target axis. In some embodiments, the system 100 can display the ablation volume of the altered image based on the volume that was ablated previously, etc.

EXAMPLE EMBODIMENTS

Various example embodiments of the disclosure can be described in view of the following clauses:

Clause 1. A system comprising:
 a display; and
 a computer system comprising a computer processor and memory and in communication with the display and a plurality of tracking units associated with a plurality of medical devices, wherein the computer system is configured to:
  receive emplacement information of at least a portion of the plurality of medical devices within a predetermined area;
  calculate a viewing angle in a virtual 3D space of a plurality of virtual medical devices corresponding to the plurality of medical devices based at least on the emplacement information of the plurality of medical devices; and
  cause the display to display the plurality of virtual medical devices based at least on the calculated viewing angle in the virtual 3D space.

Clause 2. The system of Clause 1, wherein the plurality of medical devices are invasive medical devices.

Clause 3. The system of any of Clauses 1 and 2, wherein the plurality of medical devices comprises a plurality of ablation needles.

Clause 4. The system of any of Clauses 1-3, wherein the computer system is further configured to:
 calculate an ablation volume of each of the plurality of medical devices; and
 cause the display device to display the calculated ablation volume of each of the plurality of medical devices.

Clause 5. The system of any of Clauses 1-4, wherein the computer system is further configured to:
 calculate a trajectory of each of the plurality of medical devices; and cause the display device to display the calculated trajectory of each of the plurality of medical devices.

Clause 6. The system of any of Clauses 1-5, wherein the computer system is further configured to indicate an orientation of a patient with respect to a viewing reference of the image data in the virtual 3D space.

Clause 7. The system of any of Clauses 6, wherein the computer system is further configured to indicate a location of a medical provider with respect to the patient in the virtual 3D space.

Clause 8. The system of any of Clauses 1-7, wherein the computer system is further configured to:
receive emplacement information of a medical imaging device within the predetermined area;
receive image data based at least on the emplacement information of the medical imaging device;
calculate a viewing angle in the virtual 3D space of the image data based at least on the emplacement information of the medical imaging device; and
cause the display device to display the image data based at least on the calculated viewing angle in the virtual 3D space.

Clause 9. The system of any of Clauses 1-8, wherein the image data is received from the medical imaging device.

Clause 10. The system of Clause 9, wherein the medical imaging device comprises an ultrasound transducer and the image data comprises an ultrasound image.

Clause 11. The system of any of Clauses 9 and 10, wherein the computer system is further configured to cause the display device to display a second set of the image data at a second location on the display device.

Clause 12. The system of any of Clauses 9-11, wherein the computer system is further configured to:
calculate an intersection between an image plane of the image data and a calculated trajectory of at least one medical device of the plurality of medical devices; and
cause the display device to display an indication of the intersection of the image plane and the calculated trajectory of the at least one medical device.

Clause 13. The system of any of Clauses 9-12, wherein the computer system is further configured to:
calculate a viewing angle in the virtual 3D space of a virtual medical imaging device space corresponding to the medical imaging device based at least on the emplacement information of the medical imaging device; and
cause the display device to display the virtual medical imaging device space based at least on the calculated viewing angle in the virtual 3D space.

Clause 14. The system of any of Clauses 1-13, further wherein the computer system is further configured to identify a foundational medical device from the plurality of medical devices, wherein each of the plurality of medical devices comprises a first portion and a second portion.

Clause 15. The system of Clause 14, wherein the first portion of each of the plurality of medical devices is a tip of the medical device and the second portion of each of the plurality of medical devices is an end of an electrode of the medical device distal to the tip of the medical device.

Clause 16. The system of any of Clauses 14 and 15, wherein the computer system is further configured to:
determine a first foundational plane based at least on a location of the first portion of the foundational medical device, wherein the first foundational plane is orthogonal to a trajectory of the foundational medical device and intersects with the first portion of the foundational medical device; and
cause the display device to indicate the first foundational plane in the virtual 3D space.

Clause 17. The system of Clause 16, wherein the computer system is further configured to:
calculate a distance between the first foundational plane and the first portion of a medical device of the plurality of medical devices; and
cause the display device to display the plurality of medical devices based at least in part on the calculated distance.

Clause 18. The system of any of Clauses 16 and 17, wherein the computer system is further configured to:
determine an intersection between the first foundational plane and a trajectory of one or more medical devices of the plurality of medical devices; and
cause the display device to display an indication of the intersection of the first foundational plane and the trajectory of the one or more medical devices.

Clause 19. The system of any of Clauses 16-18, wherein the computer system is further configured to:
determine a second foundational plane based at least on a location of the second portion of the foundational medical device, wherein the second foundational plane is orthogonal to a trajectory of the foundational medical device and intersects with the second portion of the foundational medical device; and
cause the display device to indicate the second foundational plane in the virtual 3D space.

Clause 20. The system of any of Clauses 16-19, wherein the computer system is further configured to cause the display device to display a graphical indicator on the foundational plane from the first portion of the foundational medical device to a location on the foundational plane where the first portion of at least one other medical device of the plurality of medical devices is to be located.

Clause 21. The system of any of Clauses 14-20, wherein the computer system is further configured to:
calculate an angle difference between the foundational medical device and at least one other medical device of the plurality of medical devices; and
cause the display device to display an indication of the calculated angle difference.

Clause 22. The system of any of Clauses 14-21, wherein the computer system is further configured to cause the display device to display a plurality of graphical indicators indicating a distance between a plurality of portions of the foundational medical device and a plurality of portions of at least one other medical device of the plurality of medical devices.

Clause 23. The system of any of Clauses 14-22, wherein the computer system is further configured to cause the display device to display a plurality of graphical indicators indicating a distance between at least one of a target axis and a target plane and a plurality of portions of at least one medical device of the plurality of medical devices.

Clause 24. The system of any of Clauses 14-23, wherein the computer system is further configured to:
calculate a distance between the first portion of the foundational medical device and the first portion of at least one other medical device of the plurality of medical devices based at least on the received emplacement information of at least a portion of the plurality of medical devices; and cause the display device to display an indication of the calculated distance.

Clause 25. The system of any of Clauses 24, wherein the indication comprises at least one of a graphical indicator between the first portion of the foundational medical device and the first portion of the at least one other medical device and a number.

Clause 26. The system of any of Clauses 1-25, further comprising the tracking units.

Clause 27. The system of any of Clauses 1-26, further comprising the medical devices.

Clause 28. A method, comprising:
receiving emplacement information of a plurality of needles during a medical procedure of a patient;
receiving emplacement information of a medical imaging device during the medical procedure;
receiving at least one image from the medical imaging device;
calculating a first viewing angle in a virtual 3D space of the at least one image based at least on the emplacement information of the medical imaging device with respect to a perspective view;
calculating a second viewing angle in the virtual 3D space of a virtual medical imaging device corresponding to the medical imaging device based at least on the emplacement information of the medical imaging device with respect to the perspective view;
calculating a plurality of viewing angles in the virtual 3D space of a plurality of virtual needles corresponding to the plurality of needles based at least on the emplacement information of the plurality of needles with respect to the perspective view;
causing the display device to display the at least one image based at least on the first calculated viewing angle in the virtual 3D space;
causing the display device to display the virtual medical imaging device based at least on the second calculated viewing angle in the virtual 3D space; and
causing a display device to display the plurality of virtual needles based at least on the plurality of calculated viewing angles in the virtual 3D space.

Clause 29. A method, comprising
receiving emplacement information of a plurality of medical devices within a predetermined area;
calculating a viewing angle in a virtual 3D space of a plurality of virtual medical devices corresponding to the plurality of medical devices based at least on the emplacement information of the plurality of medical devices; and
causing a display device to display the plurality of virtual medical devices based at least on the calculated viewing angle in the virtual 3D space.

Clause 30. The method of Clause 29, wherein the plurality of medical devices are invasive medical devices.

Clause 31. The method of any of Clauses 29 and 30, wherein the plurality of medical devices comprises a plurality of ablation needles.

Clause 32. The method of any of Clauses 29-31, further comprising:
calculating an ablation volume of each of the plurality of medical devices; and
causing the display device to display the calculated ablation volume of each of the plurality of medical devices.

Clause 33. The method of any of Clauses 29-32, further comprising:
calculating a trajectory of each of the plurality of medical devices; and
causing the display device to display the calculated trajectory of each of the plurality of medical devices.

Clause 34. The method of any of Clauses 29-33, further comprising indicating an orientation of a patient with respect to a viewing reference of the image data in the virtual 3D space.

Clause 35. The method of Clause 34, further comprising indicating a location of a medical provider with respect to the patient in the virtual 3D space.

Clause 36. The method of any of Clauses 29-35, further comprising:
receiving emplacement information of a medical imaging device within the predetermined area;
receiving image data based at least on the emplacement information of the medical imaging device;
calculating a viewing angle in the virtual 3D space of the image data based at least on the emplacement information of the medical imaging device; and
causing the display device to display the image data based at least on the calculated viewing angle in the virtual 3D space.

Clause 37. The method of Clause 36, wherein the image data is received from the medical imaging device.

Clause 38. The method of any of Clauses 35 or 37, wherein the medical imaging device comprises an ultrasound transducer and the image data comprises an ultrasound image.

Clause 39. The method of any of Clauses 35-38, further comprising causing the display device to display a second set of the image data at a second location on the display device.

Clause 40. The method of any of Clauses 35-39, further comprising:
calculating an intersection between an image plane of the image data and a calculated trajectory of at least one medical device of the plurality of medical devices; and
causing the display device to display an indication of the intersection of the image plane and the calculated trajectory of the at least one medical device.

Clause 41. The method of any of Clauses 35-40, further comprising:
calculating a viewing angle in the virtual 3D space of a virtual medical imaging device space corresponding to the medical imaging device based at least on the emplacement information of the medical imaging device; and
causing the display device to display the virtual medical imaging device space based at least on the calculated viewing angle in the virtual 3D space.

Clause 42. The method of any of Clauses 29-41, further comprising identifying a foundational medical device from the plurality of medical devices, wherein each of the plurality of medical devices comprises a first portion and a second portion.

Clause 43. The method of Clause 42, wherein the first portion of each of the plurality of medical devices is a tip of the medical device and the second portion of each of the plurality of medical devices is an end of an electrode of the medical device distal to the tip of the medical device.

Clause 44. The method of any of Clauses 42 and 43, further comprising:
  determining a first foundational plane based at least on a location of the first portion of the foundational medical device, wherein the first foundational plane is orthogonal to a trajectory of the foundational medical device and intersects with the first portion of the foundational medical device; and
  causing the display device to indicate the first foundational plane in the virtual 3D space.

Clause 45. The method of Clause 44, further comprising:
  calculating a distance between the first foundational plane and the first portion of a medical device of the plurality of medical devices; and
  causing the display device to display the plurality of medical devices based at least in part on the calculated distance.

Clause 46. The method of any of Clauses 44 and 45, further comprising:
  determining an intersection between the first foundational plane and a trajectory of one or more medical devices of the plurality of medical devices; and
  causing the display device to display an indication of the intersection of the first foundational plane and the trajectory of the one or more medical devices.

Clause 47. The method of any of Clauses 44-46, further comprising:
  determining a second foundational plane based at least on a location of the second portion of the foundational medical device, wherein the second foundational plane is orthogonal to a trajectory of the foundational medical device and intersects with the second portion of the foundational medical device; and
  causing the display device to indicate the second foundational plane in the virtual 3D space.

Clause 48. The method of any of Clauses 44-47, further comprising causing the display device to display a graphical indicator on the foundational plane from the first portion of the foundational medical device to a location on the foundational plane where the first portion of at least one other medical device of the plurality of medical devices.

Clause 49. The method of any of Clauses 42-48, further comprising:
  calculating an angle difference between the foundational medical device and at least one other medical device of the plurality of medical devices; and
  causing the display device to display an indication of the calculated angle difference.

Clause 50. The method of any of Clauses 42-49, further comprising causing the display device to display a plurality of graphical indicators indicating a distance between a plurality of portions of the foundational medical device and a plurality of portions of at least one other medical device of the plurality of medical devices.

Clause 51. The method of any of Clauses 42-50, further comprising causing the display device to display a plurality of graphical indicators indicating a distance between at least one of a target axis and a target plane and a plurality of portions of at least one medical device of the plurality of medical devices.

Clause 52. The method of any of Clauses 42-51, further comprising:
  calculating a distance between the first portion of the foundational medical device and the first portion of at least one other medical device of the plurality of medical devices based at least on the received emplacement information of at least a portion of the plurality of medical devices; and
  causing the display device to display an indication of the calculated distance.

Clause 53. The method of any of Clauses 52, wherein the indication comprises at least one of a graphical indicator between the first portion of the foundational medical device and the first portion of the at least one other medical device and a number.

Clause 54. A computer-readable, non-transitory storage medium having one or more computer-executable modules, the one or more computer-executable modules comprising:
  a first module in communication with a display and a plurality of tracking units associated with a plurality of medical devices, wherein the first module is configured to:
    receive emplacement information of at least a portion of the plurality of medical devices within a predetermined area;
    calculate a viewing angle in a virtual 3D space of a plurality of virtual medical devices corresponding to the plurality of medical devices based at least on the emplacement information of the plurality of medical devices; and
    cause the display to display the plurality of virtual medical devices based at least on the calculated viewing angle in the virtual 3D space.

Clause 54. The computer-readably medium of Clause 54, wherein the one or more computer-executable modules are configured to perform any of, or any combination of, the steps recited in Clauses 29-53.

Clause 55. A system comprising:
  a display; and
  a computer system comprising a computer processor and memory and in communication with the display and a tracking unit associated with a first medical device and, wherein the computer system is configured to:
    receive emplacement information of a target region;
    determine a first position relative to the target region for a first medical device based at least on the emplacement information of the target region;
    determine a second position relative to the target region for a second medical device based at least on the emplacement information of the target region;
    cause a display device to display the target region;
    cause the display device to display a first position indicator to indicate a suggested placement of the first medical device;
    receive emplacement information of the first medical device; and
    cause the display device to display a first virtual medical device corresponding to the first medical device based at least on the emplacement information of the first medical device.

Clause 56. The system of Clause 55, further comprising the tracking unit.

Clause 57. The system of any of Clauses 55 and 56, further comprising the first medical device and the second medical device.

Clause 58. The system of any of Clauses 55-57, wherein the plurality of medical devices are invasive medical devices.

Clause 59. The system of any of Clauses 55-58, wherein the plurality of medical devices comprises at least one of a plurality of ablation needles and a plurality of biopsy needles.

Clause 60. The system of any of Clauses 55-59, wherein the computer system is further configured to:
calculate a trajectory of each of the plurality of medical devices; and
cause the display device to display the calculated trajectory of each of the plurality of medical devices.

Clause 61. The system of any of Clauses 55-60, wherein the computer system is further configured to indicate an orientation of a patient with respect to a viewing reference of the image data in the virtual 3D space.

Clause 62. The system of any of Clauses 61, wherein the computer system is further configured to indicate a location of a medical provider with respect to the patient in the virtual 3D space.

Clause 63. The system of any of Clauses 55-62, wherein the computer system is further configured to:
cause the display device to display a second position indicator to indicate a suggested placement of the second medical device;
receive emplacement information of the second medical device; and
cause the display device to display a second virtual medical device corresponding to the second medical device based at least on the emplacement information of the second medical device.

Clause 64. The system of any of Clauses 55-63, wherein the computer system is further configured to:
determine a distance between a portion of the target region and a portion of the first medical device;
cause the display device to display a graphical indicator indicating the distance between the portion of the target region and the portion of the first medical device Clause 65. The system of any of Clauses 55-64 wherein the computer system is further configured to cause the display device to display a plurality of graphical indicators indicating a distance between at least one of a target axis and a target plane and a plurality of portions of at least one of the first medical device and the second medical device.

Clause 66. A method for multi-needle image guided placement, comprising:
receiving emplacement information of a target region during a medical procedure;
determining a first suggested position relative to the target region for a first needle based at least on the emplacement information of the target region;
determining a second suggested position relative to the target region for a second needle based at least on the emplacement information of the target region;
causing a display device to display the target region;
causing the display device to display a first position indicator at the first suggested position to indicate a suggested placement for the first needle;
causing the display device to display a second position indicator at the second suggested position to indicate a suggested placement for second needle;
receiving emplacement information of the first needle;
causing the display device to display a first virtual needle corresponding to the first needle based at least on the emplacement information of the first needle;
receiving emplacement information of the second needle; and
causing the display device to display a second virtual needle corresponding to the second needle based at least on the emplacement information of the second needle.

Clause 67. A method for multi-medical device image guided placement, comprising:
receiving emplacement information of a target region;
determining a first position relative to the target region for a first medical device based at least on the emplacement information of the target region;
determining a second position relative to the target region for a second medical device based at least on the emplacement information of the target region;
causing a display device to display the target region;
causing the display device to display a first position indicator to indicate a suggested placement of the first medical device;
receiving emplacement information of the first medical device; and
causing the display device to display a first virtual medical device corresponding to the first medical device based at least on the emplacement information of the first medical device.

Clause 68. The method of Clause 67, wherein the plurality of medical devices are invasive medical devices.

Clause 69. The method of any of Clauses 67 and 68, wherein the plurality of medical devices comprises at least one of a plurality of ablation needles and a plurality of biopsy needles.

Clause 70. The method of Clause 67-69, further comprising:
calculating a trajectory of each of the plurality of medical devices; and
causing the display device to display the calculated trajectory of each of the plurality of medical devices.

Clause 71. The method of Clause 67-70, further comprising indicating an orientation of a patient with respect to a viewing reference of the image data in the virtual 3D space.

Clause 72. The method of Clause 71, further comprising indicating a location of a medical provider with respect to the patient in the virtual 3D space.

Clause 73. The method of any of Clauses 67-72, further comprising:
causing the display device to display a second position indicator to indicate a suggested placement of the second medical device;
receiving emplacement information of the second medical device; and
causing the display device to display a second virtual medical device corresponding to the second medical device based at least on the emplacement information of the second medical device.

The method of any of Clauses 1, further comprising:
determining a distance between a portion of the target region and a portion of the first medical device;
causing the display device to display a graphical indicator indicating the distance between the portion of the target region and the portion of the first medical device Clause 74. The method of any of Clauses 67-74, further comprising causing the display device to display a plurality of graphical indicators indicating a distance between at least one of a target axis and a target plane and a plurality of portions of at least one of the first medical device and the second medical device.

Clause 75. A computer-readable, non-transitory storage medium having one or more computer-executable modules, the one or more computer-executable modules comprising:
- a first module in communication with a display and a tracking unit associated with a first medical device, wherein the first module is configured to:
  - receive emplacement information of a target region;
  - determine a first position relative to the target region for a first medical device based at least on the emplacement information of the target region;
  - determine a second position relative to the target region for a second medical device based at least on the emplacement information of the target region;
  - cause a display device to display the target region;
  - cause the display device to display a first position indicator to indicate a suggested placement of the first medical device;
  - receive emplacement information of the first medical device; and
  - cause the display device to display a first virtual medical device corresponding to the first medical device based at least on the emplacement information of the first medical device.

Clause 76. The computer-readably medium of Clause 75, wherein the one or more computer-executable modules are configured to perform any of, or any combination of, the steps recited in Clauses 67-73.

Clause 77. A system comprising:
- a display;
- a computer system comprising a computer processor and memory and in communication with the display and a tracking unit associated with a medical device, wherein the computer system is configured to:
  - receive emplacement information of a tracking unit within a predetermined area and associated with a medical device at a first time;
  - determine the tracking unit associated with the medical device has been removed from the predetermined area at a second time after the first time; and
  - cause the display device to display an altered image of a virtual medical device based at least on the emplacement information received at the first time.

Clause 78. The system of Clause 77, wherein the computer system is further configured to:
- calculate a viewing angle in a virtual 3D space of a virtual medical device corresponding to the medical device based at least on the emplacement information;
- cause a display device to display the virtual medical device based at least on the calculated viewing angle in the virtual 3D space;

Clause 79. The system of any of Clauses 77 and 78, further comprising the tracking unit.

Clause 80. The system of any of Clauses 77-79, further comprising the first medical device and the second medical device.

Clause 81. The system of any of Clauses 77, wherein the computer system is further configured to further alter the altered image of the first virtual medical device based at least on an amount of time that has passed since the first time.

Clause 82. The system of any of Clauses 77-81, wherein the computer system is further configured to cease display of the altered image once a threshold time is satisfied.

Clause 83. The system of any of Clauses 77-82, wherein the virtual medical device is a first virtual medical device, the method wherein the computer system is further configured to:
- receive emplacement information of a tracking unit associated with a second medical device at a third time after the second time; and
- calculate a second viewing angle in the virtual 3D space of a second virtual medical device based at least on the emplacement information received at the third time; and
- cause the display device to display the second virtual medical device based at least on the second calculated viewing angle in the virtual 3D space, wherein the altered image of the virtual medical device is also displayed.

Clause 84. The system of Clause 83, wherein the tracking unit associated with the first medical device and the tracking unit associated with the second medical device is the same.

Clause 85. The system of any of Clauses 83 and 84, wherein the second virtual medical device corresponds to a second medical device that is different from the first medical device.

Clause 86. The system of any of Clauses 83-85, wherein the second virtual medical device corresponds to the first medical device.

Clause 87. The system of any of Clauses 83-86, wherein the computer system is further configured to cause the display device to display a plurality of graphical indicators indicating a distance between at least one of a target axis and a target plane and a plurality of portions of the second virtual medical device.

Clause 88. The system of any of Clauses 87, wherein the target axis is the axis of the altered image of the first virtual medical device.

Clause 89. The system of any of Clauses 83-88, wherein the computer system is further configured to cause the display device to display a plurality of graphical indicators indicating a distance between a plurality of portions of the altered image of the first virtual medical device and a plurality of portions of the second virtual medical device.

Clause 90. The system of any of Clauses 83-89, wherein the computer system is further configured to:
- calculate a distance between a first portion of the altered image of the first medical device and a first portion of the second virtual medical device based at least on the received emplacement information at the first time and the received emplacement information at the third time; and
- cause the display device to display an indication of the calculated distance.

Clause 91. A method, comprising
- receiving emplacement information of a first needle within a predetermined area during a first medical procedure;
- calculating a first viewing angle in a virtual 3D space of a first virtual needle corresponding to the first needle based at least on the emplacement information of the first needle;
- causing a display device to display the first virtual needle based at least on the first calculated viewing angle in the virtual 3D space;
- determining the first needle is removed from the predetermined area after the first medical procedure;

causing the display device to display an altered image of the first virtual needle based at least on the emplacement information received during the first medical procedure and on an amount of time that has passed since the first medical procedure;

receiving emplacement information of a second needle after the first medical procedure and prior to a second medical procedure;

calculating a viewing angle in the virtual 3D space of a second virtual needle corresponding to the second needle based at least on the emplacement information of the second needle; and causing the display device to display the second virtual needle based at least on the second calculated viewing angle in the virtual 3D space, wherein at least for a time period the altered image of the first virtual needle is displayed simultaneously with the second virtual needle.

Clause 92. A method, comprising
receiving emplacement information of a tracking unit associated with a medical device at a first time;
calculating a viewing angle in a virtual 3D space of a virtual medical device corresponding to the medical device based at least on the emplacement information;
causing a display device to display the virtual medical device based at least on the calculated viewing angle in the virtual 3D space;
determining the tracking unit associated with the medical device has been removed from the predetermined area at a second time after the first time;
causing the display device to display an altered image of the virtual medical device based at least on the emplacement information received at the first time.

Clause 93. The method of Clause 92, further comprising further altering the altered image of the first virtual medical device based at least on an amount of time that has passed since the first time.

Clause 94. The method of any of Clauses 92 and 93, further comprising ceasing display of the altered image once a threshold time is satisfied.

Clause 95. The method of any of Clauses 92-94, wherein the virtual medical device is a first virtual medical device, the method further comprising:
receiving emplacement information of a tracking unit associated with a second medical device at a third time after the second time; and
calculating a second viewing angle in the virtual 3D space of a second virtual medical device based at least on the emplacement information received at the third time; and
causing the display device to display the second virtual medical device based at least on the second calculated viewing angle in the virtual 3D space, wherein the altered image of the virtual medical device is also displayed.

Clause 96. The method of Clause 95, wherein the tracking unit associated with the first medical device and the tracking unit associated with the second medical device is the same.

Clause 97. The method of any of Clauses 95 and 96, wherein the second virtual medical device corresponds to a second medical device that is different from the first medical device.

Clause 98. The method of any of Clauses 95-97, wherein the second virtual medical device corresponds to the first medical device.

Clause 99. The method of any of Clauses 95-98, further comprising causing the display device to display a plurality of graphical indicators indicating a distance between at least one of a target axis and a target plane and a plurality of portions of the second virtual medical device.

Clause 100. The method of Clause 99, wherein the target axis is the axis of the altered image of the first virtual medical device.

Clause 101. The method of any of Clauses 95-100, further comprising causing the display device to display a plurality of graphical indicators indicating a distance between a plurality of portions of the altered image of the first virtual medical device and a plurality of portions of the second virtual medical device.

Clause 102. The method of any of Clauses 95-101, further comprising:
calculating a distance between a first portion of the altered image of the first medical device and a first portion of the second virtual medical device based at least on the received emplacement information at the first time and the received emplacement information at the third time; and
causing the display device to display an indication of the calculated distance.

Clause 103. A computer-readable, non-transitory storage medium having one or more computer-executable modules, the one or more computer-executable modules comprising:
a first module in communication with a display and a tracking unit associated with a medical device, wherein the first module is configured to:
receive emplacement information of a tracking unit associated with a medical device at a first time;
calculate a viewing angle in a virtual 3D space of a virtual medical device corresponding to the medical device based at least on the emplacement information;
cause a display device to display the virtual medical device based at least on the calculated viewing angle in the virtual 3D space;
determine the tracking unit associated with the medical device has been removed from the predetermined area at a second time after the first time;
cause the display device to display an altered image of the virtual medical device based at least on the emplacement information received at the first time.

Clause 104. The computer-readable medium of Clause 103, wherein the one or more computer-executable modules are configured to perform any of, or any combination of, the steps recited in Clauses 93-102.

Clause 105. A method, comprising
receiving emplacement information of a tracking unit associated with a medical device at a first time;
determining the tracking unit associated with the medical device has been removed from the predetermined area at a second time after the first time; and
causing the display device to display an altered image of a virtual medical device based at least on the emplacement information received at the first time.

TERMINOLOGY

Those having skill in the art will further appreciate that the various illustrative logical blocks, modules, circuits, and process steps described in connection with the implementations disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of the present invention. One skilled in the art will recognize that a portion, or a part, can comprise something less than, or equal to, a whole. For example, a portion of a collection of pixels can refer to a sub-collection of those pixels.

The various illustrative logical blocks, modules, and circuits described in connection with the implementations disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The steps of a method or process described in connection with the implementations disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of non-transitory storage medium known in the art. An exemplary computer-readable storage medium is coupled to the processor such the processor can read information from, and write information to, the computer-readable storage medium. In the alternative, the storage medium can be integral to the processor. The processor and the storage medium can reside in an ASIC. The ASIC can reside in a user terminal, camera, or other device. In the alternative, the processor and the storage medium can reside as discrete components in a user terminal, camera, or other device.

Headings are included herein for reference and to aid in locating various sections. These headings are not intended to limit the scope of the concepts described with respect thereto. Such concepts can have applicability throughout the entire specification.

The previous description of the disclosed implementations is provided to enable any person skilled in the art to make or use the present invention. Various modifications to these implementations will be readily apparent to those skilled in the art, and the generic principles defined herein can be applied to other implementations without departing from the spirit or scope of the invention. Thus, the present invention is not intended to be limited to the implementations shown herein but is to be accorded the widest scope consistent with the principles and novel features disclosed herein.

What is claimed is:

1. A method, comprising:
receiving emplacement information of a plurality of needles, the plurality of needles comprising at least a first needle and a second needle;
receiving emplacement information of a medical imaging device;
receiving at least one image from the medical imaging device;
calculating a first perspective view of the at least one image in a virtual 3D space based at least on the emplacement information of the medical imaging device with respect to a user;
calculating a second perspective view of a virtual medical imaging device corresponding to the medical imaging device in the virtual 3D space based at least on the emplacement information of the medical imaging device with respect to the user;
calculating a plurality of perspective views of a plurality of virtual needles corresponding to the plurality of needles in the virtual 3D space based at least on the emplacement information of the plurality of needles with respect to the user, the plurality of virtual needles comprising at least a first virtual needle corresponding to the first needle and a second virtual needle corresponding to the second needle;
determining a relative angular difference between a longitudinal axis of the first virtual needle and a longitudinal axis of the second virtual needle based at least on the emplacement information of the first needle and the second needle;
determining a foundational plane based at least on the emplacement information of the first needle, wherein the foundational plane is orthogonal to the longitudinal axis of the first virtual needle and intersects with the first virtual needle;
causing the display device to display the perspective view of the at least one image in the virtual 3D space;
causing the display device to display the perspective view of the virtual medical imaging device in the virtual 3D space;
causing the display device to display the plurality of perspective views of the plurality of virtual needles in the virtual 3D space;
causing the display device to display in the virtual 3D space a graphical indicator between at least a portion of the second virtual needle and a target axis that is different from and parallel to the longitudinal axis of the first virtual needle, wherein the graphical indicator indicates the relative angular difference between the longitudinal axis of the first virtual needle and the longitudinal axis of the second virtual needle; and
causing the display device to display in the virtual 3D space at least a portion of the foundational plane that is located between the first virtual needle and an intersection of the longitudinal axis of the second virtual needle and the foundational plane.

2. The method of claim 1, wherein the plurality of needles comprises a plurality of ablation needles.

3. The method of claim 1, wherein the medical imaging device comprises an ultrasound transducer and the at least one image comprises an ultrasound image.

4. The method of claim 1, further comprising:
calculating an intersection between an image plane of the at least one image and a calculated trajectory of at least one needle of the plurality of needles; and causing the display device to display an indication of the intersection of the image plane and the calculated trajectory of the at least one needle.

5. The method of claim 1, wherein the foundational plane intersects at least a portion of at least one of an electrode and an emitter of the first virtual needle.

6. The method of claim 1, wherein the foundational plane intersects at least a portion of a tip of the first virtual needle.

7. The method of claim 1, further comprising causing the display device to display an indication of an intersection of the foundational plane and the longitudinal axis of the second virtual needle.

8. The method of claim 1, wherein the foundational plane is a first foundational plane and the first foundational plane intersects with the first virtual needle at a first location, the method further comprising causing the display device to display in the virtual 3D space at least a portion of a second foundational plane that is located between a second location of the first virtual needle and an intersection of the longitudinal axis of the second virtual needle and the second foundational plane, wherein the second foundational plane is orthogonal to a trajectory of the first virtual needle and intersects with the first virtual needle at the second location.

9. The method of claim 1, further comprising causing the display device to display a plurality of graphical indicators indicating a distance between a plurality of locations on the first virtual needle and a plurality of locations on the second virtual needle.

10. The method of claim 1, further comprising causing the display device to display a plurality of graphical indicators indicating a distance between the target axis and a plurality of portions of the second virtual needle.

11. A system comprising:
a computer system in communication with a display, the computer system comprising a computer processor and a non-transitory storage medium, wherein the computer system is configured to:
receive emplacement information of the plurality of needles, wherein the plurality of needles comprise at least a first needle and a second needle;
receive emplacement information of a medical imaging device;
receive at least one image from the medical imaging device;
calculate a first perspective view of the at least one image in a virtual 3D space based at least on the emplacement information of the medical imaging device with respect to a user;
calculate a second perspective view of a virtual medical imaging device corresponding to the medical imaging device in the virtual 3D space based at least on the emplacement information of the medical imaging device with respect to the user;
calculate a plurality of perspective views of a plurality of virtual needles corresponding to the plurality of needles in the virtual 3D space based at least on the emplacement information of the plurality of needles with respect to the user, the plurality of virtual needles comprising at least a first virtual needle corresponding to the first needle and a second virtual needle corresponding to the second needle;
determine a relative angular difference between a longitudinal axis of the first virtual needle and a longitudinal axis of the second virtual needle based at least on the emplacement information of the first needle and the second needle;
determine a foundational plane based at least the emplacement information of the first needle, wherein the foundational plane is orthogonal to the longitudinal axis of the first virtual needle and intersects with the first virtual needle;
cause the display to display the perspective view of the at least one image in the virtual 3D space;
cause the display to display the perspective view of the virtual medical imaging device in the virtual 3D space;
cause the display to display the plurality of perspective views of the plurality of virtual needles in the virtual 3D space;
cause the display to display in the virtual 3D space a graphical indicator between at least a portion of the second virtual needle and a target axis that is different from and parallel to the longitudinal axis of the first virtual needle, wherein the graphical indicator indicates the relative angular difference between the longitudinal axis of the first virtual needle and the longitudinal axis of the second virtual needle; and
cause the display to display in the virtual 3D space at least a portion of the foundational plane that is located between the first virtual needle and an intersection of the longitudinal axis of the second virtual needle and the foundational plane.

12. The system of claim 11, wherein the plurality of needles comprises a plurality of ablation needles.

13. The system of claim 11, wherein the computer system is further configured to:
calculate an ablation volume of each of the plurality of needles; and
cause the display to display the calculated ablation volume of each of the plurality of medical devices.

14. The system of claim 11, wherein the computer system is further configured to:
calculate a trajectory of each of the plurality of medical devices; and
cause the display to display the calculated trajectory of each of the plurality of medical devices.

15. The system of claim 11, wherein the computer system is further configured to indicate an orientation of a patient with respect to a viewing reference of the virtual 3D space.

16. The system of claim 15, wherein the computer system is further configured to indicate a location of the user with respect to the patient in the virtual 3D space.

17. The system of claim 11, wherein the medical imaging device comprises an ultrasound transducer and the at least one image comprises an ultrasound image.

18. The system of claim 11, wherein the computer system is further configured to:
calculate an intersection between an image plane of the at least one image and a calculated trajectory of at one least needle of the plurality of needles; and
cause the display to display an indication of the intersection of the image plane and the calculated trajectory of the at least one needle.

19. The system of claim 11, wherein the foundational plane intersects at least a portion of at least one of an electrode and an emitter of the first virtual needle.

20. The system of claim 11, wherein the foundational plane intersects at least a portion of a tip of the needle.

21. The system of claim 11, wherein the computer system is further configured to cause the display to display an indication of an intersection of the foundational plane and a longitudinal axis of the second virtual needle.

22. The system of claim 11, wherein the foundational plane is a first foundational plane and the first foundational plane intersects with the first virtual needle at a first location, and the computer system is further configured to cause the display to display in the virtual 3D space at least a portion of a second foundational plane that is located between a second location of the first virtual needle and an intersection of the longitudinal axis of the second virtual needle and the second foundational plane, wherein the second foundational plane is orthogonal to the longitudinal axis of the first virtual needle and intersects with the second location of the first virtual needle.

23. The system of claim 11, wherein the computer system is further configured to cause the display to display a plurality of graphical indicators indicating a distance between a plurality of portions of the first virtual needle and a plurality of portions of the second virtual needle.

24. The system of claim 11, wherein the computer system is further configured to cause the display to display a plurality of graphical indicators indicating a distance between a plurality of locations on the target axis and a plurality of portions of the second virtual needle.

* * * * *

UNITED STATES PATENT AND TRADEMARK OFFICE
CERTIFICATE OF CORRECTION

PATENT NO.        : 8,670,816 B2
APPLICATION NO.   : 13/753274
DATED             : March 11, 2014
INVENTOR(S)       : Green et al.

It is certified that error appears in the above-identified patent and that said Letters Patent is hereby corrected as shown below:

On the title page (item 72, Inventors) at line 1, change "Carrborro, NC" for Caroline Green to --Carrboro, NC--.

In column 1 (title page 5, item 56) at line 50, Under Other Publications, change "Hvgiene" to --Hygiene--.

In column 2 (title page 5, item 56) at line 48, Under Other Publications, change "Teleoperalion,"" to --Teleoperation,"--.

In column 2 (title page 6, item 56) at line 54, Under Other Publications, change "Guidling Sterotactic" to --Guiding Stereotactic--.

In the Specification

In column 10 at line 3, Change "sheers," to --shears,--.

In column 17 at line 26, Change "1056" to --1056,--.

In column 21 at lines 66-67, Change "and or" to --and/or--.

In the Claims

In column 52 at line 1, In Claim 11, after "least" insert --on--.

In column 52 at line 54, In Claim 18, change "one least" to --least one--.

Signed and Sealed this
Twenty-first Day of October, 2014

Michelle K. Lee
*Deputy Director of the United States Patent and Trademark Office*